(12) United States Patent
Cerri et al.

(10) Patent No.: US 8,664,210 B2
(45) Date of Patent: Mar. 4, 2014

(54) AMINOOXIME DERIVATIVES OF 2- AND/OR 4-SUBSTITUTED ANDROSTANES AND ANDROSTENES AS MEDICAMENTS FOR CARDIOVASCULAR DISORDERS

(75) Inventors: Alberto Cerri, Milan (IT); Giuseppe Bianchi, Milan (IT); Giorgio Fedrizzi, Treviglio (IT); Patrizia Ferrari, Varese (IT); Mauro Gobbini, Mercallo (IT); Marco Torri, Rho (IT); Giuseppe Marazzi, Milan (IT); Walter Cabri, Rozzano (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 274 days.

(21) Appl. No.: 12/680,988

(22) PCT Filed: Sep. 18, 2008

(86) PCT No.: PCT/EP2008/062483
§ 371 (c)(1),
(2), (4) Date: Aug. 3, 2010

(87) PCT Pub. No.: WO2009/047101
PCT Pub. Date: Apr. 16, 2009

(65) Prior Publication Data
US 2010/0324003 A1 Dec. 23, 2010

(30) Foreign Application Priority Data
Oct. 12, 2007 (EP) ...................... 07118362

(51) Int. Cl.
*A61K 31/58* (2006.01)
*C07J 41/00* (2006.01)
(52) U.S. Cl.
USPC ........... 514/176; 514/177; 514/178; 514/182; 540/106; 552/520
(58) Field of Classification Search
USPC ................. 552/520; 514/177, 178, 182, 176; 540/106
See application file for complete search history.

(56) References Cited

U.S. PATENT DOCUMENTS 5,144,017 A 9/1992 Labella et al.

FOREIGN PATENT DOCUMENTS

| EP | 0 825 197 | 2/1998 |
| EP | 1 156 058 | 11/2001 |

OTHER PUBLICATIONS

DeMunari, S. et al., "Structure-based design and synthesis of novel potent Na+, K+-ATPase inhibitors derived from a 5α, 14α-androstane scaffold as positive inotropic compound" J. of Med. Chem., vol. 46, No. 17, Jul. 23, 2003, pp. 3644-3654.
Temma K. et al., "Effects of progesterone derivatives on sodium pump activity and force of myocardial contraction in isolated guinea-pig heart" Research Communications in Chemical Pathology and Pharmacology, vol. 41., No. 1, Jan. 1, 1983, pp. 51-63.

*Primary Examiner* — Barbara P Badio
(74) *Attorney, Agent, or Firm* — Lucas & Mercanti, LLP

(57) ABSTRACT

New aminooxime derivatives at position 3 of 2- and/or 4-substituted androstanes and androstenes, processes for their preparation, and to pharmaceutical compositions containing them for the treatment of cardiovascular disorders, such as heart failure and hypertension. In particular compounds having the general formula (I) are described, where the radicals have the meanings described in detail in the application.

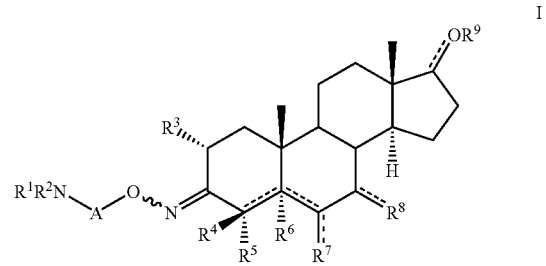

7 Claims, No Drawings

AMINOOXIME DERIVATIVES OF 2- AND/OR 4-SUBSTITUTED ANDROSTANES AND ANDROSTENES AS MEDICAMENTS FOR CARDIOVASCULAR DISORDERS

This application is a 35 U.S.C. §371 national phase of PCT/EP2008/062483 filed on Sep. 18, 2008, which claims priority to and the benefit of European Application No. 07118362.8 filed on Oct. 12, 2007, the contents of which are incorporated herein by reference.

The present invention relates to new aminooxime derivatives at position 3 of 2- and/or 4-substituted androstanes and androstenes, optionally 5- and/or 6- and/or 7-substituted, processes for their preparation, and to pharmaceutical compositions containing them for the treatment of cardiovascular disorders, such as heart failure and hypertension.

BACKGROUND OF THE INVENTION

Cardiovascular diseases are still the first cause of morbidity and mortality in the western world; among these, hypertension and heart failure are two frequent diseases. Hypertension is one of the most important cardiovascular risk factor and more than one third of population over 60 suffers from this disease. Congestive heart failure affects 1-2% of the population and even 10% of the very elderly; the percentage is expected to rise (Sharpe N., et al., *The Lancet*, 1998, 352, (suppl. 1), 3-17). Beside, hypertension may be one of more important causes of heart failure in the elderly (Remme W. J., et al., *Eur. Heart J.*, 2001, 22, 1527-1560). Although a number of effective drugs are available for the treatment of both hypertension and heart failure, further research is in progress to find more effective and safer compounds. Several drugs are used in combination for the treatment of heart failure, and among positive inotropic agents, digoxin is the most prescribed digitalis cardiac glycoside that can improve the myocardial performance. A very well known drawback of digitalis drugs is their arrhythmogenic side effect. Evidence of digitalis toxicity emerges at two- to three-fold higher serum concentration than the therapeutic dose, such as disturbances of conduction and cardiac arrhythmias which are characteristics of digitalis toxicity (Hoffman, B. F., et al., *Digitalis and Allied Cardiac Glycosides; The Pharmacological Basis of Therapeutics*, 8th ed.; Goodman Gilman, A.; Nies, A. S.; Rall, T. W.; Taylor, P., Eds.; Pergamon Press, New York, 1990, 814-839).

The capability of the natural digitalis compounds to increase the myocardial force of contraction is strictly related to their cardenolide structure having a 17β-lactone on a 14-hydroxy-5β,14β-androstane skeleton.

DESCRIPTION OF THE PRIOR ART

6-Hydroxy and 6-oxoandrostane derivatives are disclosed in EP0825197 filed in the name of the Applicant as ligands and inhibitors of Na+,K+-ATPase, and positive inotropic agents. The same compounds are also reported by De Munari S., et al., *J. Med. Chem.* 2003, 64, 3644. The problem of dealing with mixtures of isomers is clearly addressed in this paper. 3-Oxime derivatives were obtained as mixtures of E and Z isomers in a ratio of about 1:1. Efforts to separate the pure isomers had poor success and the separation was accomplished only in particular cases through a complicated and inefficient method. If compound 22i was obtained in a one step procedure from the advanced intermediate 1c in 85% yield, the corresponding pure isomers 22j and 22k were obtained in very poor yield (32% yield and 16% respectively) in a two step procedure from compound 22i. Therefore, such a preparation is not really sustainable. Consequently, it cannot be considered suitable to solve the problem of getting pure and potent androstanes and androstenes inhibitors. The introduction of a methyl group in the adjacent position of the 3-oxime solved the problem of obtaining pure isomers. Compounds 22c and 22d were obtained as single isomers but they showed low potencies when compared to the easily obtainable isomeric mixtures. The des-methyl compound 22b is indeed more active than its counterpart compound 22c by two orders of magnitude. In the same way, compound 22d is 30 times less active than compound 22b.

It is well known that administration of mixtures of isomers may give rise to problems due to different chemical and physical stability, pharmacological activity, toxicity, and potency of the isomers; besides, isomers may interconvert in vivo with different rates. Also the pharmacokinetics of isomers may be different contributing to increase the difficulties in developing a mixture of isomers: in fact, absorption, metabolism and excretion may vary leading to different disposition of the isomers.

As a consequence, regulatory agencies (e.g. FDA) state that: "isomers should be treated as separate drugs and developed accordingly. There is no reason to consider developing mixtures of geometric isomers or diastereoisomers unless they fortuitously represent a reasonable fixed dose combination. Even in that case, whether the optimal ratio of the two isomers is the ratio produced by a synthesis should be critically examined".

Thus, efforts to obtain pure isomers can solve the problems related to the study and development of mixtures of isomers.

SUMMARY OF THE INVENTION

It has now been found that 3-aminooxime derivatives of 2- and/or 4-substituted androstanes and androstenes, optionally 5- and/or 6- and/or 7-substituted, meet the needs of providing drugs with high isomeric purity and a better therapeutic ratio and/or longer duration of action. Some of these compounds come from the modification of the compounds disclosed in EP 0 825 197 and *J. Med. Chem.* 2003, 64, 3644-3654, leading to unexpected pharmacological properties, namely higher potency, when correlated to their structure.

The compounds of the present invention have the general formula (I):

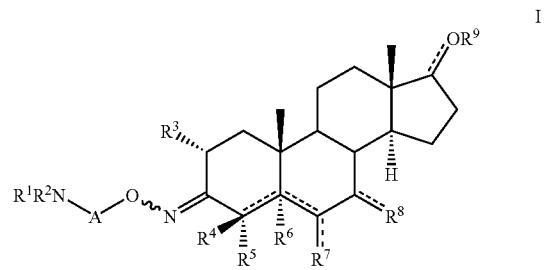

wherein:

A is a $C_1$-$C_6$ straight or branched alkylene or a $C_3$-$C_6$ cycloalkylene;

$R^1$ and $R^2$, which can be the same or different, are H, $C_1$-$C_6$ alkyl, phenyl-$C_1$-$C_4$ alkyl or $R^1$ and $R^2$ can be taken together with the nitrogen atom to which they are attached to form an unsubstituted or substituted saturated or unsaturated mono heterocyclic 4-, 5- or 6-membered ring optionally containing another heteroatom selected from the group consisting of oxygen, sulphur or nitrogen, and $R^1$ and $R^2$ can be optionally substituted by one or more hydroxy, methoxy, or ethoxy groups;

when $R^1$ is an alkyl group, $R^1$ and A can be taken together with the nitrogen atom to form an unsubstituted or substituted saturated or unsaturated mono heterocyclic 4-, 5- or 6-membered ring;

$R^3$ is hydrogen, hydroxy, fluoro, chloro or bromo;

when the symbol $=\!=$ in position 4 represents a single bond $R^4$ is hydrogen, fluoro, chloro, bromo, $C_1$-$C_6$ alkyl or hydroxy and $R^5$ is hydrogen, fluoro, chloro, bromo, methyl, ethyl or hydroxy;

$R^4$ and $R^5$, when the symbol $=\!=$ in position 4 represents a single bond, can be taken together with the carbon atom that they are linked to, to form a spirocyclopropane or spirocyclopentane ring;

when the symbol $=\!=$ in position 4 represents a double bond $R^4$ is fluoro, chloro, bromo, $C_1$-$C_6$ alkyl or hydroxy and $R^5$ is not present;

$R^6$ is H, or $OR^{10}$ or is absent when the symbol $=\!=$ in positions 4 or 5 represents a double bond;

$R^5$ and $R^6$, when the symbols $=\!=$ in positions 4 and 5 represent single bonds, can be taken together to form an oxirane or a cyclopropane ring;

when the bond $=\!=$ linking the carbon atom in position 6 of the androstane skeleton with $R^7$ is a double bond, $R^7$ is O, with the meaning of a keto group, or $N\!\sim\!OR^{11}$ or $CR^{12}R^{13}$;

when the bond $=\!=$ linking the carbon atom in position 7 of the androstane skeleton with $R^8$ is a double bond, $R^8$ is O, with the meaning of a keto group, or $N\!\sim\!OR^{11}$ or $CR^{12}R^{13}$;

when the bond $=\!=$ linking the carbon atom in position 6 of the androstane skeleton with $R^7$ is a single bond, $R^7$ is H, $C_1$-$C_6$ alkyl group, $OR^{14}$, vinyl, ethynyl, CHO, $COOR^{15}$, $ONO_2$, NHCHO, spirocyclopropane, spirooxirane, where the alkyl group can be optionally substituted by one or more hydroxy, methoxy or ethoxy;

$R^6$ and $R^7$, when the symbols $=\!=$ in positions 4, 5 and 6 represent single bonds, can be taken together to form an oxirane or cyclopropane ring;

when the bond $=\!=$ linking the carbon atom in position 7 of the androstane skeleton with $R^8$ is a single bond, $R^8$ is H, $C_1$-$C_6$ alkyl group, $OR^{14}$, vinyl, ethynyl, CHO, $COOR^{15}$, $ONO_2$, NHCHO, spirocyclopropane, spirooxirane, where the alkyl group can be optionally substituted by one or more hydroxy, methoxy or ethoxy;

$R^9$ is H, $C_1$-$C_6$ alkyl group or $C_2$-$C_7$ alkylcarbonyl group, when the bond $=\!=$ in position 17 of the androstane skeleton is a single bond, and when the bond $=\!=$ in position 17 is a double bond $R^9$ is not present;

$R^{10}$ is H, $C_1$-$C_6$ alkyl or $C_2$-$C_7$ alkylcarbonyl group;

$R^{11}$ is H, $C_1$-$C_6$ alkyl or $C_2$-$C_7$ alkylcarbonyl group;

$R^{12}$ and $R^{13}$, which can be the same or different, are H, $C_1$-$C_6$ alkyl or F;

$R^{14}$ is H, $C_1$-$C_6$ alkyl or $C_2$-$C_7$ alkylcarbonyl group;

$R^{15}$ is H or $C_1$-$C_6$ alkyl;

$R^{10}$, $R^{11}$, $R^{12}$, $R^{13}$, $R^{14}$, and $R^{15}$, when present in the same compound in different positions, can be the same or different;

the symbol $\sim$ represents an E or Z diastereoisomer;

the symbol $=\!=$ in positions 4, 5, 6, 7, and 17 represents, independently, a single or double bond, and when it is a single exocyclic bond in positions 6, 7, or 17, it can assume an α or a β orientation;

with the following provisos:

when $R^4$ is H and $R^5$ is methyl, both $R^7$ and $R^9$ do not have the meaning of keto groups;

when $R^4$ is hydroxy, $R^5$ is not hydroxy, fluoro, bromo, and chloro and viceversa;

that $R^3$, $R^4$ and $R^5$ are not hydrogen at the same time.

Where the compounds of formula (I) can exhibit tautomerism, the formula is intended to cover all tautomers, the metabolites and the metabolic precursors of compound of formula (I).

Also the pharmaceutical acceptable salts are included in the scope of the invention. Pharmaceutical acceptable salts are salts which retain the biological activity of the base and are derived from such known pharmacologically acceptable acids such as, e. g., hydrochloric, hydrobromic, sulfuric, phosphoric, nitric, fumaric, succinic, oxalic, malic, tartaric, maleic, citric, methanesulfonic or benzoic acid and others commonly used in the art.

The $C_1$-$C_6$ alkyl groups may be branched or straight chains or cyclic groups, e.g. methyl, ethyl, n-propyl, i-propyl, n-butyl, t-butyl, cyclopentyl or cyclohexyl. The $C_1$-$C_6$ alkylenic groups may be branched or straight chains or cyclic groups, e.g. methylene, ethylene, trimethylene, propylene, tetramethylene, dimethylethylene, cyclopropylene, cyclobutylene, cyclopentylene or cyclohexylene.

When $R^1$ and A are taken together with the nitrogen atom to form an unsubstituted or substituted saturated or unsaturated mono heterocyclic 4-, 5- or 6-membered ring, the heterocycles preferably are 3-pyrrolidinyl, 3-azetidinyl, 4-piperidinyl or 3-piperidinyl.

The $C_2$-$C_7$ alkylcarbonyl groups may be branched, straight or cyclic chains and preferably are acetyl, propionyl, butyryl, pivaloyl, cyclopentane-carbonyl or benzoyl.

A $C_4$-$C_{14}$ alkoxycarbonyl anhydride groups may contain branched, straight or cyclic chains and preferably are acetic anhydride, propionic anhydride, benzoic anhydride, benzyloxycarbonyl anhydride and the like.

The bond $=\!=$ in position "x" represents a single or a double bond unless otherwise specified, linking the carbon atom in position x to the carbon atom in position "x+1" of the androstane skeleton or to its substituent. The latter case refers to carbon atoms in positions 6, 7 and 17 only.

In the context of the present invention, metabolite and metabolic precursors mean active metabolite and metabolic precursors, namely a compound of formula (I), which has been transformed by a metabolic reaction, but substantially maintains or increases the pharmacological activity.

Examples of metabolites or metabolic precursors are hydroxylated, carboxylated, sulfonated, glycosylated, glucuronated, methylated or demethylated, oxidated or reduced derivatives of the compounds of formula (I). Some compounds of formula (I) can also be prodrugs of the active forms.

Further object of the present invention is the use of said compounds of general formula (I) in the preparation of a medicament useful in the treatment of cardiovascular diseases such as heart failure and hypertension.

DETAILED DESCRIPTION OF THE INVENTION

Preferred examples of specific compounds (I) of the present invention are:

E 3-(2-aminoethoxyimino)-4,4-dimethylandrostan-17-one,

E 3-(2-aminoethoxyimino)-4,4-dimethylandrost-5-en-17-one,

E 3-(2-aminoethoxyimino)-4,4-dimethylandrostan-17β-ol,

E 3-(2-aminoethoxyimino)-4,4-dimethylandrost-5-en-17β-ol,

E 3-(2-aminoethoxyimino)-4,4-dimethylandrostan-6,17-dione,

E 3-(2-aminoethoxyimino)-4,4-dimethyl-5α-hydroxyandrostan-6,17-dione,
E 3-(2-aminoethoxyimino)-4-spirocyclopropaneandrostan-17-one,
E 3-(2-aminoethoxyimino)-4-spirocyclopropaneandrost-5-en-17-one,
E 3-(2-aminoethoxyimino)-4-spirocyclopropaneandrostan-17β-ol,
E 3-(2-aminoethoxyimino)-4-spirocyclopropaneandrost-5-en-17β-ol,
E 3-(2-aminoethoxyimino)-4-spirocyclopropaneandrostan-6,17-dione,
E 3-(2-aminoethoxyimino)-4β-ethylandrostan-17-one,
E 3-(2-aminoethoxyimino)-4β-ethylandrostan-6,17-dione,
E 3-(2-aminoethoxyimino)-4β-ethyl-6α-hydroxyandrostan-17-one,
E 3-(2-aminoethoxyimino)-4β-ethyl-6α-hydroxyandrostan-17-one,
E 3-(2-aminoethoxyimino)-4β-ethylandrostan-6β,17β-diol,
E 3-(2-aminoethoxyimino)-4α-ethylandrostan-17β-ol,
E 3-(2-aminoethoxyimino)-4α-ethylandrostan-17-one,
E 3-(2-aminoethoxyimino)-4α-fluoroandrostan-17-one,
E 3-(2-aminoethoxyimino)-4α-fluoroandrostan-17β-ol,
E 3-(2-aminoethoxyimino)-2α-fluoroandrostan-17-one,
E 3-(2-aminoethoxyimino)-2α-fluoroandrostan-17β-ol,
E 3-(2-aminoethoxyimino)-2α-fluoro-17β-hydroxyandrostan-6-one,
3-(E)-(2-aminoethoxyimino)-2α-fluoro-6-(E)-hydroxyiminoandrostan-17β-ol,
3-(E)-(2-aminoethoxyimino)-2α-fluoro-6-(E)-methoxyiminoandrostan-17β-ol,
3-(E)-(2-aminoethoxyimino)-2α-fluoro-6-(E)-hydroxyiminoandrostan-17-one,
3-(E)-(2-aminoethoxyimino)-2α-fluoro-6-(E)-methoxyiminoandrostan-17-one,
E 3-(2-aminoethoxyimino)-4-spirocyclopentaneandrostan-17-one,
E 3-(2-aminoethoxyimino)-4-spirocyclopentaneandrostan-17β-ol,
E 3-(2-aminoethoxyimino)-4-spirocyclopentaneandrostan-6α,17β-diol,
and the corresponding 3-(3-aminopropoxyimino), 3-(2-N-methylaminoethoxyimino), 3-(3-N-methylaminopropoxyimino), 3-(1-amino-2-methyl-2-propoxyimino), 3-(3-(R)-pyrrolidinyloxyimino), 3-(3-(S)-pyrrolidinyloxyimino), 3-(3-azetidinyloxyimino), 3-(4-piperidinyloxyimino) and (E)-3-(2-dimethylaminoethoxyimino) derivatives.

The invention furthermore provides a process for the preparation of compounds of general formula (I) by reacting compounds of general formula (II)

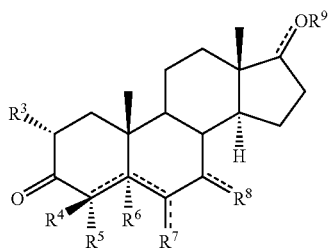

II where the symbols $R^3$, $R^4$, $R^5$, $R^6$, $R^7$, $R^8$, $R^9$, and $=\!=\!=$ have the meanings defined above with compounds of general formula (III), $$R^1R^2N\text{-}A\text{-}ONH_2 \qquad (III)$$

where $R^2$, $R^1$, and A have the meanings defined above, in the form of the free base or of a salt, such as, for example, dihydrochloride, in a solvent such as dioxane, tetrahydrofuran, 1,2-dimethoxyethane, methanol, ethanol, N,N-dimethylformamide, pyridine, water or their mixtures, at a temperature ranging from 0° C. to the reflux temperature. The reaction may be carried out in the presence of a base, such as sodium or potassium hydroxide, sodium or potassium carbonate, sodium or potassium hydrogen carbonate, or of an acid, such as hydrochloric acid, hydrobromic acid, acetic acid, or of a salt, such as sodium or potassium acetate, sodium or potassium phosphate, disodium or dipotassium hydrogen phosphate, sodium or potassium dihydrogen phosphate.

Compounds of general formula (I) where the symbols A, $R^1$, $R^2$, $R^3$, $R^4$, $R^5$, $R^6$, $R^7$, $R^8$, $R^9$ have the meanings defined above and at least one of $=\!=\!=$ represents a single bond, can be obtained by reduction of the corresponding compounds of general formula (I) where the symbol $=\!=\!=$ represents a double bond, by catalytic hydrogenation, either with hydrogen gas or in hydrogen transfer conditions, in the presence of a metal catalyst, such as Pd/C, PtO$_2$, Pt, Pt/C or Raney Nickel. As a hydrogen transfer reagent, ammonium formate, sodium hypophosphite or cyclohexadiene can be used. The reaction can be carried out in a solvent, such as, for example, ethanol, methanol, ethyl acetate, dioxane, tetrahydrofuran, acetic acid, N,N-dimethylformamide, water or their mixtures, at a temperature ranging from 0° C. and the reflux temperature, at a pressure ranging from atmospheric pressure to 10 atm. According to the substrate and the conditions used, the hydrogenation can selectively affect one or more double bonds.

Compounds of general formula (I) where the symbols A, $R^1$, $R^2$, $R^3$, $R^4$, $R^5$, $R^6$, $R^9$, and $=\!=\!=$ have the meanings defined above, $R^7$ is not N⁓OR$^{11}$ and $R^8$ is N$=\!=$OR$^{11}$ when the bond ⁓ linking the carbon atom in position 6 with $R^7$ can be a single or a double bond and the bond linking the carbon atom in position 7 of the androstane skeleton with $R^8$ is a double bond, can be obtained from the corresponding compounds of general formula (I) where $R^8$ is O, with the meaning of a keto group, with one of the methods reported in literature for such reactions, such as, for example, by reaction with compounds of general formula H$_2$NOR$^{11}$ where $R^{11}$ has the meanings defined above, in the reaction conditions described above for the reaction of compounds (II) with compounds (III).

Compounds of general formula (I) where the symbols A, $R^1$, $R^2$, $R^3$, $R^4$, $R^5$, $R^6$, $R^9$, and $=\!=\!=$ have the meanings defined above, $R^7$ is N⁓OR$^{11}$ and $R^8$ is not N⁓OR$^{11}$ when the carbon atom in position 7 of the androstane skeleton with $R^8$ can be single or double bond, can be obtained from the corresponding compounds of general formula (I) where $R^7$ is O, with the meaning of a keto group, with one of the methods reported in literature, such as, for example, by reaction with compounds of general formula H$_2$NOR$^{11}$, using the reaction conditions described above for the reaction of compounds (II) with compounds (III).

Compounds of general formula (I) where the symbols A, $R^1$, $R^2$, $R^3$, $R^4$, $R^5$, $R^6$, $R^9$, and $=\!=\!=$ have the meanings defined above, $R^7$ and $R^8$ are N⁓OR$^{11}$ can be obtained from the corresponding compounds of general formula (I) where $R^7$ and $R^8$ are O, with the meaning of keto groups, with one of the methods reported in literature for such reactions, such as, for example, by reaction with compounds of general formula H₂NOR¹¹, in the reaction conditions described above for the reaction of compounds (II) with compounds (III).

Compounds of general formula (I) where the symbols A, R¹, R², R³, R⁴, R⁵, R⁶, R⁹, and ═ have the meanings defined above, and R⁷ is not CR¹²R¹³ and R⁸ is CR¹²R¹³ when the bond ═ linking the carbon atom in position 6 with R⁷ can be a single or a double bond, can be obtained from the corresponding compounds of general formula (I) where R⁸ is O, with the meaning of a keto group, with one of the methods reported in literature for such reactions, such as, for example, by reaction with compounds of general formula (IV) or (V),

  (IV)

  (V)

where R¹² and R¹³ are as defined above, R¹⁶ is a C₁-C₆ alkyl or aryl, and Hal is a halogen, such as, for example, chloro, bromo or iodo. The reaction with compounds of general formula (IV) or (V) can be carried out in a solvent such as diethyl ether, dioxane, tetrahydrofuran, 1,2-dimethoxyethane, toluene, N,N-dimethylformamide, dimethylsulfoxide, n-pentane or their mixtures, at a temperature ranging from −78° C. to the reflux temperature. The reaction is carried out in the presence of a base, such as, for example, sodium or potassium hydride, sodium or potassium methoxide, sodium or potassium tert-butoxide. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogen sulfate, at a temperature ranging from 0° C. to the reflux temperature of the mixture. The reaction with compounds of general formula (V) can be carried out also in water or in a mixture of the above mentioned solvents with water, at a temperature ranging from 0° C. to the reflux temperature. These reactions can be carried out in the presence of a base, such as, for example, sodium or potassium hydroxide, sodium or potassium hydrogen carbonate, sodium or potassium carbonate, triethylamine, diisopropylethylamine, optionally in the presence of a salt, such as lithium chloride.

Compounds of general formula (I) where the symbols A, R¹, R², R³, R⁴, R⁵, R⁶, R⁹, and ═ have the meanings defined above, and R⁷ is CR¹²R¹³ and R⁸ is not CR¹²R¹³ when the bond ═ linking the carbon atom in position 7 of the androstane skeleton with R⁸ is a single or a double bond, can be obtained from the corresponding compounds of general formula (I) where R⁷ is O, with the meaning of a keto group, by reaction with compounds of general formula (IV) or (V), as defined above, using the reaction conditions described above.

Compounds of general formula (I) where the symbols A, R¹, R², R³, R⁴, R⁵, R⁶, R⁹, and ═ have the meanings defined above, and R⁷ and R⁸ are CR¹²R¹³, can be obtained from the corresponding compounds of general formula (I) where R⁷ and R⁸ are both O, with the meaning of keto groups, for example, by reaction with compounds of general formula (IV) or (V), as defined above, using the reaction conditions described above.

Compounds of general formula (I) where the symbols A, R¹, R², R³, R⁴, R⁵, R⁶, R⁹, and ═ have the meanings defined above, and at least one of R⁷ and R⁸, is hydroxymethyl, can be obtained from the corresponding compounds of general formula (I) where at least one of R⁷ and R⁸ is CR¹²R¹³, where R¹² and R¹³ are hydrogens, with one of the methods reported in literature for such reactions, such as, for example, by reaction with a borane, such as, for example, diborane, or its complexes with dimethylamine or dimethylsulfide, 9-borabicyclononane, diisopino-camphenylborane, diisoamylborane, in an ethereal solvent, such as, for example, diethyl ether, tetrahydrofuran, dioxane, 1,2-dimethoxyethane, followed by treatment with an alkaline aqueous hydrogen peroxide solution or sodium perborate.

With the same methods, also compounds of general formula (I) where the symbols A, R¹, R², R³, R⁴, R⁵, R⁶, R⁹, and ═ have the meanings defined above, and at least one of R⁷ and R⁸, is hydroxyethyl, can be obtained from the corresponding compounds of general formula (I) where at least one of R⁷ and R⁸ is vinyl. Compounds of general formula (I) where at least one of R⁷ and R⁸ is vinyl, can be obtained by reaction of compounds of general formula (I) where at least one of R⁷ and R⁸ is CHO, with methyltriphenylphosphonium chloride or bromide or iodide by using the same reaction conditions described above involving compounds of general formula (IV) or (V).

Compounds of general formula (I) where the symbols A, R¹, R², R³, R⁴, R⁵, R⁶, R⁹, and ═ have the meanings defined above, and at least one of R⁷ and R⁸ is O, with the meaning of keto groups, can be obtained from the corresponding compounds of general formula (I) where at least one of R⁷ and R⁸ is hydroxy, with one of the reagents reported in literature for such oxidations, such as, for example, iodoxybenzoic acid, Dess-Martin periodinane, oxalyl chloride and triethylamine and DMSO, CrO₃ in pyridine or in sulfuric acid and acetone, pyridinium chlorochromate or pyridinium dichromate.

By using the same oxidising reactions reported above, compounds of general formula (I) where R⁹ is absent can be obtained by treatment of compounds of general formula (I) where R⁹ is hydrogen.

Compounds of general formula (I) where the symbols A, R¹, R², R³, R⁴, R⁵, R⁶, R⁹, and ═ have the meanings defined above, and at least one of R⁷ and R⁸ is OR¹⁴, R¹⁴ being hydrogen, can be obtained from the corresponding compounds of general formula (I) where at least one of R⁷ and R⁸ is O, with the meaning of keto group, by reduction with a complex hydride, such as, for example, NaBH₄, optionally in the presence of a Lewis acid such as, for example CeCl₃, in an alcoholic or ethereal solvent, or LiAlH₄ in an ethereal solvent, LiBH₄ or LiAl(tBuO)₃H or with a metal, such as, for example sodium, in an alcoholic solvent, at a temperature ranging from 0° C. to the reflux temperature of the mixture.

By using the same reducing reactions reported above, compounds of general formula (I) where R⁹ is hydrogen can be obtained by treatment of compounds of general formula (I) where R⁹ is absent.

Compounds of general formula (I), where R⁹ is C₁-C₆ alkyl, can be prepared from compounds of general formula (I), where R⁹ is hydrogen by treatment with a base, such as, for example, sodium or potassium hydride, sodium or potassium methoxide, sodium or potassium tert-butoxide, lithium diisopropylamide in a solvent such as diethyl ether, dioxane, tetrahydrofuran, 1,2-dimethoxyethane, toluene, dimethylsulfoxide or their mixtures, at a temperature ranging from −78° C. to the reflux temperature, followed by quenching with a C₁-C₆ alkyl-LG, where LG is a leaving group, such as, for example, chloro, bromo, iodo, mesyloxy, p-toluenesulfonyloxy, trifluoromethanesulfonyloxy, at a temperature ranging from −78° C. to the reflux temperature. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. to the reflux temperature of the mixture.

Compounds of general formula (I), where $R^9$ is $C_2$-$C_7$ alkylcarbonyl, can be prepared from compounds of general formula (I), where $R^9$ is hydrogen by reaction with an appropriate $C_2$-$C_7$ alkylcarbonyl halide or $C_4$-$C_{14}$ alkylcarbonyl anhydride in a solvent such as diethyl ether, dioxane, tetrahydrofuran, 1,2-dimethoxyethane, toluene, N,N-dimethylformamide, dimethylsulfoxide, dichloromethane, pyridine or their mixtures, at a temperature ranging from −78° C. to the reflux temperature, optionally in the presence of a base, such as, for example, triethylamine, pyridine, 4-dimethylaminopyridine. The same reaction can be carried out also with the corresponding $C_2$-$C_7$ carboxylic acid in a solvent such as diethyl ether, dioxane, tetrahydrofuran, 1,2-dimethoxyethane, toluene, acetone, ethyl acetate, dichloromethane, chloroform, N,N-dimethylformamide, dimethylsulfoxide, water, or their mixtures, at a temperature ranging from −30° C. to the reflux temperature, in the presence of a condensing reagent such as, N,N'-dicyclohexylcarbodiimide, N-ethyl-N'-(3-dimethylaminopropyl)-carbodiimide hydrochloride.

Compounds of general formula (II), as defined above, can be prepared starting from known compounds with proper functionality in the different positions, already reported in the literature or from commercially available compounds, such as for example, testosterone, following the general procedures listed below. 4-methyltestosterone and 17β-hydroxy-4,4-dimethylandrost-5-en-3-one have been reported by Atwater et al., *J. Am. Chem. Soc.*, 1957, 5315; 17β-hydroxy-4,4-dimethylandrostan-3-one has been reported by Rosenkranz et al., *J. Org. Chem.*, 1957; 602; 4-(spirocyclopropane)-17β-hydroxyandrost-5-ene-3-one has been reported by Youngdale in U.S. Pat. No. 3,793,308 (1974); 2α-fluorodihydrotestosterone has been reported by Nakanishi et al., *J. Am. Chem. Soc.*, 1959, 5259; 4-spirocyclopentane-17β-hydroxyandrost-5-ene-3-one has been reported by Rizvi S. Q. A. et al., *J. Org. Chem.*, 1974, 1127; 6-methoxy-17β-hydroxyandrosta-4,6-dien-3-one has been reported by Sollman P. B. et al., *J. Org. Chem.*, 1961, 4180 and 4-isopropyl-17β-hydroxyandrost-4-en-3-one has been reported in WO2002000681.

Compounds of general formula (II), where $R^4$, $R^5$, $R^6$, $R^7$, $R^8$, $R^9$ have the meanings defined above, the symbol ═ in position 4 represents a single bond, the other symbols ═ have the meanings defined above and $R^3$ is fluoro, can be obtained from compounds of general formula (II) where $R^3$ is hydrogen, with one of the methods reported in literature for such reactions, such as for example, reaction of the corresponding 2-enol-3-ester with $CF_3OF$, 2-enol-3-ether with $FClO_3$, or 2-enol-3-silylether with N-fluoropyridinium triflate at a temperature ranging from −78° C. to the reflux temperature.

Compounds of general formula (II), where $R^4$, $R^5$, $R^6$, $R^7$, $R^8$, $R^9$ have the meanings defined above, the symbol ═ in position 4 represents a single bond, the other symbols ═ have the meanings defined above and $R^3$ is chloro, can be obtained from compounds of general formula (II) where $R^3$ is hydrogen, with one of the methods reported in literature, such as, for example, reaction with t-BuOCl or acetyl chloride and $MnO_2$ in acetic acid at a temperature ranging from −78° C. to the reflux temperature.

Compounds of general formula (II), where $R^4$, $R^5$, $R^6$, $R^7$, $R^8$, $R^9$ have the meanings defined above, the symbol ═ in position 4 represents a single bond, the other symbols ═ have the meanings defined above and $R^3$ is bromo, can be obtained from compounds of general formula (II) where $R^3$ is hydrogen, with one of the methods reported in literature, such as, for example, reaction with bromine in acetic acid, pyridinium bromide perbromine in acetic acid, PhSeBr in EtOAc, or from a corresponding 2-enol-3-ether with NBS in t-BuOH in the presence of an acid, such as $H_2SO_4$, at a temperature ranging from −78° C. to the reflux temperature.

Compounds of general formula (II), where $R^4$, $R^5$, $R^6$, $R^7$, $R^8$, $R^9$ have the meanings defined above, the symbols ═ in positions 4 and 5 are single bonds, the other symbols ═ have the meanings defined above and $R^3$ is hydroxy, can be obtained from compounds of general formula (II) substituted with a 2α- or 2β-bromo, with one of the methods reported in literature, such as, for example, reaction with a base, such as $K_2CO_3$, $Na_2CO_3$, NaOH, KOH, in water and an organic solvent, or tertrabutylammonium hydrogensulphate in an organic solvent, or from compounds of general formula (II) where $R^3$ is hydrogen with $Pb(OAc)_4$, optionally in the presence of a Lewis acid, such as $BF_3$, or from the reaction of a compound of general formula (II) via its corresponding 2-enol-3-silylether, with m-chloroperbenzoic acid followed by hydrolysis with an acid or fluoride ion, at a temperature ranging from −78° C. to the reflux temperature.

Compounds of general formula (II), where $R^3$, $R^5$, $R^6$, $R^7$, $R^8$, $R^9$ have the meanings defined above, the symbol ═ in position 4 represents a double bond, the other symbols ═ have the meanings defined above, $R^4$ is fluoro and $R^5$ is not present, can be obtained from compounds of general formula (II) where $R^4$ is $Bu_3Sn$, with one of the methods reported in literature for such reactions, such as for example, by reaction with $Cs_2CO_3$ and fluorine, at a temperature ranging from −78° C. to the reflux temperature of the mixture. Compounds where $R^4$ is n-$Bu_3Sn$ can be obtained from the corresponding compounds of general formula (II) where $R^4$ is bromo.

Compounds of general formula (II), where $R^3$, $R^5$, $R^6$, $R^7$, $R^8$, $R^9$ have the meanings defined above, the symbol ═ in position 4 is a double bond, the other symbols ═ have the meanings defined above, $R^4$ is chloro and $R^5$ is not present, can be obtained from compounds of general formula (II) where $R^4$ is hydrogen, with one of the methods reported in literature, such as, for example, by reaction with $SOCl_2$ in pyridine, or from compounds of general formula (II) where $R^4$ is hydrogen, $R^5$ and $R^6$ are taken together to form an oxirane ring, with HCl or benzoyl chloride and $YCl_3$, at a temperature ranging from −78° C. to the reflux temperature.

Compounds of general formula (II), where $R^3$, $R^5$, $R^6$, $R^7$, $R^8$, $R^9$ have the meanings defined above, the symbol ═ in position 4 represents a double bond, the other symbols ═ have the meanings defined above, $R^4$ is bromo and $R^5$ is not present, can be obtained from compounds of general formula (II) where $R^4$ is hydrogen, $R^5$ and $R^6$ are taken together to form an oxirane ring, with one of the methods reported in literature, such as, for example, by reaction with bromine and an organic base, such as pyridine or s-collidine in acetic acid, at a temperature ranging from −78° C. to the reflux temperature.

Compounds of general formula (II), where $R^3$, $R^5$, $R^6$, $R^7$, $R^8$, $R^9$ have the meanings defined above, the symbol ═ in position 4 represents a double bond, the other symbols ═ have the meanings defined above, $R^4$ is hydroxy and $R^5$ is not present, can be obtained from compounds of general formula (II) where $R^4$ is hydrogen, $R^5$ and $R^6$ are taken together to form an oxirane ring, with one of the methods reported in literature, such as, for example, reaction with a strong acid, such as HCl or $H_2SO_4$, or with a base, such as, NaOH, KOH, followed by an acid, and an organic solvent, at a temperature ranging from −78° C. to the reflux temperature.

Compounds of general formula (II), where $R^3$, $R^6$, $R^7$, $R^8$, $R^9$ have the meanings defined above, the symbol ═ in position 5 represents a double bond, the other symbols ═ have the meanings defined above and $R^4$ or $R^5$ is fluoro, can be obtained from compounds of general formula (II) where $R^4$ and $R^5$ are hydrogen, or $R^4$ and $R^5$ are hydrogen and $C_1$-$C_6$ alkyl respectively, with one of the methods reported in literature for such reactions, such as for example, reaction of the corresponding 3,5-dienol-3-silyether with N-fluoropyridinium triflate, 3,5-dien-3-amine with $FClO_3$, at a temperature ranging from $-78°$ C. to the reflux temperature of the mixture; or from compounds of general formula (II) where $R^4$ and $R^5$ are hydrogen, the symbol $=\!=$ in position 5 is a double bond, with one of the methods reported in literature for such reactions, such as for example, by reaction with a strong base, such as LDA, KH or NaH, followed by addition of $FClO_3$ or N-fluorobis(phenylsulfonyl)amine, at a temperature ranging from $-78°$ C. to the reflux temperature; or from compounds of general formula (II) where $R^4$ and $R^5$ are hydrogen, or $R^4$ and $R^5$ are hydrogen and $C_1$-$C_6$ alkyl respectively, with one of the methods reported in literature for such reactions, such as for example, by reaction of the corresponding 3-keto derivative with 1-chloromethyl-4-fluoro-1,4-diazoniabicyclo[2.2.2]octane bis(tetrafluoroborate) or SELECTFLUOR® in a solvent, such as acetonitrile, isopropanol, at a temperature ranging from $0°$ C. to the reflux temperature of the mixture.

Compounds of general formula (II), where $R^3$, $R^6$, $R^7$, $R^8$, $R^9$ have the meanings defined above, the symbols $=\!=$ in position 4 and 5 are single bonds, the other symbols $=\!=$ have the meanings defined above, one of $R^4$ and $R^5$ is fluoro the other being $C_1$-$C_6$ alkyl or H, can be obtained from compounds of general formula (II) where one of $R^4$ and $R^5$ is H the other being H or $C_1$-$C_6$ alkyl, with one of the methods reported in literature for such reactions, such as, for example, reaction of the corresponding 3-enolsilylether with N-fluoropyridinium triflate, 3-enamine with $FClO_3$, at a temperature ranging from $-78°$ C. to the reflux temperature.

Compounds of general formula (II), where $R^3$, $R^7$, $R^8$, $R^9$ have the meanings defined above, $R^6$ is hydroxy, the symbols $=\!=$ have the meanings defined above and $R^4$ or $R^5$ is fluoro, can be obtained from compounds of general formula (II) where $R^4$ is hydrogen, $R^5$ and $R^6$ taken together form an oxirane ring, with one of the methods reported in literature for such reactions, such as, for example, reaction with n-Bu$_4$NF, KF, CsF at a temperature ranging from $-78°$ C. to the reflux temperature.

Compounds of general formula (II), where $R^3$, $R^6$, $R^7$, $R^8$, $R^9$ have the meanings defined above, the symbols $=\!=$ in position 4 and 5 represent single bonds, the other symbols $=\!=$ have the meanings defined above, $R^4$ or $R^5$ is chloro, or one of $R^4$ and $R^5$ is H the other being $C_1$-$C_6$ alkyl can be obtained from compounds of general formula (II) where $R^4$ or $R^5$ are hydrogen, or one of $R^4$ or $R^5$ is H the other being $C_1$-$C_6$ alkyl, with one of the methods reported in literature for such reactions, such as, for example, reaction with t-BuOCl, optionally in the presence of HCl, at a temperature ranging from $-78°$ C. to the reflux temperature.

Compounds of general formula (II), where $R^3$, $R^6$, $R^7$, $R^8$, $R^9$ have the meanings defined above, the symbols $=\!=$ in position 4 and 5 are single bonds, the other symbols $=\!=$ have the meanings defined above, $R^4$ or $R^5$ is bromo, or one of $R^4$ and $R^5$ is H the other being $C_1$-$C_6$ alkyl can be obtained from compounds of general formula (II) where $R^4$ or $R^5$ are hydrogen, or one of $R^4$ and $R^5$ is H the other being $C_1$-$C_6$ alkyl with one of the methods reported in literature for such reactions, such as for example, reaction with bromine in acetic acid, at a temperature ranging from $-78°$ C. to the reflux temperature.

Compounds of general formula (II), where $R^3$, $R^6$, $R^7$, $R^8$, $R^9$ have the meanings defined above, the symbol $=\!=$ in position 5 represents a double bond, the other symbols $=\!=$ have the meanings defined above and $R^4$ or $R^5$ is hydroxy or one of $R^4$ and $R^5$ is OH the other being $C_1$-$C_6$ alkyl can be obtained from compounds of general formula (II) where $R^4$ and $R^5$ are hydrogen, or one of $R^4$ and $R^5$ is H the other being $C_1$-$C_6$ alkyl with one of the methods reported in literature for such reactions, such as for example, with Pb(OAc)$_4$ in AcOH, followed by hydrolysis of the intermediate acetate, at a temperature ranging from $0°$ C. to the reflux temperature.

Compounds of general formula (II), where $R^3$, $R^6$, $R^7$, $R^8$, $R^9$ have the meanings defined above, the symbols $=\!=$ in position 4 and 5 are single bonds, the other symbols $=\!=$ have the meanings defined above, $R^4$ is hydroxy and $R^5$ is H or $C_1$-$C_6$ alkyl, can be obtained from the corresponding compounds of general formula (II) where $R^4$ is hydrogen or $C_1$-$C_6$ alkyl, the symbol $=\!=$ in position 4 is double bond, with one of the methods reported in literature for such reactions, such as for example, with a borane like diborane, or its complexes with tetrahydrofuran, dimethylamine or dimethylsulfide, 9-borabicyclononane, diisopinocamphenylborane, diisoamylborane, in an ethereal solvent like diethyl ether, tetrahydrofuran, dioxane, 1,2-dimethoxyethane, followed by treatment with an alkaline aqueous hydrogen peroxide solution or sodium perborate.

Compounds of general formula (II), where $R^3$, $R^6$, $R^7$, $R^8$, $R^9$ and the symbols $=\!=$ have the meanings defined above, $R^4$ is $C_1$-$C_6$ alkyl, the bond $=\!=$ in position 4 represents a double bond can be obtained from compounds of general formula (II) where $R^4$ is hydrogen, the bond $=\!=$ in position 4 is a double bond, with one of the reagents reported in literature for such reactions, such as for example by treatment with a base, such as for example, sodium or potassium hydride, sodium or potassium methoxide, sodium or potassium tert-butoxide, lithium diisopropylamide, sodium amide, lithium amide in a solvent such as diethyl ether, dioxane, tetrahydrofuran, 1,2-dimethoxyethane, toluene, N,N-dimethylformamide, dimethylsulfoxide, t-BuOH, liquid ammonia or their mixtures, at a temperature ranging from $-78°$ C. to the reflux temperature, followed by quenching with a $C_1$-$C_6$ alkyl-LG, where LG is a leaving group, such as for example, chloro, bromo, iodo, mesyloxy, trifluoromethanesulfonyloxy, p-toluensulfonyloxy, at a temperature ranging from $-78°$ C. to the reflux temperature. The reaction can be carried out also in dichloromethane, chlorobenzene, toluene, hexane, and water or their mixture, in the presence of sodium or potassium hydroxide and a quaternary ammonium salt, such as for example, tetrabutylammonium chloride or bromide or iodide or hydrogen sulfate, at a temperature ranging from $0°$ C. to the reflux temperature.

Compounds of general formula (II), where $R^3$, $R^6$, $R^7$, $R^8$, $R^9$ and the symbols $=\!=$ have the meanings defined above, $R^4$ and $R^5$ being identical are $C_1$-$C_6$ alkyl, when the bond $=\!=$ in position 5 represents a double bond, can be obtained from compounds of general formula (II) where $R^4$ is hydrogen, when the bond $=\!=$ in position 4 is a double bond, with one of the methods reported above, using an excess of $C_1$-$C_6$ alkyl-LG.

Compounds of general formula (II), where $R^3$, $R^6$, $R^7$, $R^8$, $R^9$ and the symbols $=\!=$ have the meanings defined above, $R^4$ is $C_1$-$C_6$ alkyl and $R^5$ is methyl or ethyl, $R^4$ and $R^5$ are different alkyl groups, the bond $=\!=$ in position 5 is a double bond, can be obtained from compounds of general formula (II) where $R^4$ is $C_1$-$C_6$ alkyl, the bond $=\!=$ in position 4 represents a double bond, with one of the methods reported above, using methyl-LG or ethyl-LG, where LG is a leaving group, as defined above or from compounds of general formula (II) where $R^4$ is methyl or ethyl, the bond $=\!=$ in position 4 represents a double bond, with one of the methods reported above, using ethyl-LG or methyl-LG respectively.

Compounds of general formula (II), where $R^3$, $R^6$, $R^7$, $R^8$, $R^9$ and the symbols ═ have the meanings defined above, $R^4$ and $R^5$ are taken together with the meaning of spirocyclopropane, the bond ═ in position 5 represents a double bond, can be obtained from compounds of general formula (II) where $R^4$ is hydrogen and $R^5$ is not present, the bond ═ in position 4 represents a double bond, with one of the methods reported above, using 1,2-dibromoethane or 1,2-diiodoethane or 1,2-dichloroethane as the alkylating reagents.

Compounds of general formula (II), where $R^3$, $R^6$, $R^7$, $R^8$, $R^9$ and the symbols ═ have the meanings defined above, $R^4$ and $R^5$ are taken together with the meaning of spirocyclopentane, the bond ═ in position 5 represents a double bond, can be obtained from compounds of general formula (II) where $R^4$ is hydrogen and $R^5$ is not present, the bond ═ in position 4 represents a double bond, with one of the methods reported above, using 1,4-dihalobutane as the alkylating reagents, where the halogens can be bromo, chloro or iodo.

Compounds of general formula (II), where $R^3$, $R^6$, $R^7$, $R^8$, $R^9$ and the symbols ═ have the meanings defined above, $R^4$ and $R^5$ are taken together with the meaning of spirocyclopropane, can be obtained from the corresponding appropriately protected 3-hydroxy, 4-keto derivative by reaction with a methyltriphenylphosphonium halide in the same reaction conditions above described involving compounds of general formula (IV) or (V) to give the corresponding 4-methylene derivative and subsequent reaction of the latter with one of the reagents reported in literature for such reactions, such as for example, diiodomethane and diethyltin or tin-copper alloy.

Compounds of general formula (II), where $R^3$, $R^6$, $R^7$, $R^8$, $R^9$ and the symbols ═ have the meanings defined above, one of $R^4$ and $R^5$ is hydroxy the other being $C_1$-$C_6$ alkyl, can be obtained from the corresponding appropriately protected 3-hydroxy derivatives, 4-keto derivatives by reaction with a $C_1$-$C_6$ alkylMetY, where Met is a metal atom and Y is nothing, halogen or a different metal atom depending on the oxidation state of the Met metal atom, such as for example, Li, MgCl, MgBr, MgI, ZnCl, and CuLi, in an ethereal solvent at a temperature ranging from −78° C. to the reflux temperature.

Compounds of general formula (II), where $R^3$, $R^4$, $R^8$, $R^9$ and the symbols ═ have the meanings defined above, $R^5$ and $R^6$, or $R^6$ and $R^7$ are taken together to form an oxirane ring, can be obtained from compounds of general formula (II) where $R^5$ and $R^6$, or $R^6$ and $R^7$ are hydrogens, when the bond ═ in position 4 or in position 5 of the androstane skeleton represents a double bond, respectively, with one of the reagents reported in literature for such reactions, such as for example perbenzoic acid, m-chloroperbenzoic acid, magnesium perphthalate, perphthalic acid, peracetic acid or hydrogen peroxide and sodium hydroxide in acetonitrile.

Compounds of general formula (II), where $R^3$, $R^4$, $R^8$, $R^9$ and the symbols ═ have the meanings defined above, $R^5$ and $R^6$, or $R^6$ and $R^7$, are taken together to form a cyclopropane ring, can be obtained from compounds of general formula (II), where the bond ═ in position 4 or 5 represents a double bond respectively, with one of the reagents reported in literature for such reactions, such as for example diiodomethane and diethyltin or tin-copper alloy, trimethylsulfonium iodide and a strong base.

Compounds of general formula (II) where $R^3$, $R^7$, $R^8$, $R^9$ have the meanings defined above, one of $R^4$ and $R^5$ is hydrogen the other being H or $C_1$-$C_6$ alkyl, the symbols ═ have the meanings defined above, and $R^6$ is $OR^{10}$, with $R^{10}$ being hydrogen, can be obtained from compounds of general formula (II) where $R^4$ is H or $C_1$-$C_6$ alkyl, $R^5$ and $R^6$ taken together or $R^6$ and $R^7$ taken together form an oxirane ring, with one of the methods reported in literature for such reactions, such as for example, reduction with LiAlH$_4$, LiBH$_4$, Li($C_2H_5$)$_3$H in an ethereal solvent at a temperature ranging from 0° C. to the reflux temperature.

Compounds of general formula (II) where $R^3$, $R^4$, $R^5$, $R^6$, $R^8$, $R^9$ and ═ have the meanings defined above, and $R^7$ is $OR^{14}$, with $R^{14}$ being hydrogen, where the bonds ═ in positions 4, 5, 6 and 7, are single bonds, can be obtained from compounds of general formula (II) where the bond ═ in position 5 is a double bond and $R^7$ is hydrogen, with one of the methods reported in literature for such reactions, such as for example, by reaction with a borane like diborane, or its complexes with tetrahydrofuran, dimethylamine or dimethylsulfide, 9-borabicyclononane, diisopinocamphenylborane, diisoamylborane, in an ethereal solvent, such as for example, diethyl ether, tetrahydrofuran, dioxane, 1,2-dimethoxyethane, followed by treatment with an alkaline aqueous hydrogen peroxide solution or sodium perborate.

Compounds of general formula (II) where $R^3$, $R^4$, $R^5$, $R^8$, $R^9$ and ═ have the meanings defined above, and $R^6$ and $R^7$ are $OR^{10}$ and $OR^{14}$ respectively, with $R^{10}$ and $R^{14}$ being hydrogen, can be obtained from compounds of general formula (II) where the bond ═ in position 5 is a double bond and $R^7$ is hydrogen, with one of the methods reported in literature for such reactions, such as for example, with OsO$_4$, KMnO$_4$, H$_2$O$_2$ and formic, acetic or peracetic acid, followed by hydrolysis of the intermediate, at a temperature ranging from 0° C. to the reflux temperature.

Compounds of general formula (II) where $R^3$, $R^4$, $R^5$, $R^8$, $R^9$ and ═ have the meanings defined above, and $R^6$ and $R^7$ are $OR^{10}$ and $OR^{14}$ respectively, with $R^{10}$ and $R^{14}$ being hydrogen, can be obtained from compounds of general formula (II) where $R^6$ and $R^7$ taken together form an oxirane ring, with one of the methods reported in literature for such reactions, such as for example, by acidic or basic hydrolysis, at a temperature ranging from 0° C. to the reflux temperature.

Compounds of general formula (II) where $R^3$, $R^4$, $R^5$, $R^8$, $R^9$ and ═ have the meanings defined above, and $R^6$ is $OR^{10}$, $R^{10}$ being hydrogen, and $R^7$ is O with the meaning of a keto group, can be obtained from compounds of general formula (II) where $R^6$ and $R^7$ taken together form an oxirane ring, with one of the methods reported in literature for such reactions, such as for example, by oxidation with CrO$_3$ in pyridine or in the presence of an acid, such as H$_2$SO$_4$ in acetone or acetic acid, optionally in the presence of water, at a temperature ranging from 0° C. to the reflux temperature.

Compounds of general formula (II) where $R^3$, $R^4$, $R^5$, $R^6$, $R^8$, $R^9$ and ═ have the meanings defined above, and $R^7$ is $OR^{14}$, $R^{14}$ being hydrogen, when the bonds ═ in positions 4, 5, 6 and 7 are single bonds, can be obtained from compounds of general formula (II) where $R^7$ is O, with the meaning of ketone, by reduction with a complex hydride, such as for example, NaBH$_4$, optionally in the presence of a Lewis acid such as for example, CeCl$_3$, in an alcoholic or ethereal solvent, or LiAlH$_4$ in an ethereal solvent, LiBH$_4$ or LiAl(tBuO)$_3$H or with a metal, such as for example sodium, in an alcoholic solvent, at a temperature ranging from 0° C. to the reflux temperature.

Compounds of general formula (II) where $R^3$, $R^4$, $R^5$, $R^6$, $R^8$, $R^9$ and ═ have the meanings defined above, $R^7$ is O, with the meaning of a keto group, can be obtained from compounds of general formula (II) where $R^7$ is $OR^{14}$, $R^{14}$ being hydrogen, where the bond ═ linking the carbon atom in position 6 of the androstane skeleton with $R^7$ represents a single bond, with one of the methods reported in literature, such as, by oxidation with one of the reagents reported in literature for such oxidations, such as for example, iodoxybenzoic acid, Dess-Martin periodinane, oxalyl chloride and triethylamine and dimethylsulfoxide in methylene chloride, $CrO_3$ in pyridine or in sulfuric acid and acetone, pyridinium chlorochromate, pyridinium dichromate or chromic anhydride in sulfuric acid/acetone.

Compounds of general formula (II) where $R^3$, $R^4$, $R^5$, $R^6$, $R^7$, $R^9$ and $=$ have the meanings defined above, where the bond $=$ in position 5 represents a double bond, and $R^8$ is O, with the meaning of a keto group, can be obtained from compounds of general formula (II) where the bond $=$ linking the carbon atom in position 7 of the androstane skeleton with $R^8$ is a single bond and $R^8$ is hydrogen, with one of the methods reported in literature for such reactions, by oxidation with one of the reagents reported in literature for such oxidations, such as, for example, $Na_2Cr_2O_7$ in acetic acid in the presence of acetic anhydride; oxygen or air and N-hydroxyphthalimide, optionally in the presence of acetic anhydride and perbenzoic anhydride or ultraviolet light or an oxidant, such as oxygen and ferric salts in the presence of an organic quaternary ammonium salt; oxygen in the presence of a radical inducer, for example AIBN, followed by treatment with acetic anhydride and pyridine; t-BuOOH optionally in the presence of other oxidants, such as $CrO_3$, $KMnO_4$, $Mn_3O(OAc)_9$, $Mn(OAc)_3$, $RuCl_3$ and optionally a phase transfer quaternary ammonium catalyst; $KHSO_5$ in homogeneous phase or in a phase transfer system.

Compounds of general formula (II) where $R^3$, $R^4$, $R^5$, $R^6$, $R^7$, $R^9$ and $=$ have the meanings defined above, where the bond in position 5 represents a double bond, and $R^8$ is $OR^{14}$, with $R^{14}$ being hydrogen, can be obtained from compounds of general formula (II) where the bond $=$ linking the carbon atom in position 7 of the androstane skeleton with $R^8$ is a single bond and $R^8$ is hydrogen, with one of the methods reported in literature for such reactions, by oxidation, for example, with oxygen in the presence of a sensitizer, for example rose bengal, or a radical inducer, for example AIBN, followed by reduction with a complex metal hydride, ferrous salts; with oxygen and ferric salts in the presence of an organic quaternary ammonium salt; with t-butyl perbenzoate and $Cu_2Br_2$; with t-BuOCl, $H_2O_2$ and ferric salts; with peracetic acid and ferric perchlorate or with $Na_2Cr_2O_7$ in acetic acid in the presence of acetic anhydride.

Compounds of general formula (II) where $R^3$, $R^4$, $R^5$, $R^6$, $R^7$, $R^9$ and $=$ have the meanings defined above, where the bond $=$ in position 4 represents a single bond, the bond $=$ in position 5 represents a single or a double bond, and $R^8$ is $OR^{14}$, with $R^{14}$ being hydrogen, can be obtained from compounds of general formula (II) where $R^8$ is oxygen, with the meaning of a keto group, with one of the methods reported in literature such as, for example, reduction with a complex hydride, such as for example, $NaBH_4$, optionally in the presence of a Lewis acid such as for example $CeCl_3$, in an alcoholic or ethereal solvent, or $LiAlH_4$ in an ethereal solvent, $LiBH_4$ or with a metal, such as for example sodium, in an alcoholic solvent, at a temperature ranging from 0° C. to the reflux temperature.

Compounds of general formula (II) where $R^3$, $R^4$, $R^5$, $R^6$, $R^7$, $R^9$ and $=$ have the meanings defined above, and $R^8$ is O, with the meaning of a keto group, can be obtained from compounds of general formula (II) where the bond $=$ linking the carbon atom in position 7 with $R^8$ is a single bond and $R^8$ is $OR^{14}$, with $R^{14}$ being hydrogen, with one of the reagents reported in literature for such oxidations, such as for example, iodoxybenzoic acid, Dess-Martin periodinane, oxalyl chloride and triethylamine and DMSO, $CrO_3$ in pyridine or in sulfuric acid and acetone, pyridinium chlorochromate or pyridinium dichromate.

Compounds of general formula (II), where one of $R^7$ and $R^8$ is $C_1$-$C_6$ alkyl, the other being O with the meaning of a keto group, can be prepared from the corresponding compounds of general formula (II), where one of $R^7$ and $R^8$ is hydrogen the other being O with the meaning of a keto group, by treatment with a base, such as for example, NaH, KH, NaOMe, NaOtBu, KotBu or LDA in a solvent such as diethyl ether, dioxane, tetrahydrofuran, 1,2-dimethoxyethane, toluene, dimethylsulfoxide or their mixtures, at a temperature ranging from −78° C. to the reflux temperature, followed by quenching with a $C_1$-$C_6$ alkyl-LG, where LG is a leaving group, such as for example, chloro, bromo, iodo, mesyloxy, p-toluenesulfonyloxy, trifluoromethanesulfonyloxy, at a temperature ranging from −78° C. to the reflux temperature. The reaction can be carried out also in dichloromethane, chlorobenzene, toluene, hexane, water or their mixture, in the presence of NaOH or KOH and a quaternary ammonium salt, such as, for example, tetrabutylammonium chloride or bromide or iodide or hydrogensulfate, at a temperature ranging from 0° C. to the reflux temperature.

By using the same reactions reported above, compounds of general formula (II), where $R^6$ is $OR^{10}$ with $R^{10}$ being $C_1$-$C_6$ alkyl, can be prepared by treatment of the corresponding compounds of general formula (II), where $R^6$ is hydroxy, with compounds of general formula $C_1$-$C_6$ alkyl-LG, where LG is as defined above.

By using the same reactions reported above, compounds of general formula (II), where $R^7$ and $R^8$, independently, are $OR^{14}$ with $R^{14}$ being $C_1$-$C_6$ alkyl, can be prepared by treatment of the corresponding compounds of general formula (II), where $R^7$ and $R^8$ are hydroxy, with compounds of general formula $C_1$-$C_6$ alkyl-LG, where LG is as defined above.

By using the same reactions reported above, compounds of general formula (II) where $R^9$ is $C_1$-$C_6$ alkyl group can be obtained by treatment of compounds of general formula (II) where $R^9$ is H, with compounds of general formula $C_1$-$C_6$ alkyl-LG, where LG is as defined above.

Compounds of general formula (II), where one of $R^7$ and $R^8$ is a hydroxymethyl group, and the other is oxygen, with the meaning of a keto group, and the symbols $=$ in positions 4 and 5 are single bonds, can be prepared from the corresponding compounds of general formula (II), where one of $R^7$ and $R^8$ is hydrogen and the other is O, by treatment with a base, such as, for example, NaH, KH, NaOtBu, KOtBu, LDA in a solvent such as diethyl ether, dioxane, tetrahydrofuran, 1,2-dimethoxyethane, dimethylsulfoxide, toluene or their mixtures, at a temperature ranging from −78° C. to the reflux temperature, followed by quenching with paraformaldehyde or trioxane; or by alkylation with paraformaldehyde or trioxane in the presence of a Lewis acid, such as trimethylaluminum, optionally in the presence of a ligand, such as 2,6-diphenylphenol.

Compounds of general formula (II), where $R^6$ is $OR^{10}$ and $R^{10}$ is $C_2$-$C_7$ alkylcarbonyl, can be prepared by treatment of the corresponding compounds of general formula (II), where $R^6$ is hydroxy, by reaction with an appropriate $C_2$-$C_7$ alkylcarbonylhalide or $C_4$-$C_{14}$ alkylcarbonyl anhydride in a solvent such as diethyl ether, dioxane, tetrahydrofuran, 1,2-dimethoxyethane, toluene, N,N-dimethylformamide, dimethylsulfoxide, dichloromethane, pyridine or their mixtures, at a temperature ranging from −78° C. to the reflux temperature, optionally in the presence of a base, such as, for example, triethylamine, pyridine, 4-dimethylaminopyridine. The same reaction can be carried out also with the corresponding $C_2$-$C_7$ carboxylic acid in a solvent such as diethyl ether, dioxane, tetrahydrofuran, 1,2-dimethoxyethane, toluene, acetone, ethyl acetate, dichloromethane, chloroform, N,N-dimethylformamide, dimethylsulfoxide, water, or their mixtures, at a temperature ranging from −30° C. to the reflux temperature, in the presence of a condensing reagent such as, N,N'-dicyclohexylcarbodiimide, N-ethyl-N'-(3-dimethylaminopropyl)-carbodiimide hydrochloride, or the $C_2$-$C_7$ carboxylic acid can be treated previously with $SOCl_2$, $POCl_3$ or $PCl_5$, and then reacted with the above described compound of general formula (II) optionally in the presence of a base, such as, for example, NaOH, KOH, $Na_2CO_3$, $K_2CO_3$, $NaHCO_3$, $KHCO_3$, triethylamine, pyridine or 4-dimethylaminopyridine.

By using the same reactions reported above, compounds of general formula (II), where $R^7$ and/or $R^8$ are $OR^{14}$ with $R^{14}$ being $C_2$-$C_7$ alkylcarbonyl, can be prepared by treatment of the corresponding compounds of general formula (II), where $R^7$ and/or $R^8$ correspondingly, are hydroxy, the symbols ═ in positions 4 and 5 represent single bonds with compounds of general formula $C_2$-$C_7$ alkylcarbonylhalide or $C_4$-$C_{14}$ alkylcarbonylanhydride or $C_2$-$C_7$ carboxylic acid.

By using the same reactions reported above, compounds of general formula (II) where $R^9$ is $C_2$-$C_7$ alkylcarbonyl group can be obtained by treatment of compounds of general formula (II) where $R^9$ is H with compounds of general formula $C_2$-$C_7$ alkylcarbonylhalide or $C_4$-$C_{14}$ alkylcarbonylanhydride or $C_2$-$C_7$ carboxylic acid.

Compounds of general formula (II) where $R^7$ and/or $R^8$ are $ONO_2$ can be obtained by treatment of compounds of general formula (II), where $R^7$ and/or $R^8$ are, correspondingly, hydroxy, where the symbol ═ in position 5 represents a single bond, with nitric acid in acetic anhydride or acetic acid, nitric acid and sulfuric acid in dichloromethane, nitrosyl fluoride or tetrafluoroborate in acetonitrile.

Compounds of general formula (II), where one or both $R^7$ and $R^8$ are N∼$OR^{11}$, can be obtained by treatment of compounds of general formula (II), where one or both $R^7$ and $R^8$ are oxygen, with the meaning of keto groups, with compounds of general formula $H_2NOR^{11}$, where $R^{11}$ has the meanings defined above, in the form of the free base or of a salt, such as for example, hydrochloride, in a solvent such as dioxane, tetrahydrofuran, 1,2-dimethoxyethane, methanol, ethanol, N,N-dimethylformamide, pyridine, water or their mixtures, at a temperature ranging from 0° C. to the reflux temperature. The reaction may be carried out in the presence of a base, such as sodium or potassium hydroxide, sodium or potassium carbonate, sodium or potassium hydrogen carbonate, or of an acid, such as hydrochloric acid, hydrobromic acid, acetic acid, or of a salt, such as sodium or potassium acetate, sodium or potassium phosphate, disodium or dipotassium hydrogen phosphate, sodium or potassium dihydrogen phosphate.

Compounds of general formula (II), where one or both $R^7$ and $R^8$, are N∼$OR^{11}$, where $R^{11}$ is $C_2$-$C_7$ alkylcarbonyl or $C_1$-$C_6$ alkyl, can be obtained by treatment of compounds of general formula (II), where one or both $R^7$ and $R^8$ correspondingly are, N∼$OR^{11}$, with $R^{11}$ being hydrogen, with compounds of general formula $C_2$-$C_7$ alkylcarbonylhalide or $C_4$-$C_{14}$ alkylcarbonylanhydride or $C_2$-$C_7$ carboxylic acid following the acylation conditions described above or with compounds of general formula $C_1$-$C_6$ alkyl-LG following the alkylating conditions described above.

Compounds of general formula (II), where one or both $R^7$ and $R^8$, independently, are $CR^{12}R^{13}$, can be obtained by reaction of compounds of general formula (II) where one or both $R^7$ and $R^8$ correspondingly are oxygen, with the meaning of keto groups, with compounds of general formula (IV) or (V), as defined above, in the same reaction conditions above described involving compounds of general formula (IV) or (V).

Compounds of general formula (II) where one or both $R^7$ and $R^8$, are hydroxymethyl, can be obtained from compounds of general formula (II) where one or both $R^7$ and $R^8$ correspondingly are $CR^{12}R^{13}$, where $R^{12}$ and $R^{13}$ are hydrogens with one of the methods reported in literature such as, for example, by reaction with a borane like diborane, or its complexes with dimethylamine, dimethylsulfide, 9-borabicyclononane, diisopinocamphenylborane or diisoamylborane, in an ethereal solvent, such as, for example, diethyl ether, tetrahydrofuran, dioxane, 1,2-dimethoxyethane, followed by treatment with an alkaline aqueous hydrogen peroxide solution or sodium perborate.

With the same methods, also compounds of general formula (II) in which one or both $R^7$ and $R^8$ are hydroxyethyl can be obtained from compounds of general formula (II) where one or both $R^7$ and $R^8$ correspondingly are vinyl.

Compounds of general formula (II) where one or both $R^7$ and $R^8$ are vinyl can be obtained by reaction of compounds of general formula (II) where one or both $R^7$ and $R^8$ correspondingly are CHO, with methyltriphenylphosphonium chloride or bromide or iodide by using the same reaction conditions above described involving compounds of general formula (IV) or (V).

Compounds of general formula (II) where one or both $R^7$ and $R^8$ are ethynyl, can be obtained by reaction of compounds of general formula (II) where one or both $R^7$ and $R^8$ correspondingly are CHO, with chloromethyltriphenylphosphonium chloride or bromide or iodide and n-butyllithium from −78° C. to RT followed by further treatment with n-butyllithium.

Compounds of general formula (II) where the substituents $R^7$ and $R^8$, independently, are $C_1$-$C_6$ alkyl groups, can be obtained from compounds of general formula (II) where $R^7$ and $R^8$, being $R^7$ and $R^8$ the same or different, are $CR^{12}R^{13}$, where $R^{12}$ and $R^{13}$ are hydrogen or $C_1$-$C_5$ alkyl groups, with one of the methods reported in literature for such reactions, such as by catalytic hydrogenation, in the reaction conditions described above for similar transformations of compounds of general formula (I).

Compounds of general formula (II), where $R^7$ and $R^8$, independently, are $C_1$-$C_6$ alkyl groups, in particular methyl or ethyl, can be obtained from compounds of general formula (II) where $R^7$ and $R^8$, being $R^7$ and $R^8$ the same or different, are hydroxymethyl or 2-hydroxyethyl with one of the methods reported in literature for such reactions, such as treatment with mesyl or tosylchloride, in the presence of a base, followed by reduction with a hydride, such as, for example, sodium borohydride or lithium aluminumhydride, or by deoxygenation with one of the methods reported in literature for such a kind of reaction, such as, for example, reaction with thiocarbonyl-diimidazole and tri-n-butylstannane, carbon disulfide in the presence of a base followed by reaction with methyl iodide and subsequent treatment with tri-n-butylstannane, $NaBH_3CN$ and $ZnI_2$, $NaBH_4$ in acetic acid.

Compounds of general formula (II), where one or both $R^7$ and $R^8$ are $COOR^{15}$, where $R^{15}$ is hydrogen, can be obtained from compounds of general formula (II) where one or both $R^7$ and $R^8$ correspondingly are hydroxymethyl, by oxidation with one of the reagents reported in literature for such oxidations, such as, for example, iodoxybenzoic acid, Dess-Martin periodinane, oxalyl chloride and triethylamine and dimethylsulfoxide in methylene chloride, $CrO_3$ in pyridine or in sulfuric acid and acetone, pyridinium chlorochromate, pyridinium dichromate, to give the intermediate aldehyde where one or both $R^7$ and $R^8$ correspondingly are CHO, followed by further oxidation to the carboxylic acid with one of the reagents reported in literature for such oxidations, such as, for example, potassium permanganate, chromic anhydride in sulfuric acid/acetone, pyridinium dichromate in N,N-dimethylformamide.

Compounds of general formula (II), where one or both $R^7$ and $R^8$ are $COOR^{15}$, where $R^{15}$ is a $C_1$-$C_6$ alkyl group, can be obtained from compounds of general formula (II) where one or both $R^7$ and $R^8$ correspondingly are COOH, by treatment with diazomethane, trimethylsilyldiazomethane or a compound of general formula $R^{15}OH$ with one of the methods reported in literature for such transformations, such as for example, condensation in the presence of a condensing reagent such as, N,N'-dicyclohexylcarbodiimide or N-ethyl-N'-(3-dimethylamino-propyl)carbodiimide hydrochloride, or compounds of formula (II) can be treated previously with $SOCl_2$, $POCl_3$, $PCl_5$, and then reacted with a compound of general formula $R^{15}OH$ optionally in the presence of a base, such as, for example, triethylamine, pyridine, or 4-dimethylaminopyridine.

Compounds of general formula (II), where one or both $R^7$ and $R^8$ are NHCHO, can be obtained from compounds of general formula (II) where one or both $R^7$ and $R^8$ correspondingly are N⋯ $OR^{11}$, where $R^{11}$ is hydrogen, with one of the methods reported in literature for such reductions, such as for example, treatment with lithium aluminumhydride, catalytic hydrogenation, or sodium or lithium or magnesium in an alcohol to give the corresponding amine where $R^7$ and $R^8$ are $NH_2$, followed by formylation with formic acid in the presence of a condensing agent, such as for example, N,N'-dicyclohexylcarbodiimide or N-ethyl-N'-(3-dimethylamino-propyl)carbodiimide hydrochloride, or optionally in the presence of a base, such as, for example, triethylamine, pyridine or 4-dimethylaminopyridine.

Compounds of general formula (II), where one or both $R^7$ and $R^8$ are spirooxirane, can be obtained from compounds of general formula (II) where one or both $R^7$ and $R^8$ are correspondingly $CR^{12}R^{13}$, where $R^{12}$ and $R^{13}$ are hydrogen, with one of the reagents reported in literature for such reactions, such as, for example perbenzoic acid, m-chloroperbenzoic acid, magnesium perphthalate, perphthalic acid, peracetic acid or hydrogen peroxide and sodium hydroxide in acetonitrile.

Compounds of general formula (II), where one or both $R^7$ and $R^8$ are spirooxirane, can be obtained from compounds of general formula (II) where one or both $R^7$ and $R^8$ are correspondingly O, with the meaning of keto groups, with one of the reagents reported in literature for such reactions, such as for example trimethylsulfonium iodide or trimethylsulfoxonium iodide in the presence of a base, such as sodium hydride, sodium methoxide or potassium tert-butoxide.

Compounds of general formula (II), where one or both $R^7$ and $R^8$ is spirocyclopropane, can be obtained from compounds of general formula (II) where one or both $R^7$ and $R^8$ are correspondingly $CR^{12}R^{13}$, where $R^{12}$ and $R^{13}$ are hydrogen, with one of the reagents reported in literature for such reactions, such as, for example, diiodomethane and diethyltin or tin-copper alloy.

Compounds of general formula (II) where the symbols $R^3$, $R^4$, $R^5$, $R^6$, $R^7$, $R^8$, $R^9$, and ═ have the meanings defined above and at least one ═ represents a single bond, can be obtained by reduction of the corresponding compounds of general formula (II) where the corresponding symbol ═ represents a double bond, by catalytic hydrogenation, either with hydrogen gas or in hydrogen transfer conditions, in the presence of a metal catalyst, such as Pd/C, $PtO_2$, Pt, Pt/C or Raney Nickel. As a hydrogen transfer reagent, ammonium formate, sodium hypophosphite or cyclohexadiene can be used. The reaction can be carried out in a solvent, such as for example, ethanol, methanol, ethyl acetate, dioxane, tetrahydrofuran, acetic acid, N,N-dimethylformamide, water or their mixtures, at a temperature ranging from 0° C. to the reflux temperature, at a pressure ranging from atmospheric pressure to 10 atm. According to the substrate and the conditions used, the hydrogenation can selectively affect one or more double bonds. The reduction can also be carried out with sodium, lithium, potassium or calcium in liquid ammonia, methylamine or ethylamine, optionally in the presence of tetrahydrofuran or diethyl ether, at a temperature ranging from −30° C. to the reflux temperature of the solvent or of the mixture.

Compounds of general formula (III)-(V) are commercially available or can be prepared from commercially available compounds by standard procedures.

In all said transformations, any interfering reactive group can be protected and then deprotected according to well-established procedures described in organic chemistry (see for example: T. W. Greene and P. G. M. Wuts "Protective Groups in Organic Synthesis", J. Wiley & Sons, Inc., 3$^{rd}$ Ed., 1999) and well known to those skilled in the art.

All said transformations are only examples of well-established procedures described in organic chemistry (see for example: J. March "Advanced Organic Chemistry", J. Wiley & Sons, Inc., 4$^{th}$ Ed., 1992) and well known to those skilled in the art.

We have found that the derivatives (I) and their pharmaceutically acceptable salts, prepared according to the invention, are useful agents for the treatment of cardiovascular disorders, such as heart failure and hypertension.

The pharmaceutical compositions will contain at least one compound of Formula (I) as an active ingredient, in an amount such as to produce a significant therapeutic effect. The compositions covered by the present invention are entirely conventional and are obtained with methods which are common practice in the pharmaceutical industry, such as, for example, those illustrated in Remington's Pharmaceutical Science Handbook, Mack Pub. N.Y.—latest edition. According to the administration route chosen, the compositions will be in solid or liquid form, suitable for oral, parenteral or intravenous administration. The compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

For any compound, the therapeutically effective dose can be estimated initially either in cell culture assays or in animal models, usually mice, rats, guinea pigs, rabbits, dogs, or pigs.

The animal model may also be used to determine the appropriate concentration range and route of administration. Such information can then be used to determine useful doses and routes for administration in humans.

The precise effective dose for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgment of the clinician. Generally, an effective dose will be from 0.001 mg/kg to 10 mg/kg, preferably 0.005 mg/kg to 5 mg/kg. Compositions may be administered individually to a patient or may be administered in combination with other agents, drugs or hormones.

The medicament may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles.

A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol.

Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The medicament of this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, intravaginal or rectal means.

Dosage treatment may be a single dose schedule or a multiple dose schedule.

Further object of the present invention is the use of said compounds of general formula (I) in the preparation of a medicament useful in the treatment of cardiovascular diseases such as heart failure and hypertension. Hypertension affects approximately 30% of the world's population over 60 and represents the leading preventable cause of premature morbidity and mortality due to major cardiovascular events and organ cardiovascular complications such as coronary heart disease, chronic heart failure, stroke, kidney failure, negative vascular remodeling, retinal damage and cognitive disorders (Ritz E., *Am. J. Cardiol.*, 2007, Aug. 6, 100 (3A): 53J-60J; Messerli F. H., et al., *Lancet*, 2007, Aug. 18, 370, 9587, 591-603).

A further object of the present invention are pharmaceutical compositions containing one or more of the compounds of formula (I) described earlier, in combination with excipients and/or pharmacologically acceptable diluents.

The compositions in question may, together with the compounds of formula (I), contain known active principles.

A further embodiment of the invention is a process for the preparation of pharmaceutical compositions characterised by mixing one or more compounds of formula (I) with suitable excipients, stabilizers and/or pharmaceutically acceptable diluents.

The following examples illustrate the invention without limiting it.

Abbreviations
br. s: broad signal (NMR)
DCM: dichloromethane
DMSO: dimethylsulfoxide
Et$_2$O: diethyl ether
EtOAc: ethyl acetate
KOH: potassium hydroxide
LTA: lead tetraacetate
MCPBA: meta-chloroperbenzoic acid
MeOH: methanol
MgSO$_4$: magnesium sulfate
Na$_2$SO$_4$: sodium sulfate
NBS: N-bromosuccinimide
NHP: N-hydroxyphtalimide
NHS: N-hydroxysuccinimide
NMO: N-methylmorpholine oxide
OsO$_4$: osmium tetroxide
PTSA: para-toluenesulfonic acid
RT: room temperature
TBAF: tetrabutylammonium fluoride
THF: tetrahydrofuran
TMS: tetramethylsilane
TPAP: tetrapropylammonium perruthenate General Remarks: $^1$H spectra were recorded at 300 MHz with a Bruker instrument unless otherwise specified. The chemical shift values are given in ppm and the coupling constants in Hz. Flash column chromatography was carried out using silica gel (Merck 230-400 mesh).

Example 1

(E)-3-(2-Aminoethoxyimino)-4-methylandrost-4-en-17β-ol hydrochloride (I-aa)

To a stirred solution of 4-methyltestosterone (203 mg) in dioxane (3.7 ml), a solution of 2-aminoethoxyamine dihydrochloride (259 mg) in water (2 ml) was rapidly added dropwise. After 24 h dioxane (20 ml) and brine (10 ml) were added and the mixture was stirred for 10 min. The phases were separated and the aqueous phase was extracted with dioxane (2×). The combined organic extracts were washed with brine, dried over MgSO$_4$, filtered and evaporated to dryness. The residue was triturated with Et$_2$O for 5 h and the precipitate was filtered. The crude product was dissolved in water and freeze-dried to give the title compound (I-aa) as a white solid (197 mg, 74%).

$^1$H-NMR (300 MHz, DMSO-d$_6$, ppm from TMS): δ 7.77 (br. s, 3H), 4.44 (d, 1H), 4.14 (t, 2H), 3.41 (m, 1H), 3.06 (t, 2H), 2.95 (m, 1H), 2.70 (m, 1H), 2.12-0.68 (m, 17H), 1.75 (s, 3H), 1.00 (s, 3H), 0.65 (s, 3H).

Example 2

(E)-3-(2-Aminoethoxyimino)-4,4-dimethylandrost-5-en-17β-ol fumarate (I-ab)

To a stirred solution of 17β-hydroxy-4,4-dimethylandrost-5-en-3-one, (342 mg) in pyridine (5 ml), 2-aminoethoxyamine dihydrochloride (707 mg) was added. After 4 h at 100° C. the solution was evaporated to dryness. The crude product was purified by flash chromatography (SiO$_2$, DCM/MeOH/26% NH$_4$OH 90/10/1). To the concentrated fractions a stoichiometric amount of fumaric acid in MeOH was added and evaporated to dryness to give title compound I-ab (386 mg, 73%).

$^1$H-NMR (300 MHz, DMSO-d$_6$, ppm from TMS): δ 8.20 (br. s, 4H), 6.43 (s, 2H), 5.57 (m, 1H), 4.45 (br. s, 1H), 4.09 (t, 2H), 3.42 (m, 1H), 3.00 (m, 2H), 2.83 (m, 1H), 2.40-0.80 (m, 16H), 1.25 (s, 3H), 1.19 (s, 3H), 0.75 (s, 3H), 0.63 (s, 3H).

Example 3

(E)-3-(2-Dimethylaminoethoxyimino)-4,4-dimethylandrost-5-en-17β-ol fumarate (I-ac)

The title compound was prepared in 63% yield (467 mg) as described in Example 2 starting from 17β-hydroxy-4,4-dimethylandrost-5-en-3-one (454 mg) and 2- dimethylaminoethoxyamine dihydrochloride (547 mg).

$^1$H-NMR (300 MHz, DMSO-d$_6$, ppm from TMS): δ 6.50 (s, 2H), 5.56 (m, 2H), 4.45 (d, 1H), 4.06 (t, 2H), 3.42 (m, 1H), 2.76 (m, 1H), 2.56 (m, 2H), 2.30-0.80 (m, 16H), 2.22 (m, 6H), 1.24 (s, 3H), 1.17 (s, 3H), 0.74 (s, 3H), 0.63 (s, 3H).

Example 4

(E) 3-[3-(R)-Pyrrolidinyl]oxyimino-4,4-dimethylandrost-5-en-17β-ol fumarate (I-ad)

The title compound was prepared in 78% yield (347 mg) as described in Example 2 starting from 17β-hydroxy-4,4-dimethylandrost-5-en-3-one, (274 mg) and 3-(R)-pyrrolidinyloxyamine dihydrochloride (Preparation 12, 452 mg).

$^1$H-NMR (300 MHz, DMSO-d$_6$/CF$_3$COOH, ppm from TMS): δ 8.94 (br. s, 1H), 8.80 (br. s, 1H), 6.60 (s, 2H), 5.57 (m, 1H), 4.80 (m, 1H), 4.43 (m, 1H), 3.35-0.80 (m, 23H), 1.25 (s, 3H), 1.18 (s, 3H), 0.75 (s, 3H), 0.63 (s, 3H).

Example 5

(E)-3-(2-Aminoethoxyimino)-4,4-dimethylandrost-5-en-17-one fumarate (I-ae)

To a stirred solution of 3-(E)-{2-[N-(9-fluorenylmethoxycarbonyl)]-aminoethoxyimino}-4,4-dimethylandrost-5-en-17-one (Preparation 1, 199 mg) in dry THF (2.6 ml) at 0° C., 1M TBAF in THF (0.4 ml) was added. After stirring at RT for 1 h, the solution was concentrated and purified by flash chromatography (SiO$_2$, DCM/MeOH/26% NH$_4$OH 90/10/0.1). To the concentrated fractions a stoichiometric amount of fumaric acid in MeOH was added and evaporated to dryness. The residue was triturated with Et$_2$O and the precipitate was filtered to give the title compound I-ae as a white solid (61 mg, 38%).

$^1$H-NMR (300 MHz, DMSO-d$_6$, ppm from TMS): δ 8.10 (br. s, 4H), 6.40 (s, 2H), 5.61 (m, 1H), 4.05 (t, 2H), 2.95 (t, 2H), 2.84 (m, 1H), 2.45-0.89 (m, 16H), 1.27 (s, 3H), 1.20 (s, 3H), 0.79 (s, 3H), 0.77 (s, 3H).

Example 6

(E)-3-(2-Dimethylaminoethoxyimino)-4,4-dimethylandrost-5-en-17-one fumarate (I-af)

To a solution of (E)-3-(2-dimethylaminoethoxyimino)-4,4-dimethyl-androst-5-en-17β-ol as base (Example 3, 157 mg) in DCM (8 ml) under N$_2$, NMO (56 mg), TPAP (6 mg) and 4 Å molecular sieves (250 mg) were added. The mixture was stirred for 1 h and then SiO$_2$ was added. The mixture was purified by flash chromatography (SiO$_2$, DCM/MeOH/26% NH$_4$OH 90/10/1). To the concentrated fractions a stoichiometric amount of fumaric acid in MeOH was added and evaporated to dryness to give title compound I-af (142 mg, 86%).

$^1$H-NMR (300 MHz, DMSO-d$_6$, ppm from TMS): δ 6.40 (s, 2H), 5.60 (m, 1H), 4.10 (m, 2H), 3.35 (m, 2H), 2.77 (m, 1H), 2.60 (m, 2H), 2.45-0.88 (m, 16H), 2.22 (m, 6H), 1.28 (s, 3H), 1.20 (s, 3H), 0.78 (s, 3H), 0.76 (s, 3H).

Example 7

(E)-3-(2-Aminoethoxyimino)-4,4-dimethylandrostan-17β-ol fumarate (I-ag)

The title compound was prepared in 87% yield (484 mg) as described in Example 2 starting from 4,4-dimethyl-17β-hydroxyandrostan-3-one, (361 mg) and 2-aminoethoxyamine dihydrochloride (505 mg).

$^1$H-NMR (300 MHz, DMSO-d$_6$/CF$_3$COOH, ppm from TMS): δ 7.78 (br. s, 3H), 6.60 (s, 2H), 4.07 (t, 2H), 3.39 (t, 1H), 3.06 (m, 3H), 2.12-0.50 (m, 19H), 1.04 (s, 3H), 0.98 (s, 3H), 0.92 (s, 3H), 0.60 (s, 3H).

Example 8

(E)-3-(2-N-Methylaminoethoxyimino)-4,4-dimethylandrostan-17β-ol fumarate (I-ah)

The title compound was prepared in 88% yield (194 mg) as described in Example 2 starting from 4,4-dimethyl-17β-hydroxyandrostan-3-one (139 mg) and 2-N-methyl-aminoethoxyamine dihydrochloride (Preparation 13, 213 mg).

$^1$H-NMR (300 MHz, DMSO-d$_6$/CF$_3$COOH, ppm from TMS): δ 8.44 (br. s, 2H), 6.60 (s, 2H), 4.14 (t, 2H), 3.39 (t, 1H), 3.18 (m, 2H), 3.02 (m, 1H), 2.58 (t, 3H), 2.13-0.50 (m, 19H), 1.05 (s, 3H), 0.98 (s, 3H), 0.92 (s, 3H), 0.60 (s, 3H).

Example 9

(E)-3-(3-Aminopropoxyimino)-4,4-dimethylandrostan-17β-ol fumarate (I-ai)

The title compound was prepared in 87% yield (352 mg) as described in Example 2 starting from 4,4-dimethyl-17β-hydroxyandrostan-3-one (211 mg) and 3- aminopropoxyamine dihydrochloride (320 mg).

$^1$H-NMR (300 MHz, DMSO-d$_6$/CF$_3$COOH, ppm from TMS): δ 7.65 (br. s, 3H), 6.60 (s, 2H), 3.99 (t, 2H), 3.39 (t, 2H), 2.94 (m, 1H), 3.02 (m, 1H), 2.84 (m, 2H), 2.10-0.50 (m, 19H), 1.04 (s, 3H), 0.97 (s, 3H), 0.92 (s, 3H), 0.60 (s, 3H).

Example 10

(E)-3-(3-N-Methylaminopropoxyimino)-4,4-dimethylandrostan-17β-ol fumarate (I-aj)

The title compound was prepared in 69% yield (348 mg) as described in Example 2 starting from 4,4-dimethyl-17β-hydroxyandrostan-3-one (311 mg) and 3-methylamino-propoxyamine dihydrochloride (Preparation 14, 519 mg).

$^1$H-NMR (300 MHz, DMSO-d$_6$/CF$_3$COOH, ppm from TMS): δ 8.33 (br. s, 2H), 6.60 (s, 2H), 3.98 (t, 2H), 3.39 (t, 1H), 2.93 (m, 3H), 2.55 (t, 3H), 2.11-0.50 (m, 21H), 1.04 (s, 3H), 0.97 (s, 3H), 0.92 (s, 3H), 0.60 (s, 3H).

Example 11

(E)-3-[3-(R)-Pyrrolidinyl]oxyimino-4,4-dimethylandrostan-17β-ol fumarate (I-ak)

The title compound was prepared in 87% yield (510 mg) as described in Example 2 starting from 4,4-dimethyl-17β-hydroxyandrostan-3-one (311 mg) and 3-(R)-pyrrolidinyloxyamine dihydrochloride (Preparation 12, 592 mg).

$^1$H-NMR (300 MHz, DMSO-d$_6$/CF$_3$COOH, ppm from TMS): δ 8.90 (br. s, 1H), 8.80 (br. s, 1H), 6.60 (s, 2H), 4.75 (m, 1H), 3.33 (t, 1H), 3.07 (m, 4H), 2.09 (m, 1H), 2.12-0.51 (m, 21H), 1.05 (s, 3H), 0.98 (s, 3H), 0.92 (s, 3H), 0.60 (s, 3H).

Example 12

(E)-3-[3-(S)-Pyrrolidinyl]oxyimino-4,4-dimethylandrostan-17β-ol fumarate (I-al)

The title compound was prepared in 83% yield (181 mg) as described in Example 2 starting from 4,4-dimethyl-17β-hydroxyandrostan-3-one (133 mg) and 3-(S)-pyrrolidinyloxyamine dihydrochloride (Preparation 15, 219 mg).

$^1$H-NMR (300 MHz, DMSO-d$_6$/CF$_3$COOH, ppm from TMS): δ 8.89 (br. s, 1H), 8.81 (br. s, 1H), 6.60 (s, 2H), 4.76 (m, 1H), 3.39 (t, 1H), 3.34-3.10 (m, 4H), 2.93 (m, 1H), 2.14-0.50 (m, 21H), 1.05 (s, 3H), 0.98 (s, 3H), 0.91 (s, 3H), 0.60 (s, 3H).

Example 13

(E)-3-(2-Aminoethoxyimino)-4,4-dimethylandrostan-17-one fumarate (I-am)

The title compound was prepared in 68% yield (187 mg) as described in Example 5 starting from 3-(E)-{2-[N-(9-fluorenylmethoxycarbonyl)]aminoethoxyimino}-4,4-dimethylandrostan-17-one (Preparation 2, 332 mg) and 1M TBAF in THF (0.66 ml).

$^1$H-NMR (300 MHz, DMSO-d$_6$/CF$_3$COOH, ppm from TMS): δ 7.7 (br. s, 3H), 6.60 (s, 2H), 4.08 (t, 2H), 3.05 (m, 3H), 2.43-0.55 (m, 19H), 1.06 (s, 3H), 0.99 (s, 3H), 0.95 (s, 3H), 0.76 (s, 3H).

Example 14

(E)-3-(3-Aminopropoxyimino)-4,4-dimethylandrostan-17-one fumarate (I-an)

The title compound was prepared in 63% yield (97 mg) as described in Example 5 starting from 3-(E)-{3-[N-(9-fluorenylmethoxycarbonyl)]aminopropoxyimino}-(4,4-dimethylandrostan-17-one (Preparation 3, 188 mg) and 1M TBAF in THF (0.40 ml).

$^1$H-NMR (300 MHz, DMSO-d$_6$/CF$_3$COOH, ppm from TMS): δ 7.66 (br. s, 3H), 6.60 (s, 2H), 3.99 (t, 2H), 2.95 (m, 1H), 2.84 (m, 2H), 2.44-0.55 (m, 21H), 1.06 (s, 3H), 0.98 (s, 3H), 0.94 (s, 3H), 0.76 (s, 3H).

Example 15

(E)-3-[3-(R)-Pyrrolidinyl]oxyimino-4,4-dimethylandrostan-17-one fumarate (I-ao)

The title compound was prepared in 57% yield (57 mg) as described in Example 5 starting from 3-(E)-{-1-[N-(9-fluorenylmethoxycarbonyl]-3-(R)-pyrrolidinyloxyimino}-4,4-dimethylandrostan-17-one (Preparation 4, 120 mg) and 1M TBAF in THF (0.44 ml).

$^1$H-NMR (300 MHz, DMSO-d$_6$/CF$_3$COOH, ppm from TMS): δ 8.92 (br. s, 1H), 8.80 (br. s, 1H), 6.60 (s, 2H), 4.75 (m, 1H), 3.35-3.07 (m, 4H), 2.97 (m, 1H), 2.43-0.58 (m, 21H), 1.06 (s, 3H), 0.99 (s, 3H), 0.95 (s, 3H), 0.76 (s, 3H).

Example 16

(E)-3-(2-Aminoethoxyimino)-4,4-dimethylandrostane-5α,6α,17β-triol fumarate (I-ap)

The title compound was prepared in 93% yield (420 mg) as described in Example 2 starting from 5α,6α,17β-trihydroxy-4,4-dimethylandrostan-3-one (Preparation 5, 300 mg) and 2-aminoethoxyamine dihydrochloride (510 mg).

$^1$H-NMR (300 MHz, DMSO-d$_6$/CF$_3$COOH, ppm from TMS): δ 7.77 (br. s, 3H), 6.60 (s, 2H), 4.05 (t, 2H), 3.91 (m, 1H), 3.41 (t, 1H), 3.00 (m, 3H), 2.30-0.74 (m, 16H), 1.36 (s, 3H), 1.22 (s, 3H), 0.78 (s, 3H), 0.58 (s, 3H).

Example 17

(E)-3-[3-(R)-Pyrrolidinyl]oxyimino-4,4-dimethylandrostane-5α,6α,17β-triol hydrochloride (I-aq)

The title compound was prepared in 90% yield (121 mg) as described in Example 2 starting from 5α,6α,17β-trihydroxy-4,4-dimethylandrostan-3-one, (Preparation 5, 100 mg) and 3-(R)-pyrrolidinyloxyamine dihydrochloride (Preparation 12, 200 mg).

$^1$H-NMR (300 MHz, DMSO-d$_6$, ppm from TMS): δ 8.82 (br. s, 2H), 4.74 (m, 1H), 4.41 (d, 1H), 4.37 (d, 1H), 3.88 (m, 1H), 3.68 (s, 1H), 3.41 (m, 1H), 3.35-2.80 (m, 5H), 2.30-0.70 (m, 18H), 1.37 (s, 3H), 1.22 (s, 3H), 0.79 (s, 3H), 0.58 (s, 3H).

Example 18

(E)-3-(2-Aminoethoxyimino)-5α,6α-dihydroxy-4,4-dimethylandrostan-17-one fumarate (I-ar)

To a stirred solution of (E)-3-(2-aminoethoxyimino)-4,4-dimethylandrostane-5α,6α,17β-triol (Example 16, 109 mg) in dioxane (3.5 ml) and water (0.4 ml), NBS (112 mg) was added. After 5 h THF (15 ml) and brine (20 ml) were added and the mixture stirred for 10 min. The phases were separated and the aqueous phase was extracted with THF. The combined organic extracts were washed with aqueous NaHSO$_3$, brine, dried over MgSO$_4$, filtered and evaporated to dryness. The crude product was purified by flash chromatography (SiO$_2$, DCM/MeOH/26% NH$_4$OH 90/10/1). To the concentrated fractions a stoichiometric amount of fumaric acid in MeOH was added and evaporated to dryness. The residue was triturated with Et$_2$O for 0.5 h and the precipitate was filtered to give the title compound as a white solid (58 mg, 55%).

$^1$H-NMR (300 MHz, DMSO-d$_6$/CF$_3$COOH, ppm from TMS): δ 7.80 (br. s, 3H), 6.60 (s, 2H), 4.06 (t, 2H), 3.94 (dd, 1H), 3.00 (m, 3H), 2.45-1.04 (m, 16H), 1.38 (s, 3H), 1.24 (s, 3H), 0.81 (s, 3H), 0.73 (s, 3H).

Example 19

(E)-3-[3-(R)-Pyrrolidinyl]oxyimino-5α,6α-dihydroxy-4,4-dimethyl-androstan-17-one fumarate (I-as)

The title compound was prepared in 59% yield (50 mg) as described in Example 18 starting from (E)-3-[3-(R)-pyrrolidinyl]oxyimino-4,4-dimethylandrostane-5α,6α,17β-triol hydrochloride (Example 17, 71 mg).

$^1$H-NMR (300 MHz, DMSO-d$_6$/CF$_3$COOH, ppm from TMS): δ 8.91 (br. s, 1H), 8.78 (br. s, 1H), 6.60 (s, 2H), 4.75

(m, 1H), 3.93 (dd, 1H), 3.38-1.00 (m, 23H), 1.38 (s, 3H), 1.24 (s, 3H), 0.81 (s, 3H), 0.73 (s, 3H).

Example 20

(E)-3-(2-Aminoethoxyimino)-4,4-dimethylandrostan-6,17-dione fumarate (I-at)

The title compound was prepared as described in Example 1 starting from 4,4-dimethylandrostan-3,6,17-trione, (Preparation 6, 80 mg) and 2-aminoethoxyamine dihydrochloride (37 mg). The crude product was purified by flash chromatography (Si$_2$, DCM/MeOH/26% NH$_4$OH 90/10/0.1). To the concentrated fractions a stoichiometric amount of fumaric acid in MeOH was added and evaporated to dryness. The residue was triturated with Et$_2$O and the precipitate was filtered to give the title compound as a white solid (36 mg, 30%).

$^1$H-NMR (300 MHz, DMSO-d$_6$/CF$_3$COOH, ppm from TMS): δ 7.78 (br. s, 3H), 6.60 (s, 2H), 4.09 (t, 2H), 3.15 (m, 1H), 3.06 (m, 2H), 2.43 (s, 1H), 2.45-1.05 (m, 16H), 1.38 (s, 3H), 1.10 (s, 3H), 0.94 (s, 3H), 0.78 (s, 3H).

Example 21

(E)-3-[3-(R)-Pyrrolidinyl]oxyimino-4,4-dimethyl-5α-hydroxyandrostan-6,17-dione fumarate (I-au)

The title compound was prepared in 82% yield (33 mg) as described in Example 5 starting from 3-(E)-{1-[N-(9-fluorenylmethoxycarbonyl)]-3-(R)-pyrrolidinyloxyimino}-4,4-dimethyl-5α-hydroxyandrostan-6,17-dione (Preparation 7, 48 mg) and 1M TBAF in THF (0.11 ml).

$^1$H-NMR (300 MHz, DMSO-d$_6$/CF$_3$COOH, ppm from TMS): δ 8.93 (br. s, 1H), 8.82 (br. s, 1H), 6.60 (s, 2H), 4.75 (m, 1H), 3.35-1.10 (m, 23H), 1.42 (s, 3H), 1.15 (s, 3H), 0.97 (s, 3H), 0.75 (s, 3H).

Example 22

(E)-3-(2-Aminoethoxyimino)-4,4-dimethyl-5α,6α-epoxyandrostan-17β-ol hydrochloride (I-av)

The title compound was prepared as described in Example 2 starting from 5α,6α-epoxy-17β-hydroxy-4,4-dimethylandrostan-3-one, (Preparation 8, 54 mg) and 2-aminoethoxyamine dihydrochloride (97 mg). The solution was evaporated, water was added and the aqueous phase was extracted with THF. The combined organic extracts were washed with brine, dried over Na$_2$SO$_4$ and evaporated to dryness. The crude product was triturated with diisopropyl ether/MeOH 95/5 and the precipitate was filtered to give the title compound (47 mg, 68%).

$^1$H-NMR (300 MHz, DMSO-d$_6$/CF$_3$COOH, ppm from TMS): δ 7.82 (br. s, 3H), 4.10 (t, 2H), 3.39 (t, 1H), 3.12-2.80 (m, 4H), 2.43-0.68 (m, 16H), 1.26 (s, 3H), 0.98 (s, 3H), 0.80 (s, 3H), 0.57 (s, 3H).

Example 23

(E)-3-[3-(R)-Pyrrolidinyl]oxyimino-4,4-dimethyl-5α,6α-epoxyandrostan-17β-ol hydrochloride (I-aw)

Prepared in 75% yield (51 mg) as described in Example 2 starting from 5α,6α-epoxy-17β-hydroxy-4,4-dimethylandrostan-3-one, (Preparation 8, 50 mg) and 3-(R)-pyrrolidinyloxyamine dihydrochloride (Preparation 12, 105 mg).

$^1$H-NMR (300 MHz, DMSO-d$_6$/CF$_3$COOH, ppm from TMS): δ 9.00 (br. s, 1H), 8.89 (br. s, 1H), 4.79 (m, 1H), 3.47-2.75 (m, 7H), 2.39-0.69 (m, 18H), 1.26 (s, 3H), 0.98 (s, 3H), 0.80 (s, 3H), 0.56 (s, 3H).

Example 24

(E)-3-(2-Aminoethoxyimino)-4,4-dimethyl-6α-hydroxymethyl-17β-hydroxyandrostan-7-one fumarate (I-ax)

4,4-Dimethyl-6α-hydroxymethyl-17β-hydroxyandrostan-3,7-dione (Preparation 9, 69 mg) and aminoethoxyamine dihydrochloride (28 mg) were dissolved in pyridine (0.5 ml) and stirred at RT for 4.5 h. Water was added and after extraction of the aqueous layer with AcOEt and tert-BuOH, the combined organic phases were dried and evaporated. The crude reaction mixture was purified by flash chromatography (SiO$_2$, CHCl$_3$/MeOH/26% NH$_4$OH 90/10/1). To the concentrated fractions, a stoichiometric amount of fumaric acid in MeOH was added. After addition of a 1/1 mixture of EtOAc/Et$_2$O, the precipitate obtained was filtered to give the title compound I-ax (63 mg, 62%) as a white powder.

$^1$H-NMR (300 MHz, DMSO-d$_6$/CF$_3$COOH, ppm from TMS): δ 7.80 (br. s, 3H), 6.60 (s, 2H), 4.10 (t, 2H), 3.69 (dd, 1H), 3.58 (dd, 1H), 3.41 (t, 1H), 3.07 (m, 2H), 2.77 (m, 1H), 2.50-0.85 (m, 16H), 1.10 (s, 3H), 1.05 (s, 3H), 0.88 (s, 3H), 0.62 (s, 3H).

Example 25

(E)-3-(2-Aminoethoxyimino)-4,4-dimethyl-6α-hydroxymethylandrostan-7α,17β-diol fumarate (I-ay)

4,4-Dimethyl-6α-hydroxymethyl-7α,17β-dihydroxyandrostan-3-one (Preparation 10, 115 mg) and aminoethoxyamine dihydrochloride (52 mg) were dissolved in pyridine (1.0 ml) and stirred at 60° C. for 5 h and at 90° C. for other 2 h. After evaporation of the solvent, the crude reaction mixture was purified and isolated as described in Example 24 to give the title compound I-ay (140 mg, 86%) as a white powder.

$^1$H-NMR (300 MHz, DMSO-d$_6$/CF$_3$COOH, ppm from TMS): δ 7.78 (br. s, 3H), 6.60 (s, 2H), 4.07 (t, 2H), 3.88 (m, 1H), 3.77 (dd, 1H), 3.53 (dd, 1H), 3.41 (t, 1H), 3.05 (m, 2H), 2.78 (m, 1H), 2.30-0.70 (m, 16H), 1.22 (s, 3H), 1.09 (s, 3H), 0.77 (s, 3H), 0.58 (s, 3H).

Example 26

(E)-3-[3-(R)-Pyrrolidinyl]oxyimino-4,4-dimethyl-6α-hydroxymethyl-androstan-7α,17β-diol fumarate (I-az)

The title compound was obtained in 81% yield following the procedure described in Example 25 and starting from starting from 4,4-dimethyl-6α-hydroxymethyl-7α,17β-dihydroxyandrostan-3-one (Preparation 10, 115 mg) and 3-(R)-pyrrolidinyloxyamine dihydrochloride (Preparation 12, 60 mg).

$^1$H-NMR (300 MHz, DMSO-d$_6$/CF$_3$COOH, ppm from TMS): δ 8.93 (br. s, 1H), 8.81 (br. s, 1H), 6.60 (s, 2H), 4.76 (m, 1H), 3.88 (m, 1H), 3.77 (dd, 1H), 3.54 (dd, 1H), 3.41 (t, 1H), 3.27 (m, 4H), 2.73 (m, 1H), 2.30-0.70 (m, 18H), 1.23 (s, 3H), 1.08 (s, 3H), 0.76 (s, 3H), 0.58 (s, 3H).

Example 27

(E)-3-(4-Piperidyloxyimino)-4,4-dimethyl-6α-hydroxymethylandrostan-7α,17β-diol hydrochloride (I-ba)

4,4-Dimethyl-6α-hydroxymethyl-7α,17β-dihydroxyandrostan-3-one (Preparation 10, 40 mg) and 4-piperidyloxyamine dihydrochloride (Preparation 16, 52 mg) were dissolved in pyridine (1.0 ml) and stirred at RT for 4 days. After evaporation of the solvent, the resulting solid was triturated with DCM/AcOEt 1/1 to give, after filtration, the title compound (40 mg, 86%).

$^1$H-NMR (300 MHz, DMSO-$d_6$/CF$_3$COOH, ppm from TMS): δ 8.50 (br. s, 1H), 8.36 (br. s, 1H), 4.20 (m, 1H), 3.88 (m, 1H), 3.77 (dd, 1H), 3.54 (dd, 1H), 3.40 (t, 1H), 3.07 (m, 4H), 2.79 (m, 1H), 2.20-0.70 (m, 20H), 1.23 (s, 3H), 1.07 (s, 3H), 0.75 (s, 3H), 0.58 (s, 3H).

Example 28

(E)-3-(2-Aminoethoxyimino)-4-(spirocyclopropane)-5-androsten-17β-ol fumarate (I-bb)

The title compound was obtained in 77% yield (90 mg) as described in Example 2 starting from 4-(spirocyclopropane)-17β-hydroxyandrost-5-ene-3-one, (75 mg) and 2-aminoethoxyamine dihydrochloride (88 mg).

$^1$H-NMR (300 MHz, DMSO-$d_6$/CF$_3$COOH, ppm from TMS): δ 7.75 (br. s, 3H), 6.60 (s, 2H), 5.27 (m, 1H), 4.02 (t, 2H), 3.43 (t, 1H), 3.00 (m, 3H), 2.29-0.47 (m, 20H), 1.11 (s, 3H), 0.64 (s, 3H).

Example 29

(E)-3-[3-(R)-Pyrrolidinyl]oxyimino-4-spirocyclopropane androst-5-en-17β-ol fumarate (I-bc)

The title compound was obtained in 91% yield (86 mg) as described in Example 2 starting from 4-(spirocyclopropane)-17β-hydroxyandrost-5-ene-3-one (58 mg) and 3-(R)-pyrrolidinyloxyamine dihydrochloride (Preparation 12, 48 mg).

$^1$H-NMR (300 MHz, DMSO-$d_6$/CF$_3$COOH, ppm from TMS): δ 8.89 (br. s, 1H), 8.78 (br. s, 1H), 6.60 (s, 2H), 5.27 (m, 1H), 4.68 (m, 1H), 3.43 (t, 1H), 3.20 (m, 4H), 2.87 (m, 1H), 2.30-0.48 (m, 22H), 1.11 (s, 3H), 0.64 (s, 3H).

Example 30

(E)-3-(2-Aminoethoxyimino)-4β-ethylandrostan-6,17-dione hydrochloride (I-bd)

To a stirred solution of 4β-ethylandrostan-3,6,17-trione (Preparation 11, 67 mg) in THF (1.1 ml), a solution of 2-aminoethoxyamine dihydrochloride (31 mg) and Na$_2$HPO$_4$.12H$_2$O (15 mg) in H$_2$O (0.55 ml) was added in portions over 45 minutes. After 3.5 h, the solution was evaporated, water was added and the aqueous phase was extracted with THF. The combined organic extracts were washed with brine, dried over Na$_2$SO$_4$ and evaporated to dryness. The crude product was triturated with Et$_2$O and the precipitate was filtered to give the title compound I-bd (34 mg, 42%).

$^1$H-NMR (300 MHz, DMSO-$d_6$, ppm from TMS): 7.73 (br. s, 3H), 4.08 (t, 2H), 3.02 (m, 3H), 2.60-1.14 (m, 20H), 0.93 (s, 3H), 0.80 (t, 3H), 0.78 (s, 3H).

Example 31

(E)-3-[3-(R)-Pyrrolidinyl]oxyimino-4β-ethylandrostan-6,17-dione hydrochloride (I-be)

The title compound was obtained in 58% yield (46 mg) as described in Example 30 starting from 4β-ethylandrostan-3,6,17-trione (Preparation 11, 58 mg) and 3-(R)-pyrrolidinyloxyamine dihydrochloride (Preparation 12, 30 mg).

$^1$H-NMR (300 MHz, DMSO-$d_6$, ppm from TMS): 8.72 (br. s, 2H), 4.75 (m, 1H), 3.40-2.90 (m, 5H), 2.50-1.10 (m, 22H), 0.92 (s, 3H), 0.80 (t, 3H), 0.79 (s, 3H).

Example 32

(E)-3-(2-Aminoethoxyimino)-2α-fluoroandrostan-17β-ol fumarate (I-bf)

2α-Fluorodihydrotestosterone (40 mg) and 2-aminoethoxyamine dihydrochloride (58 mg) were dissolved in pyridine (0.5 ml) and stirred at 70° C. for 5 h. After evaporation of the solvent the crude reaction mixture was purified by flash chromatography (SiO$_2$, CHCl$_3$/MeOH/26% NH$_4$OH 90/10/1). To the concentrated fractions, a stoichiometric amount of fumaric acid in MeOH was added. The precipitate was rinsed with heptane and filtered to give the title compound I-bf in 76% yield.

$^1$H-NMR (300 MHz, DMSO-$d_6$/CF$_3$COOH, ppm from TMS): δ 7.82 (t, 3H), 6.60 (s, 2H), 5.20 (ddd, 1H), 4.15 (t, 2H), 3.41 (t, 1H), 3.08 (m, 2H), 2.87 (m, 1H), 2.30-0.60 (m, 19H), 0.82 (s, 3H), 0.61 (s, 3H).

Example 33

(E)-3-[3-(R)-Pyrrolidinyl]oxyimino-2α-fluoroandrostan-17β-ol fumarate (I-bg)

The title compound was obtained in 91% yield following the procedure described in Example 32 starting from 2α-fluorodihydrotestosterone (40 mg) and 3-(R)-pyrrolidinyloxyamine dihydrochloride (Preparation 12, 68 mg).

$^1$H-NMR (300 MHz, DMSO-$d_6$/CF$_3$COOH, ppm from TMS): δ 8.93 (br. s, 1H), 8.83 (br. s, 1H), 6.60 (s, 2H), 5.20 (ddd, 1H), 4.82 (m, 1H), 3.41 (t, 1H), 3.35-3.10 (m, 4H), 2.78 (m, 1H), 2.30-0.58 (m, 21H), 0.81 (s, 3H), 0.61 (s, 3H).

Example 34

(E)-3-[3-(R)-Pyrrolidinyl]oxyimino-2α-fluoroandrostan-17-one hydrochloride (I-bh)

2α-Fluoroandrostane-3,17-dione (315 mg) and 3-(R)-pyrrolidinyloxyamine dihydrochloride (Preparation 12, 190 mg) were dissolved in pyridine (5 ml) and stirred at RT for 1 h. After evaporation of the solvent, the crude reaction mixture was purified by flash chromatography (SiO$_2$, CHCl$_3$/MeOH/26% NH$_4$OH 90/10/1). To the resulting oil obtained after fractions evaporation, dissolved in a 1/1 mixture of EtOAc/Et$_2$O (20 ml) and cooled with an ice bath, an excess of 2N HCl solution in Et$_2$O was added. The title compound I-bh was obtained, after filtration, as a white solid in 91% yield.

$^1$H-NMR (300 MHz, DMSO-$d_6$/CF$_3$COOH, ppm from TMS): δ 9.02 (br. s, 2H), 5.22 (ddd, 1H), 4.83 (m, 1H), 3.35-2.90 (m, 5H), 2.45-0.75 (m, 21H), 0.84 (s, 3H), 0.77 (s, 3H).

Example 35

(E)-3-[3-(R)-Pyrrolidinyl]oxyimino-2α-fluoro-17β-hydroxyandrostan-6-one fumarate (I-bi)

The title compound was obtained in 97% yield following the procedure described in Example 34 starting from 2α-fluoro-17β-hydroxyandrostan-3,6-dione (Preparation 18, 98 mg) and 3-(R)-pyrrolidinyloxyamine dihydrochloride (Preparation 12, 53 mg). After evaporation of the solvent the crude reaction mixture was purified by flash chromatography ($SiO_2$, $CHCl_3$/MeOH/26% $NH_4OH$ 90/10/1). To the concentrated fractions, a stoichiometric amount of fumaric acid in MeOH was added. The resulting precipitate was rinsed with heptane and filtered to give the title compound I-bi.

$^1$H-NMR (300 MHz, DMSO-$d_6$/$CF_3COOH$, ppm from TMS): δ 10.00 (br. s, 3H), 6.42 (s, 2H), 5.24 (ddd, 1H), 4.81 (m, 1H), 4.50 (br, 1H), 3.50-2.50 (m, 7H), 2.30-0.95 (m, 18H), 0.70 (s, 3H), 0.62 (s, 3H).

Example 36

(E)-3-[3-(R)-Pyrrolidinyl]oxyimino-2α-fluoro-6-(E)-hydroxyiminoandrostan-17β-ol fumarate (I-bj)

The title compound was obtained in 74% yield following the procedure described in Example 34 starting from (E)-3-[3-(R)-pyrrolidinyl]oxyimino-2α-fluoro-17β-hydroxyandrostan-6-one fumarate (Example 35, 73 mg) and hydroxylamine hydrochloride (11 mg). After evaporation of the solvent the crude reaction mixture was purified by flash chromatography ($SiO_2$, $CHCl_3$/MeOH/26% $NH_4OH$ 90/10/1). To the concentrated fractions, a stoichiometric amount of fumaric acid in MeOH was added. The resulting precipitate was rinsed with heptane and filtered to give the title compound I-bj.

$^1$H-NMR (300 MHz, DMSO-$d_6$/$CF_3COOH$, ppm from TMS): δ 9.05 (br. s, 4H), 6.40 (s, 2H), 5.26 (ddd, 1H), 4.81 (m, 1H), 4.50 (br, 1H), 3.50-3.00 (m, 7H), 2.36-0.89 (m, 16H), 0.73 (s, 3H), 0.61 (s, 3H).

Example 37

(E)-3-[3-(R)-Pyrrolidinyl]oxyimino-2α-fluoro-6-(E)-methoxyiminoandrostan-17β-ol fumarate (I-bk)

The title compound was obtained in 56% yield following the procedure described in Example 34 starting from (E)-3-[3-(R)-pyrrolidinyl]oxyimino-2α-fluoro-17β-hydroxyandrostan-6-one fumarate (Example 35, 72 mg) and methoxyamine hydrochloride (14 mg). After evaporation of the solvent the crude reaction mixture was purified by flash chromatography ($SiO_2$, $CHCl_3$/MeOH/26% $NH_4OH$ 90/10/1). To the concentrated fractions, a stoichiometric amount of fumaric acid in MeOH was added. The resulting precipitate was rinsed with heptane and filtered to give the title compound I-bk.

$^1$H-NMR (300 MHz, DMSO-$d_6$/$CF_3COOH$, ppm from TMS): δ 9.50 (br. s, 3H), 6.42 (s, 2H), 5.26 (ddd, 1H), 4.84 (m, 1H), 4.50 (br, 1H), 3.72 (s, 3H), 3.50-3.00 (m, 7H), 2.30-0.91 (m, 18H), 0.75 (s, 3H), 0.61 (s, 3H).

Example 38

(E)-3-[3-(R)-Pyrrolidinyl]oxyimino-4α-fluoroandrostan-17-one fumarate (I-bl)

The title compound was obtained in 64% yield following the procedure described in Example 34 and starting from 4α-fluoroandrostan-3,17-dione (Preparation 17, 23 mg) and 3-(R)-pyrrolidinyloxyamine dihydrochloride (Preparation 12, 14 mg). After evaporation of the solvent the crude reaction mixture was purified by flash chromatography ($SiO_2$, $CHCl_3$/MeOH/26% $NH_4OH$ 90/10/1). To the concentrated fractions, a stoichiometric amount of fumaric acid in MeOH was added. The resulting precipitate was rinsed with heptane and filtered to give the title compound I-bl.

$^1$H-NMR (300 MHz, DMSO-$d_6$/$CF_3COOH$, ppm from TMS): δ 9.50 (br. s, 3H), 6.42 (s, 2H), 5.26 (ddd, 1H), 4.84 (m, 1H), 4.50 (br, 1H), 3.72 (s, 3H), 3.50-3.00 (m, 7H), 2.30-0.91 (m, 18H), 0.75 (s, 3H), 0.61 (s, 3H).

Example 39

(E)-3-(2-Aminoethoxyimino)-4α-hydroxyandrostan-17-one fumarate (I-bm)

(E)-3-(2-aminoethoxyimino)-4α-acetoxyandrostan-17-one hydrochloride was obtained in 85% yield following the procedure described in Example 2 starting from 4α-acetoxyandrostan-3,17-dione (Preparation 19, 120 mg) and 2-aminoethoxyamine dihydrochloride (74 mg).

$^1$H-NMR (300 MHz, DMSO-$d_6$/$CF_3COOH$, ppm from TMS): δ 7.63 (br. s, 3H), 5.06 (d, 1H), 4.06 (t, 2H), 3.17 (m, 1H), 3.00 (m, 2H), 2.38 (m, 1H), 2.08-0.70 (m, 18H), 2.05 (s, 3H), 0.95 (s, 3H), 0.78 (s, 3H).

$K_2CO_3$ (80 mg) was added to a solution of the former 4α-acetoxy derivative in MeOH/water 3/1 (4 ml). The mixture was stirred at RT for 3 h. The solvent was evaporated to dryness and the crude reaction mixture purified by flash chromatography ($SiO_2$, $CHCl_3$/MeOH/26% $NH_4OH$ 90/10/1). To the concentrated fractions, a stoichiometric amount of fumaric acid in MeOH was added. After dilution with a 1/1 mixture of $EtOAc$/$Et_2O$, the resulting precipitate was filtered to give the title compound I-bm (97 mg, 70%) as a white powder.

$^1$H-NMR (300 MHz, DMSO-$d_6$/$CF_3COOH$, ppm from TMS): δ 8.90 (br. s, 4H), 6.40 (s, 2H), 4.40 (br. s, 1H), 4.10 (m, 2H), 3.85 (d, 1H), 3.10 (m, 1H), 3.04 (m, 2H), 2.45-0.58 (m, 19H), 0.89 (s, 3H), 0.77 (s, 3H).

Example 40

(E)-3-[3-(R)-Pyrrolidinyl]oxyimino-4α-hydroxyandrostan-17-one fumarate (I-bn)

(E)-3-[3-(R)-Pyrrolidinyl]oxyimino-4α-acetoxyandrostan-17-one hydrochloride was obtained in 74% yield following the procedure described in Example 2 starting from 4α-acetoxyandrostan-3,17-dione (Preparation 19, 135 mg) and 3-(R)-pyrrolidinyloxyamine dihydrochloride (Preparation 12, 102 mg).

$^1$H-NMR (300 MHz, DMSO-$d_6$/$CF_3COOH$, ppm from TMS): δ 8.98 (br. s, 3H), 5.05 (d, 1H), 4.73 (m, 1H), 3.35-3.00 (m, 5H), 2.38 (m, 1H), 2.10-0.70 (m, 20H), 2.06 (s, 3H), 0.95 (s, 3H), 0.78 (s, 3H).

$K_2CO_3$ (80 mg) was added to a solution of the former 4α-acetoxy derivative in MeOH/water 3/1 (4 ml) and. The mixture was stirred at RT for 5 h. The solvent was evaporated to dryness, and the crude reaction mixture was purified by flash chromatography ($SiO_2$, $CHCl_3$/MeOH/26% $NH_4OH$ 90/10/1). To the concentrated fractions, a stoichiometric amount of fumaric acid in MeOH was added. After dilution with a 1/1 mixture of $EtOAc$/$Et_2O$, the resulting precipitate was filtered to give the title compound I-bn (63 mg, 43%) as a white powder.

$^1$H-NMR (300 MHz, DMSO-d$_6$/CF$_3$COOH, ppm from TMS): δ 8.82 (br. s, 2H), 6.62 (s, 2H), 4.81 (m, 1H), 3.86 (m, 2H), 3.43-3.00 (m, 5H), 2.37 (m, 1H), 2.15-0.60 (m, 20H), 0.89 (s, 3H), 0.77 (s, 3H).

Example 41

(E)-3-[(3-(R)-Pyrrolidinyl)oxyimino]-4-spirocyclopropane-5-androsten-17-one fumarate (I-bo)

The title compound was obtained in 78% yield following the procedure described in Example 5 and starting from 3-(E)-{2-[N-(9-fluorenylmethoxycarbonyl)]-[3-(R)-pyrrolidinyl]oxyimino-4-(spirocyclopropane)}androst-5-en-17-one (Preparation 20, 162 mg).
$^1$H-NMR (300 MHz, DMSO-d$_6$, ppm from TMS): δ 9.00 (br. s, 3H), 6.42 (s, 2H), 5.31 (m, 1H), 4.68 (m, 1H), 3.30-310 (m, 4H), 2.88 (m, 1H), 2.45-0.48 (m, 22H), 1.13 (s, 3H), 0.79 (s, 3H).

Example 42

(E)-3-[(3-(R)-Pyrrolidinyl)oxyimino]-4-spirocyclopentane-5-androsten-17β-ol fumarate (I-bp)

The title compound was obtained in 74% yield following the procedure described in Example 32 and starting from 4-spirocyclopentane-17β-hydroxy-5-androsten-3-one (162 mg) and 3-(R)-pyrrolidinyloxyamine dihydrochloride (Preparation 12, 165 mg). After evaporation of the solvent, the crude reaction mixture was purified by flash chromatography (SiO$_2$, CHCl$_3$/MeOH/26% NH$_4$OH 90/10/1). To the concentrated fractions, a stoichiometric amount of fumaric acid in MeOH was added. The resulting precipitate was rinsed with heptane and filtered to give the title compound I-bp.
$^1$H-NMR (300 MHz, DMSO-d$_6$, ppm from TMS): δ 9.00 (br. s, 3H), 6.42 (s, 2H), 5.54 (m, 1H), 4.78 (m, 1H), 4.50 (br, 1H), 3.47-3.08 (m, 5H), 2.80-0.77 (m, 27H), 0.80 (s, 3H), 0.63 (s, 3H).

Example 43

(E)-3-[(3-(R)-Pyrrolidinyl)oxyimino]-4-spirocyclopentaneandrostan-17β-ol fumarate (I-bq)

The title compound was obtained in 71% yield following the procedure described in Example 32 starting from 4-spirocyclopentane-17β-hydroxyandrostan-3-one (Preparation 21, 92 mg) and 3-(R)-pyrrolidinyloxyamine dihydrochloride (Preparation 12, 70 mg). After evaporation of the solvent, the crude reaction mixture was purified by flash chromatography (SiO$_2$, CHCl$_3$/MeOH/26% NH$_4$OH 90/10/1). To the concentrated fractions, a stoichiometric amount of fumaric acid in MeOH was added. The resulting precipitate was rinsed with heptane and filtered to give the title compound I-bq.
$^1$H-NMR (300 MHz, DMSO-d$_6$, ppm from TMS): δ 9.00 (br. s, 3H), 6.42 (s, 2H), 4.75 (m, 1H), 4.78 (m, 1H), 4.50 (br, 1H), 3.45-2.95 (m, 6H), 2.39-0.52 (m, 29H), 0.91 (s, 3H), 0.61 (s, 3H).

Example 44

(E)-3-[(3-(R)-Pyrrolidinyl)oxyimino]-4-spirocyclopentane-5-androsten-17-one hydrochloride (I-br)

The title compound was obtained in 78% yield following the procedure described in Example 5 starting from 3-(E)-{2-[N-(9-fluorenylmethoxycarbonyl)]-[3-(R)-pyrrolidinyl]oxyimino-4-(spirocyclopentane)}androst-5-en-17-one (Preparation 22, 423 mg). After stirring at RT for 2.5 h, the solution was concentrated and purified by flash chromatography (SiO$_2$, DCM/MeOH/26% NH$_4$OH 90/10/0.1) to give a white foam which was dissolved in DCM (3 ml) and cooled with an ice bath. An excess of 0.2N HCl solution in Et$_2$O was added. The title compound I-bh was obtained, after filtration, as a white solid.
$^1$H-NMR (300 MHz, DMSO-d$_6$, ppm from TMS): δ 9.07 (br. s, 2H), 5.96 (m, 1H), 4.79 (m, 1H), 4.50 (br,1H), 3.45-0.9 (m, 31H), 0.83 (s, 3H), 0.79 (s, 3H).

Example 45

(E)-3-[(3-(R)-Pyrrolidinyl)oxyimino]-4-spirocyclopentaneandrostan-7α,17β-diol fumarate (I-bs)

The title compound was obtained in 62% yield following the procedure described in Example 32 starting from 4-spirocyclopentan-7,17-dihydroxyandrostan-3-one (Preparation 23, 50 mg) and 3-(R)-pyrrolidinyloxyamine dihydrochloride (Preparation 12, 36 mg). After evaporation of the solvent, the crude reaction mixture was purified by flash chromatography (SiO$_2$, CHCl$_3$/MeOH/26% NH$_4$OH 85/15/1.5). To the concentrated fractions, a stoichiometric amount of fumaric acid in MeOH was added. The resulting precipitate was rinsed with heptane and filtered to give the title compound I-bs.
$^1$H-NMR (300 MHz, DMSO-d$_6$, ppm from TMS): δ 9.00 (br. s, 3H), 6.42 (s, 2H), 4.75 (m, 1H), 4.50 (br, 2H), 3.75-2.95 (m, 7H), 2.38-0.75 (m, 27H), 0.88 (s, 3H), 0.59 (s, 3H).

Example 46

(E)-3-(2-Aminoethoxyimino)-4β-methyl-4α,5α-epoxyandrostan-17β-ol fumarate (I-bt)

The title compound was obtained in 62% yield following the procedure described in Example 2 starting from 4β-methyl-4α,5α-epoxy-17β-hydroxyandrostan-3-one (Preparation 24, 50 mg) and 2-aminoethoxyamine dihydrochloride (36 mg). After evaporation of the solvent the crude reaction mixture was purified by flash chromatography (SiO$_2$, CHCl$_3$/MeOH/26% NH$_4$OH 85/15/1.5). A stoichiometric amount of fumaric acid in MeOH was added to the concentrated fractions. The resulting precipitate was rinsed with heptane and filtered to give the title compound I-bt.
$^1$H-NMR (300 MHz, DMSO-d$_6$, ppm from TMS): δ 8.50 (br. s, 4H), 6.42 (s, 2H), 4.50 (br, 1H), 4.18 (m, 2H), 3.43 (t, 1H), 3.09 (m, 2H), 2.53 (m, 1H), 2.23-0.79 (m, 18H), 1.38 (s, 3H), 0.93 (s, 3H), 0.64 (s, 3H).

Example 47

(E)-3-(2-Aminoethoxyimino)-4β-ethyl-4α,5α-epoxyandrostan-17β-ol fumarate (I-bu)

The title compound was obtained in 65% yield following the procedure described in Example 2 and starting from 4β-ethyl-4α,5α-epoxy-17-hydroandrostan-3-one (Preparation 25, 50 mg) and 2-aminoethoxyamine dihydrochloride (50 mg). After evaporation of the solvent the crude reaction mixture was purified by flash chromatography (SiO$_2$, CHCl$_3$/MeOH/26% NH$_4$OH 85/15/1.5). To the concentrated fractions, a stoichiometric amount of fumaric acid in MeOH was added. The resulting precipitate was rinsed with heptane and filtered to give the title compound I-bu.

$^1$H-NMR (300 MHz, DMSO-d$_6$, ppm from TMS): δ 9.50 (br. s, 4H), 6.42 (s, 2H), 4.50 (br, 1H), 4.19 (m, 2H), 2.44 (m, 1H), 3.08 (m, 2H), 2.56 (m, 1H), 2.33-0.82 (m, 20H), 0.94 (s, 3H), 0.85 (t, 3H), 0.64 (s, 3H).

Example 48

(E)-3-(2-Aminoethoxyimino)-4-isopropylandrost-4-en-17β-ol fumarate (I-bv)

The title compound was obtained in 40% yield following the procedure described in Example 32 starting from 4-isopropyl-17β-hydroxyandrost-4-en-3-one (155 mg) and 3-(R)-pyrrolidinyloxyamine dihydrochloride (Preparation 12, 246 mg). After evaporation of the solvent the crude reaction mixture was purified by flash chromatography (SiO$_2$, CHCl$_3$/MeOH/26% NH$_4$OH 90/10/1). To the concentrated fractions, a stoichiometric amount of fumaric acid in MeOH was added. The resulting precipitate was rinsed with heptane and filtered to give the title compound I-bv.
$^1$H-NMR (300 MHz, DMSO-d$_6$, ppm from TMS): δ 9.00 (br. s, 3H), 6.40 (s, 2H), 4.78 (m, 1H), 4.50 (br, 1H), 3.45-2.73 (m, 8H), 2.14-0.98 (m, 19H), 1.14 (d, 3H), 1.11 (d, 3H), 0.99 (s, 3H), 0.65 (s, 3H).

Example 49

(E)-3-[(3-(R)-Pyrrolidinyl)oxyimino]-4α-ethylandrostan-17β-ol fumarate (I-bw)

The title compound was obtained in 90% yield following the procedure described in Example 32 starting from 4α-ethyl-17β-hydroxyandrostan-3-one (Preparation 26, 109 mg) and 3-(R)-pyrrolidinyloxyamine dihydrochloride (Preparation 12, 180 mg). After evaporation of the solvent the crude reaction mixture was purified by flash chromatography (SiO$_2$, CHCl$_3$/MeOH/26% NH$_4$OH 90/10/1). To the concentrated fractions, a stoichiometric amount of fumaric acid in MeOH was added. The resulting precipitate was rinsed with heptane and filtered to give the title compound I-bw.
$^1$H-NMR (300 MHz, DMSO-d$_6$, ppm from TMS): δ 9.00 (br. s, 3H), 6.42 (s, 2H), 4.75 (m, 1H), 4.50 (br, 1H) 3.46-2.83 (m, 6H), 2.10-0.75 (m, 24H), 0.85 (s, 3H), 0.81 (t, 3H), 0.61 (s, 3H).

Example 50

(E)-3-[3-(R)-Pyrrolidinyl]oxyimino-4β-ethyl-6α-hydroxyandrostan-17-one hydrochloride (I-bx)

The title compound was obtained in 90% yield following the procedure described in Example 30 starting from 4β-ethyl-6α-hydroxyandrostan-3,17-dione (Preparation 27, 137 mg) and 3-(R)-pyrrolidinyloxyamine dihydrochloride (Preparation 12, 160 mg). The crude product was triturated with Et$_2$O and the resulting precipitate was filtered to give the title compound I-bx.
$^1$H-NMR (300 MHz, DMSO-d$_6$, ppm from TMS): δ 8.98 (br. s, 2H), 4.76 (m, 1H), 4.42 (d, 1H), 3.70-2.91 (m, 6H), 2.44-0.50 (m, 22H), 0.92 (s, 3H), 0.76 (t, 3H), 0.75 (s, 3H).

Example 51

(E)-3-[3-(R)-Pyrrolidinyl]oxyimino-4,4-dimethylandrostan-5α,17β-diol hydrochloride (I-by)

The title compound was obtained in 51% yield following the procedure described in Example 2 and starting from 4,4-dimethyl-5α,17β-dihydroxyandrostan-3-one (Preparation 28, 33 mg) and 3-(R)-pyrrolidinyloxyamine dihydrochloride (Preparation 12, 69 mg). The crude product was triturated with Et$_2$O and the resulting precipitate was filtered to give the title compound I-by.
$^1$H-NMR (300 MHz, DMSO-d$_6$, ppm from TMS): δ 8.99 (br. s, 2H), 4.74 (m, 1H), 4.38 (d, 1H), 3.89 (s, 1H), 3.46-2.85 (m, 6H), 2.19-0.74 (m, 20H), 1.11 (s, 3H), 1.05 (s, 3H), 1.01 (s, 3H), 0.60 (s, 3H).

Example 52

(E)-3-(2-Aminoethoxyimino)-4-isopropylandrost-4-en-17β-ol fumarate (I-bz)

The title compound was obtained in 40% yield following the procedure described in Example 32 starting from 4-isopropyl-17β-hydroxy-4-androsten-3-one (155 mg) and 3-(R)-pyrrolidinyloxyamine dihydrochloride (Preparation 12, 246 mg). After evaporation of the solvent the crude reaction mixture was purified by flash chromatography (SiO$_2$, CHCl$_3$/MeOH/26% NH$_4$OH 90/10/1). To the concentrated fractions, a stoichiometric amount of fumaric acid in MeOH was added. The resulting precipitate was rinsed with heptane and filtered to give the title compound I-bz.
$^1$H-NMR (300 MHz, DMSO-d$_6$, ppm from TMS): δ 8.98 (br. s, 2H), 4.76 (m, 1H), 4.42 (d, 1H), 3.70-2.91 (m, 6H), 2.44-0.50 (m, 22H), 0.92 (s, 3H), 0.76 (t, 3H), 0.75 (s, 3H).

Preparation 1

3-(E)-{2-[N-(9-Fluorenylmethoxycarbonyl)]aminoethoxyimino}-4,4-dimethylandrost-5-en-17-one STEP 1: To a stirred solution of a mixture of (E)-3-(2-aminoethoxyimino)-4,4-dimethylandrost-5-en-17β-ol (Example 2, 250 mg) and Et$_3$N (0.14 ml) under N$_2$ in DCM (10 ml) at 0° C., 9-fluorenylmethoxycarbonyl chloride (170 mg) was added. After stirring at RT for 15 minutes, water was added and the mixture was extracted with DCM. The organic phase was washed with 5% NaHCO$_3$ dried over Na$_2$SO$_4$ and evaporated to dryness to give 3-(E)-{2-[N-(9-fluorenyl-methoxy-carbonyl)]aminoethoxyimino}-4,4-dimethylandrost-5-en-17β-ol (392 mg, 99%).
$^1$H-NMR (300 MHz, DMSO-d$_6$, ppm from TMS): δ 7.90-7.20 (m, 9H), 5.54 (m, 1H), 4.44 (m, 1H), 4.25 (m, 3H), 3.95 (m, 2H), 3.42 (m, 1H), 3.22 (m, 2H), 2.76 (m, 1H), 2.30-0.77 (m, 16H), 1.24 (s, 3H), 1.16 (s, 3H), 0.68 (s, 3H), 0.60 (s, 3H).
STEP 2: To a stirred solution of 3-(E)-{2-[N-(9-fluorenylmethoxycarbonyl)]-aminoethoxyimino}-4,4-dimethylandrost-5-en-17β-ol (389 mg) in DCM (8 ml) under N$_2$, NMO (114 mg), TPAP (11.4 mg) and 4 Å molecular sieves (325 mg) were added. The mixture was stirred for 1 h and then SiO$_2$ was added. The mixture was purified by flash chromatography (SiO$_2$, DCM/MeOH/26% NH$_4$OH 90/10/1) to give 3-(E)-{2-[N-(9-fluorenylmethoxycarbonyl)]aminoethoxyimino}-4,4-dimethylandrost-5-en-17-one (343 mg, 88%).
$^1$H-NMR (300 MHz, DMSO-d$_6$, ppm from TMS): δ 8.00-7.20 (m, 9H), 5.57 (m, 1H), 4.22 (m, 3H), 3.97 (m, 2H), 3.22 (m, 2H), 2.76 (m, 1H), 2.45-0.60 (m, 16H), 1.25 (s, 3H), 1.17 (s, 3H), 0.73 (s, 3H), 0.67 (s, 3H).

Preparation 2

3-(E)-{2-[N-(9-Fluorenylmethoxycarbonyl)]aminoethoxyimino}-4,4-dimethylandrostan-17-one The title compound was obtained (343 g, 88%) following the procedure described in Preparation 1, (Step 2) starting from 3-(E)-{2-[N-(9-fluorenylmethoxycarbonyl)]aminoethoxyimino}-4,4-dimethyl-androstan-17β-ol (391 mg).

$^1$H-NMR (300 MHz, DMSO-d$_6$, ppm from TMS): δ 7.90-7.20 (m, 9H), 4.23 (m, 3H), 3.95 (m, 2H), 3.34 (m, 1H), 3.23 (m, 2H), 2.97 (m, 1H), 2.40-0.40 (m, 19H), 1.03 (s, 3H), 0.95 (s, 3H), 0.88 (s, 3H), 0.72 (s, 3H).

Previously, 3-(E)-{2-[N-(9-fluorenylmethoxycarbonyl)]aminoethoxyimino}-4,4-dimethyl-androstan-17β-ol was obtained following the procedure described in Preparation 1, (Step 1) starting from (E)-3-(2-aminoethoxyimino)-4,4-dimethylandrostan-17β-ol (Ex. 7, 277 mg) and 9-fluorenylmethoxycarbonyl chloride (190 mg) in 93% yield (409 g).

$^1$H-NMR (300 MHz, DMSO-d$_6$, ppm from TMS): δ 7.90-7.20 (m, 9H), 4.38 (d, 1H), 4.22 (m, 3H), 3.94 (m, 2H), 3.23 (m, 2H), 2.96 (m, 1H), 2.05-0.40 (m, 19H), 1.02 (s, 3H), 0.94 (s, 3H), 0.87 (s, 3H), 0.60 (s, 3H).

Preparation 3

3-(E)-{3-[N-(9-Fluorenylmethoxycarbonyl)]aminopropoxyimino}-(4,4-dimethylandrostan-17-one The title compound was obtained (194 g, 82%) following the procedure described in Preparation 1, (Step 2) starting from 3-(E)-{3-[N-(9-fluorenylmethoxycarbonyl)]aminopropoxyimino}-4,4-dimethyl-androstan-17β-ol (237 mg).

$^1$H-NMR (300 MHz, DMSO-d$_6$, ppm from TMS): δ 7.96-7.20 (m, 9H), 4.25 (m, 3H), 3.94 (m, 2H), 3.05 (m, 2H), 2.96 (m, 1H), 2.42-0.52 (m, 21H), 1.04 (s, 3H), 0.97 (s, 3H), 0.92 (s, 3H), 0.74 (s, 3H).

Previously, 3-(E)-{3-[N-(9-fluorenylmethoxycarbonyl)]aminopropoxyimino}-4,4-dimethyl-androstan-17β-ol was obtained following the procedure described in Preparation 1, (Step 1) starting from 3-(E)-(3-aminopropoxyimino)-4,4-dimethylandrostan-17β-ol (Ex. 9, 187 mg) and 9-fluorenylmethoxycarbonyl chloride (124 mg) in 81% yield (238 g).

$^1$H-NMR (300 MHz, DMSO-d$_6$, ppm from TMS): δ 7.93-7.20 (m, 9H), 4.37 (d, 1H), 4.23 (m, 3H), 3.93 (m, 2H), 3.36 (m, 1H), 3.04 (m, 2H), 2.95 (m, 1H), 2.09-0.45 (m, 21H), 1.03 (s, 3H), 0.96 (s, 3H), 0.90 (s, 3H), 0.59 (s, 3H).

Preparation 4

3-(E)-{1-[N-(9-Fluorenylmethoxycarbonyl)]-3-(R)-pyrrolidinyloxyimino}-4,4-dimethylandrostan-17-one The title compound was obtained (127 g, 87%) following the procedure described in Preparation 1, (Step 2) starting from 3-(E)-{1-[N-(9-fluorenylmethoxycarbonyl)]-3-(R)-pyrrolidinyloxyimino}-4,4-dimethylandrostan-17β-ol (147 mg).

$^1$H-NMR (300 MHz, DMSO-d$_6$, ppm from TMS): δ 7.94-7.25 (m, 8H), 4.64 (m, 1H), 4.28 (m, 3H), 3.49-2.83 (m, 5H), 2.43-0.60 (m, 21H), 1.06 (s, 3H), 0.98 (s, 3H), 0.92 (s, 3H), 0.75 (s, 3H).

Previously, 3-(E)-{1-[N-(9-fluorenylmethoxycarbonyl)]-3-(R)-pyrrolidinyloxyimino}-4,4-dimethylandrostan-17β-ol was obtained following the procedure described in Preparation 1, (Step 1) starting from (E) 3-[3-(R)-pyrrolidinyl]oxyimino-4,4-dimethylandrostan-17β-ol (Ex. 11, 115 mg) and 9-fluorenylmethoxycarbonyl chloride (72 mg) in 84% yield (152 g).

$^1$H-NMR (300 MHz, DMSO-d$_6$, ppm from TMS): δ 7.94-7.24 (m, 8H), 4.64 (m, 1H), 4.42 (d, 1H), 4.27 (m, 3H), 3.50-2.80 (m, 6H), 2.14-0.50 (m, 21H), 1.05 (s, 3H), 0.97 (s, 3H), 0.90 (s, 3H), 0.59 (s, 3H).

Preparation 5

5α,6α,17β-Trihydroxy-4,4-dimethylandrostan-3-one

To a stirred solution of 17β-hydroxy-4,4-dimethylandrost-5-en-3-one (1.00 g) in THF (100 ml) and pyridine (7.1 ml), 0.16 M OsO$_4$ in water (35 ml) was added. After stirring at RT for 24 h the reaction mixture was quenched by addition of 40% NaHSO$_3$ in water (5 ml). After stirring for 4 h, brine was added and the mixture was extracted with EtOAc. The combined organic extracts were washed with brine, dried over Na$_2$SO$_4$, filtered and evaporated to dryness. The mixture was purified by flash chromatography (SiO$_2$, n-hexane/DCM/acetone 60/20/20) to give the title compound (610 mg, 55%).

$^1$H-NMR (300 MHz, DMSO-d$_6$, ppm from TMS): δ 4.42 (d, 1H), 4.41 (d, 1H), 3.90 (s, 1H), 3.83 (m, 1H), 3.42 (m, 1H), 2.84 (m, 1H), 2.08-0.80 (m, 16H), 1.23 (s, 3H), 1.15 (s, 3H), 0.70 (s, 3H), 0.58 (s, 3H).

Preparation 6

4,4-Dimethylandrostane-3,6,17-trione

STEP 1: To a stirred solution of 17β-hydroxy-4,4-dimethylandrost-5-en-3-one (408 mg) in THF (12 ml) at −15° C., under N$_2$, was added 1M BH$_3$.THF complex in THF (6.44 ml). The mixture was then stirred at RT overnight. H$_2$O (5 ml) was cautiously added dropwise followed by NaBO$_3$.4H$_2$O (330 mg). After stirring at RT overnight, the mixture was filtered. The solid was washed with THF and then discarded. The liquid phases were separated and the aqueous layer was saturated with NaCl and extracted with THF (3×200 ml). The combined organic extracts were dried over NaCl and Na$_2$SO$_4$, filtered and evaporated to dryness. The crude product was purified by flash chromatography (SiO$_2$, DCM/MeOH 97/3) to give 4,4-dimethylandrostan-3β,6α,17β-triol (137 mg, 32%).

$^1$H-NMR (300 MHz, DMSO-d$_6$, ppm from TMS): δ 4.39 (d, 1H), 4.20 (d, 1H), 3.95 (d, 1H), 3.69 (m, 1H), 3.40 (m, 1H), 2.91 (m, 1H), 1.88-0.47 (m, 18H), 1.19 (s, 3H), 0.84 (s, 3H), 0.79 (s, 3H), 0.60 (s, 3H).

STEP 2: Following the procedure described in Preparation 1, (Step 2) and starting from 4,4-dimethylandrostan-3β,6α,17β-triol (127 mg) and TPAP (6.5 mg) 4,4-dimethylandrostan-3,6,17-trione was obtained (99 mg, 80%).

$^1$H-NMR (300 MHz, DMSO-d$_6$, ppm from TMS): δ 2.86 (m, 1H), 2.65 (s, 1H), 2.47-1.04 (m, 16H), 1.37 (s, 3H), 1.05 (s, 3H), 0.99 (s, 3H), 0.79 (s, 3H). α β

Preparation 7

3-(E)-{1-[N-(9-Fluorenylmethoxycarbonyl)]-3-(R)-pyrrolidinyloxyimino}-4,4-dimethyl-5α-hydroxyandrostan-6,17-dione Following the procedure described in Preparation 1, (Step 1) and starting from 3-(E)-[3-(R)-pyrrolidinyl]oxyimino-4,4-dimethylandrostan-5α,6α,17β-triol (Example 17, 83 mg) and 9-fluorenylmethoxycarbonyl chloride (56 mg), 3-(E)-{1-[N-(9-fluorenylmethoxycarbonyl)]-3-(R)-pyrrolidinyloxyimino}-(4,4-dimethylandrostan-5α,6α,17β-triol was obtained (81 mg, 64%) as a crude product. The latter was oxidized without any further purification following the procedure described in Preparation 1, (Step 2) to give the title compound in 88% yield (51 mg).

$^1$H-NMR (300 MHz, DMSO-d$_6$, ppm from TMS): δ 7.95-7.25 (m, 8H), 5.46 (s, 1H), 4.63 (m, 1H), 3.50-1.05 (m, 24H), 1.40 (s, 3H), 1.23 (s, 3H), 0.96 (s, 3H), 0.75 (s, 3H).

Preparation 8

5α,6α-Epoxy-4,4-dimethyl-17β-hydroxyandrostan-3-one mCPBA (1.17 g) was added to a stirred solution of 17β-hydroxy-4,4-dimethylandrost-5-en-3-one (1.00 g) in DCM (30 ml). After 8 h at RT, a 10% Na$_2$SO$_3$ aqueous solution was added. The mixture was neutralized by addition of 5% aqueous NaHCO$_3$ solution and was extracted with DCM (3×100 ml). The combined organic extracts were washed with H$_2$O, dried over Na$_2$SO$_4$, and evaporated to dryness. The mixture was purified by flash chromatography (SiO$_2$, n-hexane/EtOAc 70/30) to give 5α,6α-epoxy-4,4-dimethyl-17β-hydroxyandrostan-3-one (230 mg, 23%).

$^1$H-NMR (300 MHz, acetone-d$_6$, ppm from TMS): δ 3.55 (m, 2H), 3.09 (d, 1H), 2.77-0.80 (m, 17H), 1.21 (s, 3H), 1.03 (s, 3H), 0.80 (s, 3H), 0.70 (s, 3H).

Preparation 9

4,4-Dimethyl-6α-hydroxymethyl-17β-hydroxyandrostan-3,7-dione

STEP 1: To a suspension of 4,4-dimethyl-17β-hydroxyandrost-5-en-3-one (3.34 g) in DMF (30 ml), imidazole (1.40 g) and tert-butyldimethylsilyl chloride (3.15 g) were added. After stirring the mixture overnight at RT, water was added, and stirring was continued for 30 min at 0° C. The formed solid was filtered and, after drying, 4,4-dimethyl-17β-tert-butyldimethylsilyloxyandrost-5-en-3-one was obtained (4.0 g, 93% yield).

$^1$H-NMR (300 MHz, acetone-d$_6$, ppm from TMS): δ 5.60 (1H, m), 3.63 (1H, t), 2.65-1.00 (17H, m), 1.22 (3H, s), 1.18 (3H, s), 0.87 (9H, s), 0.85 (3H, s), 0.77 (3H, s), 0.02 (3H, s), 0.01 (3H, s).

STEP 2: 4,4-Dimethyl-17β-tert-butyldimethylsilyloxyandrost-5-en-3-one (4.0 g) was dissolved in toluene (235 ml). Ethylene glycol (9.3 ml) and PTSA (124 mg) were added and the mixture was refluxed for 7.5 h, removing water with a Dean-Stark trap. After cooling, water was added and the mixture was extracted with EtOAc. The organic phase was washed with 5% NaHCO$_3$, brine then dried over Na$_2$SO$_4$ and evaporated to dryness to give 3,3-(ethylenedioxy)-4,4-dimethyl-17β-tert-butyldimethylsilyloxy-androst-5-ene (4.4 g, 100%) which was used without purification in the next step.

$^1$H-NMR (300 MHz, acetone-d$_6$, ppm from TMS): δ 5.60 (1H, m), 3.95-3.90 (4H, m), 3.60 (1H, m), 2.65-1.00 (17H, m), 1.22 (3H, s), 1.18 (3H, s), 0.87 (9H, s), 0.85 (3H, s), 0.77 (3H, s), 0.02 (3H, s), 0.01 (3H, s).

STEP 3: To a solution of the former (4.4 g) and NHS (4.2 g) in acetone (70 ml), Na$_2$CrO$_7$ (3.3 g) was added portionwise at 45° C. After stirring overnight the mixture was cooled, then water (300 ml) and ice were added. The resulting suspension was stirred for 1 h. The solid obtained was filtered and dried at 45° C. to give 3,3-(ethylenedioxy)-4,4-dimethyl-17β-tert-butyldimethylsilyloxyandrost-5-en-7-one (3.9 g, 85% yield), which was used without purification in the next step.

$^1$H-NMR (300 MHz, acetone-d$_6$, ppm from TMS): δ 5.60 (1H, m), 3.95-3.90 (4H, m), 3.60 (1H, m), 2.65-1.00 (15H, m), 1.22 (3H, s), 1.18 (3H, s), 0.87 (9H, s), 0.85 (3H, s), 0.77 (3H, s), 0.02 (3H, s), 0.01 (3H, s).

STEP 4: To a solution of 3,3-(ethylenedioxy)-4,4-dimethyl-17β-tert-butyldimethyl-silyloxyandrost-5-en-7-one (3.9 g) in dioxane (270 ml), Pd/C 10% (390 mg) was added, and then the mixture was hydrogenated at RT for 72 h. The catalyst was filtered off, washed with EtOAc and the organic phase evaporated under reduced pressure. The crude reaction mixture was purified by flash chromatography (SiO$_2$, n-hexane/EtOAc/toluene 90/5/5) to give 3,3-(ethylenedioxy)-4,4-dimethyl-17β-tert-butyldimethyl-silyloxyandrostan-7-one (2.44 g, 63% yield).

$^1$H-NMR (300 MHz, acetone-d$_6$, ppm from TMS): δ 3.95-3.90 (4H, m), 3.60 (1H, m), 2.65-1.00 (18H, m), 1.22 (3H, s), 1.18 (3H, s), 0.87 (9H, s), 0.85 (3H, s), 0.77 (3H, s), 0.02 (3H, s), 0.01 (3H, s).

STEP 5: To a solution of 2,6-diphenylphenol (7.60 g) in DCM (100 ml), trimethylaluminum (8 ml, 2M in hexanes) was added at RT. After 1 h the mixture was cooled to 0° C., and a solution of trioxane (460 mg) in DCM (2 ml) added. After 1 h the mixture was cooled to −78° C. and dropped to a lithium enolate solution (prepared from 3,3-(ethylenedioxy)-4,4-dimethyl-17β-tert-butyldimethylsilyloxy-androstan-7-one (2.44 g) in THF (25 ml) and LDA (1.5 M in cyclohexane, 21.2 ml) at −78° C.). After stirring overnight at −20° C., the reaction was quenched by addition of NaHCO$_3$ saturated solution. The mixture was filtered on a celite pad and rinsed with DCM. The filtrate was washed with water, dried over Na$_2$SO$_4$ and concentrated. TBAF (5.6 ml, 1M in THF) was added and the mixture stirred at RT for 1.5 h. The resulting solution was washed with water, dried over Na$_2$SO$_4$ and evaporated to dryness. The resulting residue was purified by flash chromatography (SiO$_2$, n-hexane/EtOAc 75/25) to give 3,3-(ethylenedioxy)-4,4-dimethyl-6α-hydroxymethyl-17β-tert-butyl-dimethylsilyloxyandrostan-7-one (1.26 g, 50% yield).

$^1$H-NMR (300 MHz, DMSO-d$_6$, ppm from TMS): δ 3.95-3.90 (4H, m), 3.60 (1H, m), 2.75 (2H, m), 2.65-1.00 (16H, m), 1.22 (3H, s), 1.18 (3H, s), 0.87 (9H, s), 0.85 (3H, s), 0.77 (3H, s), 0.02 (3H, s), 0.01 (3H, s).

STEP 6: 3,3-(ethylenedioxy)-4,4-dimethyl-6α-hydroxymethyl-17β-tert-butyl-dimethylsilyloxyandrostan-7-one (100 mg) was dissolved in dioxane (2 ml) then 1N HCl (2 ml) was added and the mixture stirred at RT for 5.5 h. 5% NaHCO$_3$ was added and the solvent evaporated to dryness. The water phase was extracted with DCM, dried over Na$_2$SO$_4$ and evaporated to dryness to give 4,4-dimethyl-6α-hydroxymethyl-17β-hydroxyandrostan-3,7-dione in 95% yield.

$^1$H-NMR (300 MHz, DMSO-d$_6$, ppm from TMS): δ 4.33 (1H, t), 4.28 (1H, m), 3.85-3.80 (1H, m), 2.70 (2H, m), 2.20-0.80 (17H, m), 1.12 (3H, s), 1.01 (3H, s), 0.83 (3H, s), 0.79 (3H, s).

Preparation 10

4,4-dimethyl-6α-hydroxymethyl-7α,17β-dihydroxyandrostan-3-one

To a stirred solution of 3,3-(ethylenedioxy)-4,4-dimethyl-6α-hydroxymethyl-17β-tert-butyldimethylsilyloxyandrostan-7-one (Preparation 9—Step 5, 1.0 g) in MeOH (40 ml) NaBH$_4$ (140 mg) was added at 0° C. and the mixture was warmed to RT. After 1 h the mixture was quenched by addition of 5% NaH$_2$PO$_4$ and extracted with DCM. The combined organic extracts were washed with brine, dried over Na$_2$SO$_4$ and evaporated to dryness. The residue was dissolved in dioxane (20 ml) and 1N HCl (10 ml) was added. The resulting mixture was stirred at RT for 1 h and evaporated to dryness. The residue was purified by flash chromatography (SiO$_2$, n-hexane/AcOEt 25/75) to give 4,4-dimethyl-6α-hydroxymethyl-7α,17β-dihydroxyandrostan-3-one in 76% yield.

$^1$H-NMR (300 MHz, DMSO-d$_6$, ppm from TMS): δ 4.33 (1H, t), 4.28 (2H, m), 3.85-3.80 (2H, m), 2.70 (2H, m), 2.20-0.80 (17H, m), 1.12 (3H, s), 1.01 (3H, s), 0.83 (3H, s), 0.79 (3H, s).

Preparation 11

4β-Ethylandrostan-3,6,17-trione

STEP 1: Iodoethane (1.60 g) in dry tert-butanol (150 ml) was added dropwise under N$_2$, over 6 h to a vigorously stirred solution heated to reflux, of testosterone (3.00 g) and potassium tert-butoxide (1.75 g) in dry tert-butanol (100 ml). The mixture was refluxed for further 3 h. After cooling to RT, the mixture was quenched by addition of a saturated aqueous NH$_4$Cl solution (170 ml). After stirring for 10 minutes, tert-butanol was evaporated and the mixture was extracted with toluene. The combined organic extracts were washed with brine, dried over Na$_2$SO$_4$, filtered and evaporated to dryness. The mixture was purified by flash chromatography (SiO$_2$, n-hexane/EtOAc 70/30) to give 17β-hydroxy-4-ethylandrost-4-ene-3-one (1.68 g, 51%).

$^1$H-NMR (300 MHz, DMSO-d$_6$, ppm from TMS): δ 4.46 (d, 1H), 3.41 (m, 1H), 2.63 (m, 1H), 2.45-0.13 (m, 20H), 1.12 (s, 3H), 0.78 (t, 3H), 0.67 (s, 3H).

STEP 2: A stirred solution of the latter (1.05 g) under N$_2$, together with Ac$_2$O (0.87 ml), pyridine (0.22 ml) and acetyl chloride (1.8 ml) was refluxed for 1.5 h. After cooling to RT, EtOAc was added and the solution was washed with H$_2$O, 5% NaHCO$_3$ solution, and brine. The organic phase was dried over Na$_2$SO$_4$, filtered and evaporated to dryness. The mixture was purified by flash chromatography (SiO$_2$, n-hexane/EtOAc 90/10) to give 3,17β-diacetoxy-4-ethylandrosta-3,5-diene (1.14 g, 86%).

$^1$H-NMR (300 MHz, DMSO-d$_6$, ppm from TMS): δ 5.61 (m, 1H), 4.52 (t, 1H), 2.38-0.98 (m, 19H), 2.13 (s, 3H), 1.91 (s, 3H), 0.91 (s, 3H), 0.82 (t, 3H), 0.77 (s, 3H).

STEP 3: To a stirred solution of 3,17β-diacetoxy-4-ethylandrosta-3,5-diene (1.08 g) in EtOH/H$_2$O 95/5 (13.7 ml), mCPBA (1.0 g) was added. After 8 h at RT, DCM (150 ml) was added and the mixture was washed with 10% Na$_2$SO$_3$ aqueous solution, 5% aqueous NaHCO$_3$ solution, and brine. The organic phase was dried over Na$_2$SO$_4$, and evaporated to dryness. The crude reaction mixture was purified by flash chromatography (SiO$_2$, n-hexane/EtOAc 60/40) to give a mixture 6α-hydroxy-17β-acetoxy-4-ethylandrost-4-en-3-one and 6β-hydroxy-17β-acetoxy-4-ethylandrost-4-en-3-one (0.53 g, 52%).

STEP 4: To a solution of a 6α-hydroxy-17β-acetoxy-4-ethylandrost-4-en-3-one and 6β-hydroxy-17β-acetoxy-4-ethylandrost-4-en-3-one (510 mg) in acetone (34 ml) cooled at 0° C., Jones reagent (1.1 ml) was added dropwise. 5 min after completion of the addition, DCM (140 ml) was added and the mixture was washed with 10% Na$_2$SO$_3$ aqueous solution, 5% aqueous NaHCO$_3$ solution, and brine. The organic phase was dried over Na$_2$SO$_4$, and evaporated to dryness to give 17β-acetoxy-4-ethylandrost-4-en-3,6-dione (465 g, 92%).

$^1$H-NMR (300 MHz, Acetone-d$_6$, ppm from TMS): δ 4.61 (t, 1H), 2.59-1.20 (m, 19H), 1.99 (s, 3H), 1.13 (s, 3H), 0.90 (t, 3H), 0.87 (s, 3H).

STEP 5: Li (252 mg) was added in small pieces to liquid NH$_3$ (80 ml) at −35° C. 17β-acetoxy-4-ethylandrost-4-en-3,6-dione (465 mg) in dry THF (12 ml) was added dropwise to the former solution. The mixture was stirred at −35° C. for 10 minutes and NH$_4$Cl (5.0 g) was careful added. The NH$_3$ was evaporated at RT under N$_2$ flow. Water was added and the mixture was extracted with EtOAc. The combined organic extracts were washed with brine, dried, filtered and evaporated to dryness. The mixture was purified by flash chromatography (SiO$_2$, n-hexane/EtOAc 30/70) to give a mixture of 3α,17β-dihydroxy-4β-ethylandrostan-6-one and 3β,17β-dihydroxy-4β-ethylandrostan-6-one (193 mg, 48%).

STEP 6: To a solution of 3α,17β-dihydroxy-4β-ethylandrostan-6-one and 3β-17β-dihydroxy-4β-ethylandrostan-6-one (179 mg) in DCM (6.7 ml) under N$_2$, NMO (190 mg), TPAP (9.5 mg) and 4 Å molecular sieves (270 mg) were added. The mixture was stirred for 15 min and then SiO$_2$ was added. The mixture was purified by flash chromatography (SiO$_2$, n-hexane/EtOAc 70/30) to give the title compound (140 mg, 79%).

$^1$H-NMR (300 MHz, Acetone-d$_6$, ppm from TMS): δ 2.90-1.20 (m, 21H), 1.16 (s, 3H), 0.89 (s, 3H), 0.85 (t, 3H).

Preparation 12

3(R)-Pyrrolidinyloxyamine dihydrochloride

STEP 1: Di-tert-butyl dicarbonate (21.5 g) was added to a solution of 3-(S)-hydroxypyrrolidine hydrochloride (15.0 g) and NEt$_3$ (27.3 ml) in MeOH (135 ml) at 0° C. After stirring at RT for 6 h, the solvent was evaporated. The residue was diluted with DCM, washed with water and the organic phase was evaporated to dryness to give N-tert-butoxycarbonyl-3-(S)-pyrrolidinol (21.4 g, 95%) which was used without purification in the next step.

$^1$H-NMR (300 MHz, DMSO-d$_6$, ppm from TMS): δ 4.87 (1H, d), 4.19 (1H, m), 3.30-3.00 (4H, m), 1.90-1.60 (2H, m), 1.37 (9H, s).

STEP 2: To a solution of the latter (10.0 g) and NEt$_3$ (8.2 ml) in DCM (150 ml) at 0° C., methanesulfonyl chloride (4.34 ml) was added. After stirring at RT for 3 h, the reaction mixture was poured into ice/water and extracted with DCM. The organic phase was washed with 5% aqueous NaHCO$_3$, water and brine, was dried and was evaporated to dryness to give an oil which solidified after standing overnight in the refrigerator. The solid was triturated with Et$_2$O to give N-tert-butoxycarbonyl-3-(S)-pyrrolidinyl methanesulfonate (13.0 g, 92%) as a light yellow solid.

$^1$H-NMR (300 MHz, DMSO-d$_6$, ppm from TMS): δ 5.23 (1H, m), 3.60-3.10 (4H, m), 3.23 (3H, s), 2.11 (2H, m), 1.39 (9H, s).

STEP 3: To a suspension of KOH powder (4.86 g) in DMSO (250 ml) under vigorous stirring, benzophenone oxime (7.86 g) was added. After stirring at RT for 30 min, a solution of N-tert-butoxy-carbonyl-3-(S)-pyrrolidinyl methanesulfonate (10.0 g) in DMSO (70 ml) was added. After 18 h at RT the reaction was poured into iced water (900 ml) and extracted with Et$_2$O. The combined organic layers were washed with water, brine, dried and the solvent was evaporated. Benzophenone O-[(R)-3-pyrrolidinyl]oxime was obtained (13.0 g, 96%) as a white solid and used without any further purification in the next step.

$^1$H-NMR (300 MHz, DMSO-d$_6$, ppm from TMS): δ 7.50-7.20 (10H, m), 4.84 (1H, m), 3.50-3.00 (4H, m), 2.01 (2H, m), 1.38 (9H, s).

STEP 4: The latter was suspended in 6N HCl (250 ml) and the mixture was refluxed for 2 h. After cooling, the reaction mixture was extracted with Et$_2$O. The aqueous layer was evaporated to give a crude brown solid, which was refluxed for 2 h in absolute EtOH (255 ml) in the presence of 0.34 g of activated carbon. The solid obtained after evaporation was crystallized from 96% EtOH (40 ml) to 3-(R)-pyrrolidinyloxyamine dihydrochloride (2.98 g, 72%), as an off white solid.

$^1$H-NMR (300 MHz, DMSO-d$_6$, ppm from TMS): δ 11.22 (3H, bb), 9.74 (1H, bb), 9.54 (1H, bb), 4.98 (1H, m), 3.60-3.00 (4H, m), 2.40-2.00 (2H, m).

Preparation 13

2-N-Methylaminoethoxyamine dihydrochloride

STEP 1: To a suspension of KOH (19.7 g) in DMSO (200 ml), under vigorous stirring, benzophenone oxime (20.2 g) was added. A solution of N-methyl-2-chloroethylamine hydrochloride (5.2 g) in DMSO (40 ml) was added dropwise. After 2.5 hrs at RT the reaction was poured into ice/water (400 ml), acidified with 37% HCl to pH 2.5 and rinsed with Et$_2$O. The aqueous layer was treated with powdered KOH to pH 10 and extracted three times with Et$_2$O; the combined organic layers were washed with water, brine, dried over Na$_2$SO$_4$ and the solvent was evaporated. Purification by flash chromatography (SiO$_2$, CHCl$_3$/MeOH/AcOH from 9/1/0.1 to 7/3/0.3) gave benzophenone O-(2-N-methylaminoethyl)oxime (4.65 g, 62%) as a viscous oil.

$^1$H-NMR (300 MHz, DMSO-d$_6$, ppm from TMS): δ 7.51-7.25 (10H, m), 4.13 (2H, t), 2.72 (2H, t), 2.26 (3H, s), 1.60 (1H, bb).

STEP 2: The latter was suspended in 6N HCl (24 ml) and the mixture was refluxed for 2 hrs. The reaction was cooled and extracted with Et$_2$O. The aqueous layer was evaporated to dryness to give 2-N-methylaminoethoxyamine dihydrochloride (1.78 g, 80%) as a hygroscopic white solid.

$^1$H-NMR (300 MHz, DMSO-d$_6$, ppm from TMS): δ 10.5 (5H, bb), 4.26 (2H, t), 3.22 (2H, t), 2.55 (3H, s).

Preparation 14

3-Methylamino-propoxyamine dihydrochloride

STEP 1: Benzophenone O-(3-methylamino-propyl)oxime was prepared in 62% yield from benzophenone oxime and N-methyl-3-chloropropylamine hydrochloride by the procedure described above for the preparation of benzophenone O-(2-N-methylaminoethyl)oxime (Preparation 13, Step 1).

$^1$H-NMR (300 MHz, DMSO-d$_6$, ppm from TMS): δ 7.50-7.20 (m, 10H), 4.14 (t, 2H), 2.45 (t, 2H), 2.21 (s, 3H), 1.72 (m, 2H), 1.45 (br. s, 1H).

STEP 2: 3-N-Methylamino-propoxyamine dihydrochloride was prepared in 80% yield from benzophenone O-(3-N-methylaminopropyl)oxime by the procedure described in Preparation 13, Step 2.

$^1$H-NMR (300 MHz, DMSO-d$_6$, ppm from TMS): δ 11.08 (3H, bb), 9.10 (2H, bb), 4.10 (2H, t), 2.91 (2H, m), 2.50 (3H, s), 1.96 (2H, m).

Preparation 15

3-(S)-Pyrrolidinyloxyamine dihydrochloride

STEP 1: (R)-N-tert-butoxycarbonyl-3-pyrrolidinol was obtained following the procedure described in Preparation 12—Step 1 starting from (R)-3-pyrrolidinol.

$^1$H-NMR (300 MHz, DMSO-d$_6$, ppm from TMS): δ 4.98 (1H, d), 4.19 (1H, m), 3.30-3.00 (4H, m), 1.90-1.60 (2H, m), 1.37 (9H, s).

STEP 2: To a solution of (R)-N-tert-butoxycarbonyl-3-pyrrolidinol (4.00 g), triphenylphosphine (11.80 g) and N-hydroxyphthalimide (7.40 g) in THF (280 ml) at 0° C., 1,1'-(azodicarbonyl)dipiperidine (12.6 g) was added. After stirring at RT for 27 h, the solvent was evaporated and the crude product was purified by flash chromatography (SiO$_2$, DCM/n-hexane/acetone 5/4/1) to give (S)-1-tert-butoxycarbonyl-3-O-phthalimidoxypyrrolidine (2.50 g, 35%).

$^1$H-NMR (300 MHz, DMSO-d$_6$, ppm from TMS): δ 7.86 (m, 4H), 4.89 (1H, m), 3.64-3.30 (m, 4H), 2.20-1.90 (m, 2H), 1.41 (s, 9H).

STEP 3: To a solution of (S)-1-tert-butoxycarbonyl-3-phthalimidoxypyrrolidine (2.50 g) in MeOH (30 ml), hydrazine hydrate (0.45 ml) was added and the mixture was heated to reflux for 6 hr. After cooling and stirring at RT for 15 min, the mixture was filtered. The filtrate was evaporated to dryness and purified by flash chromatography (SiO$_2$, DCM/MeOH 9/1) to give to give (S)-1-tert-butoxycarbonyl-3-pyrrolidinyloxyamine (1.49 g).

$^1$H-NMR (300 MHz, DMSO-d$_6$, ppm from TMS): δ 4.87 (1H, d), 4.19 (1H, m), 3.30-3.00 (4H, m), 1.90-1.60 (2H, m), 1.37 (9H, s).

STEP 4: (S)-1-tert-Butoxycarbonyl-3-pyrrolidinyloxyamine (1.67 g) was dissolved in a 5M HCl solution in EtOAc (20 ml). After 1 h the solvent was removed under reduced pressure to give (S)-3-pyrrolidinyloxyamine dihydrochloride (1.04 g, 73%) as an off-white solid.

$^1$H-NMR (300 MHz, DMSO-d$_6$, ppm from TMS): δ 11.09 (3H, bb), 9.64 (1H, bb), 9.47 (1H, bb), 4.95 (1H, m), 3.55-3.00 (4H, m), 2.35-1.95 (2H, m).

Preparation 16

4-Piperidyloxyamine dihydrochloride

STEP 1: To a solution of tert-butyl 4-hydroxy-1-piperidinecarboxylate (1.00 g), triphenyl phosphine (2.62 g) and NHP (1.63 g) in THF (55 ml) at 0° C., diisopropyl azodicarboxylate (2.16 ml) was added dropwise. After stirring for 6 h, the solvent was evaporated and the crude product was purified by flash chromatography (SiO$_2$, n-hexane/EtOAc, from 8/2 to 6/4) to give of 1-tert-butoxycarbonyl-4-phthalimidoxypiperidine (1.48 g, 85%).

$^1$H-NMR (300 MHz, DMSO-d$_6$, ppm from TMS): δ 7.87 (4H, m), 4.46 (1H, m), 3.82 (2H, m), 3.23 (2H, m), 1.98 (2H, m), 1.73 (2H, m), 1.45 (9H, s).

STEP 2: To a suspension of the latter (430 mg) in MeOH (5 ml), hydrazine (26% in water, 0.23 ml) was added. After stirring at RT for 15 min, the mixture was filtered. The filtrate was evaporated to dryness and purified by flash chromatography (SiO$_2$, DCM/MeOH 9/1) to give of 1-tert-butoxycarbonyl-4-piperidyloxyamine (120 mg, 46%).

$^1$H-NMR (300 MHz, DMSO-d$_6$, ppm from TMS): δ 5.86 (2H, bb), 3.55 (3H, m), 3.00 (2H, m), 1.75 (2H, m), 1.37 (9H, s), 1.32 (2H, m).

STEP 3: The latter was dissolved in a 5M HCl solution in EtOAc (3 ml). After 1 h the solvent was removed under reduced pressure to give 4-piperidyloxyamine dihydrochloride (100 mg, 96%).

$^1$H-NMR (300 MHz, DMSO-d$_6$, ppm from TMS): δ 10.95 (3H, bb), 8.96 (2H, bb), 4.33 (1H, m), 3.13 (2H, m), 3.00 (2H, m), 2.09 (2H, m), 1.85 (2H, m).

Preparation 17

4α-Fluoroandrostan-3,17-dione

STEP 1: A mixture of dihydrotestosterone (1.00 g), 1-chloromethyl-4-fluoro-1,4-diazoniabicyclo[2.2.2]octane bis(tetrafluoroborate) or SELECTFLUOR® (1.92 g) in i-PrOH (35 ml) was refluxed for 18 h. After cooling, the resulting precipitate was filtered and the organic phase was washed with $H_2O$ and brine, dried over $Na_2SO_4$ and was evaporated to dryness. The crude reaction mixture was purified by flash chromatography ($SiO_2$, n-hexane/acetone/EOAc 75/12.5/12.5) to give 4α-fluoro-17β-hydroxyandrostan-3-one (43 mg, 4% yield).

$^1$H-NMR (300 MHz, acetone-$d_6$, ppm from TMS): δ 4.88 (dd, 1H), 3.55 (m, 2H), 2.60-0.80 (m, 20H), 1.17 (s, 3H), 0.76 (s, 3H).

STEP 2: To a stirred solution of the latter (40 mg), TPAP (4 mg), NMO (43 mg) under $N_2$ in DCM (1 ml) and molecular sieve type 4 Å powder (61 mg) were added. After 1 h the mixture was filtered and the filtrate was purified by flash chromatography ($SiO_2$, n-hexane/EtOAc 7/3) to give the title compound (38 mg, 95%).

$^1$H-NMR (300 MHz, acetone-$d_6$, ppm from TMS): δ 4.92 (dd, 1H), 2.71-0.85 (m, 20H), 1.20 (s, 3H), 0.87 (s, 3H).

Preparation 18

2α-Fluoro-17β-hydroxyandrostan-3,6-dione

STEP 1: To a suspension of NaH (55% oil dispersion, 440 mg) and diethyloxalate (2.00 g) in THF (20 ml), 6-methoxy-17β-hydroxyandrosta-4,6-dien-3-one (1.00 g) was added. The reaction mixture was then stirred at RT for 1 h. MeOH was added and the pH raised to 3-4 by means of $NH_4Cl$ and $NaH_2PO_4$ 5% and the mixture was extracted with EtOAc. The organic phase was washed with $H_2O$ and brine, dried over $Na_2SO_4$ and was evaporated to dryness. The crude reaction mixture was purified by flash chromatography ($SiO_2$, n-hexane/EtOAc 1/1) to give the 2-methoxyoxalyl-6-methoxy-17β-hydroxyandrosta-4,6-dien-3-one derivative (1.30 g, 74% yield).

$^1$H-NMR (300 MHz, acetone-$d_6$, ppm from TMS): δ 6.28 (bs, 1H), 5.37 (m, 1H), 4.32 (q, 2H), 3.65 (m, 2H), 3.63 (s, 3H), 3.20-1.00 (m, 14H), 1.01 (s, 3H), 0.83 (s, 3H).

STEP 2: To a solution of 2-methoxyoxalyl-6-methoxy-17β-hydroxyandrosta-4,6-dien-3-one in THF (20 ml), KH (122 mg) was added at 0° C., followed by the addition of N-fluorobis(phenylsulfonyl)amine (920 mg). After 15 min. the mixture was warmed to RT. MeOH (5 ml) and water (5 ml) were added and stirred for 20 min. The solvents were evaporated and HCl 1N was added. The mixture was extracted with EtOAc. The organic phase was washed with $H_2O$ and brine, dried over $Na_2SO_4$ and evaporated to dryness. The crude reaction mixture was purified by flash chromatography ($SiO_2$, n-hexane/DCM/acetone 5/3/2) to give 2α-fluoro-6-methoxy-17β-hydroxyandrosta-4,6-dien-3-one (610 mg, 76% yield).

$^1$H-NMR (300 MHz, acetone-$d_6$, ppm from TMS): δ 6.09 (m, 1H), 5.28 (m, 1H), 3.64 (m, 2H), 3.62 (s, 3H), 3.51 (ddd, 1H), 2.50-1.07 (m, 13H), 1.29 (s, 3H), 0.85 (s, 3H).

STEP 3: To a solution of 2α-fluoro-6-methoxy-17β-hydroxyandrosta-4,6-dien-3-one (610 mg) in THF (10 ml), 3N HCl (2 ml) was added and the mixture refluxed for 1 h. After cooling, $Na_2HPO_4$ 5% was added and the reaction mixture was extracted with EtOAc. The organic phase was washed with $H_2O$ and brine, dried over $Na_2SO_4$ and evaporated to dryness. The crude reaction mixture was purified by flash chromatography ($SiO_2$, n-hexane/DCM/acetone 5/3/2) to give 2α-fluoro-17β-hydroxyandrost-4-en-3,6-dione (590 mg, 84% yield).

$^1$H-NMR (300 MHz, Acetone-$d_6$, ppm from TMS): δ 5.96 (d, 1H), 5.40 (ddd, 1H), 3.65 (m, 2H), 2.70-1.20 (m, 14H), 1.38 (s, 3H), 0.84 (s, 3H).

STEP 4: To a solution of 2α-fluoro-17β-hydroxyandrost-4-en-3,6-dione (510 mg) in acetone (76 ml), NaI (950 mg) and conc. HCl (0.51 ml) were added. The mixture was then stirred at RT for 5 min. $NaHCO_3$ was added until neutrality. The organic layer was diluted with $Et_2O$ and washed with $Na_2S_2O_3$ till the brown colour disappeared. The organic phase was washed with $H_2O$ and brine, dried over $Na_2SO_4$ and was evaporated to dryness. The crude reaction mixture was purified by flash chromatography ($SiO_2$, n-hexane/DCM/acetone 5/3/2) to give the title compound in 72% yield.

$^1$H-NMR (300 MHz, acetone-$d_6$, ppm from TMS): δ 5.24 (ddd, 1H), 3.64 (m, 2H), 2.95-1.10 (m, 17H), 1.09 (s, 3H), 0.78 (s, 3H).

Preparation 19

4α-Acetoxyandrostan-3,17-dione

STEP 1: To a solution of androst-5-ene-3,17-dione (2.00 g) in toluene (10 ml) at 15° C., AcOH (10 ml) and LTA (3.40 g) were added. After stirring for 2 h, the mixture was warmed to RT and stirred for 24 h. The reaction was quenched by addition of $H_2O$ and extracted three times with EtOAc. The combined organic extracts were washed with $H_2O$, brine, dried over $Na_2SO_4$, and evaporated to dryness. The crude product was purified by triturating with a 1:1 mixture of n-hexane:EtOAc (3 ml) to give 4α-acetoxyandrost-5-ene-3,17-dione (600 mg, 25%).

$^1$H-NMR (300 MHz, acetone-$d_6$, ppm from TMS): δ 5.88 (m, 1H), 5.75 (m, 1H), 2.85-1.10 (m, 17H), 2.15 (s, 3H), 1.39 (s, 3H), 0.90 (s, 3H).

STEP 2: To a suspension of 4α-acetoxyandrost-5-ene-3,17-dione (600 mg) in MeOH (20 ml) at 0° C., $NaBH_4$ (70 mg) was added. The mixture was warmed and stirred for 1 h at RT. The solution was neutralized by addition of 5% $NaH_2PO_4$ and the organic solvent was evaporated. The residue was taken up in $H_2O$ and extracted with DCM. The combined organic extracts were washed with brine, dried over $Na_2SO_4$ and evaporated to dryness. The resulting 4α-acetoxyandrost-5-ene-3,17β-diol (600 mg) was obtained as a 3α:3β mixture and used without purification in the next step.

$^1$H-NMR (300 MHz, DMSO-$d_6$, ppm from TMS): δ 5.50-3.15 (m, 6H), 2.07 (s, 3H), 2.00-0.83 (m, 17H), 0.98 (s, 3H), 0.63 (s, 3H).

STEP 3: The latter mixture was stirred under a $H_2$ atmosphere for 24 h in the presence of 5% Pd/C (0.60 g) in MeOH (40 ml). The mixture was filtered through celite and the filtrate was evaporated to dryness. The crude reaction mixture was purified by flash chromatography ($SiO_2$, EtOAc/n-hexane 4/6) to give of a 3α:3β mixture of 4α-acetoxyandrostan-3,17β-diol (380 mg, 63%).

$^1$H-NMR (300 MHz, DMSO-$d_6$, ppm from TMS): δ 4.74 (d, 1H), 4.59 (dd, 1H), 4.40 (d, 1H), 3.40 (m, 1H), 3.27 (m, 1H), 1.99 (s, 3H), 1.85-0.55 (m, 20H), 0.81 (s, 3H), 0.60 (s, 3H).

STEP 4: A solution of the 3α:3β mixture of 4α-acetoxyandrostan-3,17β-diol (380 mg), TPAP (38 mg), NMO (383 mg) under $N_2$ in DCM (15 ml) was stirred in the presence of 4 Å molecular sieves (540 mg) for 1 h. The mixture was filtered and the filtrate was purified by flash chromatography ($SiO_2$, n-hexane/EtOAc 7/3) to give the title compound (353 mg, 93%).

$^1$H-NMR (300 MHz, acetone-$d_6$, ppm from TMS): δ 5.04 (dd, 1H), 2.75-0.80 (m, 20H), 2.07 (s, 3H), 1.24 (s, 3H), 0.87 (s, 3H).

Preparation 20

3-(E)-{2-[N-(9-Fluorenylmethoxycarbonyl)]-[3-(R)-pyrrolidinyl]oxyimino-4-(spirocyclopropane)}androst-5-en-17-one STEP 1: 3-(E)-{2-[N-(9-fluorenylmethoxycarbonyl)]-[3-(R)-pyrrolidinyl]oxyimino-4-(spirocyclopropane)}androst-5-en-17β-ol was obtained in 94% yield (189 g) following the procedure described in Preparation 1—Step 1 starting from (E)-3-[3-(R)-pyrrolidinyl]oxyimino-4-(spirocyclopropane)androst-5-en-17β-ol (Ex. 29, 129 mg) and 9-fluorenylmethoxycarbonyl chloride (84 mg).

$^1$H-NMR (300 MHz, Acetone-$d_6$, ppm from TMS): δ 7.90-7.30 (m, 8H), 5.32 (m, 1H), 4.65 (m, 1H), 4.31 (m, 3H), 3.65-3.30 (m, 6H), 2.94 (m, 1H), 2.35-0.52 (m, 22H), 1.18 (s, 3H), 0.76 (s, 3H).

STEP 2: The title compound was obtained in 90% yield (169 mg) following the procedure described in Preparation 1—Step 2 starting from 3-(E)-{2-[N-(9-fluorenylmethoxycarbonyl)]-[3-(R)-pyrrolidinyl]oxyimino-4-(spirocyclopropane)}androst-5-en-17β-ol (189 mg).

$^1$H-NMR (300 MHz, acetone-$d_6$, ppm from TMS): δ 7.90-7.20 (m, 8H), 5.36 (m, 1H), 4.70 (m, 1H), 4.32 (m, 3H), 3.75-0.51 (m, 27H), 1.22 (s, 3H), 0.88 (s, 3H).

Preparation 21

4-Spirocyclopentane-17β-hydroxyandrostan-3-one

The title compound was obtained in 90% yield (106 mg) following the hydrogenation procedure described in Preparation 9—Step 4 starting from 4-spirocyclopentane-17β-hydroxy-5-androsten-3-one (115 mg) in EtOAc (12 ml).

$^1$H-NMR (300 MHz, acetone-$d_6$, ppm from TMS): δ 3.55 (m, 2H), 3.85-0.68 (m, 28H), 1.09 (s, 3H), 0.74 (s, 3H).

Preparation 22

3-(E)-{2-[N-(9-Fluorenylmethoxycarbonyl)]-[3-(R)-pyrrolidinyl]oxyimino-4-(spirocyclopentane)}androst-5-en-17-one STEP 1: 3-(E)-{2-[N-(9-fluorenylmethoxycarbonyl)]-[3-(R)-pyrrolidinyl]oxyimino-4-(spirocyclopentane)}androst-5-en-17β-ol was obtained in 93% yield (464 g) following the procedure described in Preparation 1—Step 1 starting from (E)-3-[3-(R)-pyrrolidinyl]oxyimino-4-(spirocyclopentane)androst-5-en-17β-ol (Example 42, 327 mg) and 9-fluorenylmethoxycarbonyl chloride (198 mg).

$^1$H-NMR (300 MHz, acetone-$d_6$, ppm from TMS): δ 7.90-7.28 (m, 8H), 5.61 (m, 1H), 4.78 (m, 1H), 4.31 (m, 3H), 3.70-3.35 (m, 6H), 2.90-0.86 (m, 27H), 0.82 (s, 3H), 0.71 (s, 3H).

STEP 2: The title compound was obtained in 90% yield (423 mg) following the procedure described in Preparation 1—Step 2 and starting from 3-(E)-{2-[N-(9-fluorenylmethoxycarbonyl)]-[3-(R)-pyrrolidinyl]oxyimino-4-(spirocyclopentane)}-androst-5-en-17β-ol (464 mg).

$^1$H-NMR (300 MHz, $CD_2Cl_2$, ppm from TMS): δ 7.85-7.30 (m, 8H), 5.63 (m, 1H), 4.78 (m, 1H), 4.32 (m, 3H), 3.80-3.40 (m, 4H), 2.93-0.96 (m, 27H), 0.84 (s, 6H).

Preparation 23

4-Spirocyclopentane-7α,17β-dihydroxyandrostan-3-one

STEP 1: To a suspension of 4-spirocyclopentane-17β-hydroxy-5-androsten-3-one (300 mg) in 2-methyl-2-ethyl-1,3-dioxolane (20 ml), ethylene glycol (0.2 ml) and PTSA (50 mg) were added. After stirring the mixture for 48 h at RT, 5% aqueous $NaHCO_3$ solution was added, and the mixture was extracted with EtOAc. The combined organic extracts were washed with brine, dried over $MgSO_4$, filtered and evaporated to dryness. The crude product was purified by flash chromatography ($SiO_2$, n-hexane/EtOAc 75/25) to give 3,3-ethylenedioxy-4-spirocyclopentan-5-androsten-17β-ol (262 mg, 77%).

$^1$H-NMR (300 MHz, acetone-$d_6$, ppm from TMS): δ 5.38 (m, 1H), 4.0-3.8 (m, 4H), 3.55 (m, 2H), 2.20-0.85 (m, 26H), 1.11 (s, 3H), 0.74 (s, 3H).

STEP 2: 1M $BH_3$.THF complex in THF (3.89 ml) was added to a stirred solution of 3,3-ethylenedioxy-4-spirocyclopentane-5-androsten-17β-ol (251 mg) in THF (16 ml) at 0° C., under $N_2$. The mixture was stirred at RT overnight. $H_2O$ (5 ml) was cautiously added dropwise at 0° C. The mixture was saturated with NaCl and extracted three times with $Et_2O$. The combined organic extracts were washed with 5% aqueous $NaHCO_3$ solution, brine dried over NaCl and $Na_2SO_4$, filtered and evaporated to dryness. The crude product was dissolved in THF (16 ml) at 0° C. and 10% aqueous NaOH solution (5.7 ml), 30-32 wt. % $H_2O_2$ solution in water (4.4 ml) were added and the mixture was stirred at RT for 2 h. The mixture was extracted with $Et_2O$. The combined organic extracts were washed with 5% aqueous $NaHCO_3$ solution, brine dried over $Na_2SO_4$, filtered and evaporated to dryness. The crude product was purified by flash chromatography ($SiO_2$, n-hexane/EtOAc 60/40) to give 3,3-ethylenedioxy-4-spirocyclopentan-5-androstene-7α,17β-diol (69 mg, 26%).

$^1$H-NMR (300 MHz, DMSO-$d_6$, ppm from TMS): δ 4.35 (d, 1H), 4.04 (d, 1H), 3.85 (m, 4H), 3.66 (m, 1H), 3.40 (m, 1H), 1.97-0.69 (m, 26H), 0.77 (s, 3H), 0.57 (s, 3H).

STEP 3: To a stirred solution of 3,3-ethylenedioxy-4-spirocyclopentan-5-androstene-7α,17β-diol (63 mg) in acetone (6 ml), PTSA (9 mg) was added. After stirring at RT for 3.5 h, $NaHCO_3$ was added to neutrality. The organic layer was evaporated and the aqueous phase was extracted with EtOAc. The combined organic extracts were washed with brine, dried over $Na_2SO_4$ and were evaporated to dryness to give 4-spirocyclopentan-7α,17β-dihydroxyandrostan-3-one (52 mg, 92%).

$^1$H-NMR (300 MHz, DMSO-$d_6$, ppm from TMS): δ 4.39 (d, 1H), 4.13 (d, 1H), 3.70 (m, 4H), 3.41 (m, 1H), 2.71 (m, 1H), 2.25-0.80 (m, 25H), 0.95 (s, 3H), 0.60 (s, 3H).

Preparation 24

4β-Methyl-4α,5α-epoxy-17β-hydroxyandrostan-3-one

To a stirred solution of 4-methyltestosterone (500 mg) in MeOH (60 ml) and NaOH 4N (2 ml) at 0° C., 30-32 wt. % $H_2O_2$ solution in water (2.0 ml) was added. The suspension was stirred at RT overnight. 10% aqueous $Na_2SO_3$ solution (5 ml) was cautiously added dropwise at 0° C. The mixture was saturated with NaCl and extracted three times with EtOAc. The combined organic extracts were dried over $Na_2SO_4$, filtered and evaporated to dryness. The crude product was purified by flash chromatography ($SiO_2$, toluene/tert-butyl methyl ether 80/20) to give 4β-methyl-4α,5α-epoxy-17β-hydroxyandrostan-3-one (130 mg, 25%).

$^1$H-NMR (300 MHz, acetone-$d_6$, ppm from TMS): δ 3.59 (m, 2H), 2.34-0.96 (m, 19H), 1.31 (s, 3H), 1.09 (s, 3H), 0.77 (s, 3H).

Preparation 25

4β-Ethyl-4α,5α-epoxy-17β-hydroxyandrostan-3-one

The title compound was obtained (50 mg, 48%) following the oxidation procedure described in Preparation 11, Step 3 starting from 17β-hydroxy-4-ethylandrost-4-en-3-one (Preparation 11, 100 mg).

$^1$H-NMR (300 MHz, acetone-$d_6$, ppm from TMS): δ 3.60 (m, 2H), 2.16-0.97 (m, 21H), 1.12 (s, 3H), 0.85 (t, 3H), 0.77 (s, 3H).

Preparation 26

4α-Ethyl-17β-hydroxyandrostan-3-one

The title compound was obtained (249 mg, 49%) following the reduction procedure described in Preparation 11 starting from 17β-hydroxy-4-ethylandrost-4-en-3-one (500 mg).

$^1$H-NMR (300 MHz, acetone-$d_6$, ppm from TMS): δ 3.55 (m, 2H), 2.50-0.70 (m, 23H), 1.12 (s, 3H), 0.79 (t, 3H), 0.75 (s, 3H).

Preparation 27

4β-Ethyl-6α-hydroxyandrostan-3,17-dione

To a stirred solution of 4β-ethylandrostan-3α,6α,17β-triol (Preparation 11, 237 mg) in dioxane (5.8 ml), water (1.08 ml), pyridine (0.1 ml) and NBS (249 mg) were added. After 72 h, EtOAc (70 ml), $H_2O$ (30 ml) and 10% $Na_2SO_3$ aqueous solution (24 ml) were added and the mixture was stirred for 10 min. The phases were separated and the aqueous phase was extracted with EtOAc. The combined organic extracts were washed with of 5% aqueous $NaHCO_3$, brine, dried over $MgSO_4$, filtered and evaporated to dryness. The crude product was purified by flash chromatography ($SiO_2$, EtOAc/n-hexane 70/30) to give the title compound as a white solid (135 mg, 57%).

$^1$H-NMR (300 MHz, acetone-$d_6$, ppm from TMS): δ 3.90 (m, 1H), 3.52 (d, 1H), 2.80-0.92 (m, 21H), 1.15 (s, 3H), 0.85 (s, 3H), 0.80 (t, 3H)

Preparation 28

4,4-Dimethyl-5α,17β-dihydroxyandrostan-3-one

STEP 1: 3,3-Ethylenedioxy-4,4-dimethyl-5-androsten-17β-ol (195 mg, 34%) was obtained following the procedure described in Preparation 23, Step 1, starting from 4,4-dimethyl-17β-hydroxy-5-androsten-3-one (500 mg).

$^1$H-NMR (300 MHz, DMSO-$d_6$, ppm from TMS): δ 5.38 (m, 1H), 4.43 (d, 1H), 3.81 (m, 4H), 3.42 (m, 1H), 2.11-0.75 (m, 17H), 1.14 (s, 3H), 1.06 (s, 3H), 0.94 (s, 3H), 0.62 (s, 3H)

STEP 2: To a stirred solution of 3,3-ethylenedioxy-4,4-dimethyl-5-androsten-17β-ol (190 mg) in THF (3.5 ml) at 0° C., under $N_2$, 1M $BH_3$.THF complex in THF (3.3 ml) was added in five portions over 5 days. The reaction mixture was cautiously quenched by dropwise addition of $H_2O$ at 0° C. (1.5 ml), followed by 4N NaOH (0.16 ml) and by 30-32 wt. % $H_2O_2$ solution in water (0.056 ml). After 24 h, EtOAc and brine were added, the phases were separated and the aqueous phase was extracted with EtOAc. The combined organic extracts were washed with brine, dried over $MgSO_4$, filtered and evaporated to dryness. The crude product was purified by flash chromatography ($SiO_2$, n-hexane/DCM/acetone 80/10/10) to give 3,3-ethylenedioxy-4,4-dimethylandrostan-5α,17β-diol (80 mg, 23%).

$^1$H-NMR (300 MHz, DMSO-$d_6$, ppm from TMS): δ 4.38 (d, 1H), 4.05-3.78 (m, 4H), 3.69 (s, 1H), 3.41 (m, 1H), 1.88-0.75 (m, 19H), 1.02 (s, 3H), 0.99 (s, 3H), 0.83 (s, 3H), 0.59 (s, 3H)

STEP 3: The title compound was obtained (50 mg, 83%) following the procedure described in Preparation 23, Step 3, starting from 3,3-ethylenedioxy-4,4-dimethylandrostane-5α,17β-diol (68 mg).

$^1$H-NMR (300 MHz, DMSO-$d_6$, ppm from TMS): δ 4.40 (d, 1H), 4.22 (s, 1H), 3.41 (m, 1H), 2.70-0.78 (m, 19H), 1.07 (s, 6H), 0.95 (s, 3H), 0.67 (s, 3H).

Biological Results

The compounds iof the invention show affinity and inhibit the enzymatic activity of the $Na^+,K^+$-ATPase. To test the inhibition of the activity, the $Na^+,K^+$-ATPase was purified according to Jorghensen (Jorghensen P., *BBA*, 1974, 356, 36) and Erdmann (Erdmann E. et al., *Arzneim. Forsh.*, 1984, 34, 1314) and the inhibition was measured as % of hydrolysis of $^{32}$P-ATP in the presence and in the absence of the tested compound (Mall F. et al., *Biochem. Pharmacol.*, 1984, 33, 47): see Table 1. Compounds 22c and 22d, described by De Munari S., et al., *J. Med. Chem.*, 2003, 64, 3644-3654, are reported as reference compounds with a lower inhibitory potency than the compounds of the present invention.

TABLE 1

Dog Kidney $Na^+$, $K^+$-ATPase Inhibition

| Example n° | $Na^+, K^+$-ATPase Inhibition $IC_{50}$, μM | Example n° | $Na^+, K^+$-ATPase Inhibition $IC_{50}$, μM |
|---|---|---|---|
| I-aa | 4.9 | I-ag | 3.9 |
| I-ai | 1.9 | I-aj | 1.4 |
| I-ak | 2.0 | I-al | 2.6 |
| I-am | 1.7 | I-an | 1.5 |
| I-ao | 1.3 | I-at | 1.7 |
| I-au | 2.2 | I-bb | 1.5 |
| I-bc | 1.8 | I-bd | 0.13 |
| I-be | 0.049 | I-bf | 2.4 |
| I-bg | 0.84 | I-bh | 1.1 |
| I-bi | 1.3 | I-bj | 2.1 |
| I-bk | 1.9 | I-bl | 0.55 |
| I-bn | 2.7 | I-bo | 0.69 |
| I-bq | 3.1 | I-bs | 1.1 |
| I-bv | 3.9 | I-bw | 1.8 |
| I-bx | 0.065 | I-by | 2.2 |
| I-bz | 3.7 | | |
| Compd. 22c | 25.0 | Compd. 22d | 6.0 |

The compounds of the present invention possess positive inotropic activity, as taught by Cerri et al., in *J. Med. Chem.* 2000, 43, 2332 who demonstrated that compounds affecting $Na^+,K^+$-ATPase can increase the contractile force of the heart, and have a low toxicity when compared with standard cardiotonic steroids, e.g. digoxin.

The compounds of the present invention possess a higher efficacy compared to compound 22d ((E)-3-(2-aminoethoxy-imino)-4α-methylandrostan-6,17-dione hydrochloride) reported by De Munari S. et al. in *J. Med. Chem.*, 2003, 64, 3644-3654. The activity of some compounds of general formula (I) on the above mentioned tests are shown in the following Table 2. The inotropic activity is shown as maximum increase in contractile force ($E_{max}$ measured as +dP/dT$_{max}$), dose inducing maximum positive inotropic effect ($ED_{max}$), inotropic potency ($ED_{80}$, dose increasing +dP/dT$_{max}$ by 80%); the toxicity as the ratio between lethal dose and inotropic potency (calculated in the died animals). All animals, previously anesthetized, were administered the drug through infusion over a 90 minute period.

TABLE 2 inotropic effect and lethal dose in anesthetized guinea-pig

| Examples | Notes | $E_{max}$ % increase in $+dP/dT_{max}$ | $ED_{max}$ µmol/kg | $ED_{80}$ µmol/kg | Dead/treated | Lethal dose/ $ED_{80}$ | Maximum dose infused µmol/kg |
|---|---|---|---|---|---|---|---|
| I-be |  | 179 | 2.81 | 1.40 | 3/3 | 7.8 | 12.6 |
| I-bh |  | 210 | 14.0 | 7.00 | 2/2 | 7.5 | 100.8 |
| Digoxin |  | 158 | 0.65 | 0.29 | 10/10 | 4.0 | 1.16 |
| compound 22d | Tremors | 190 | 149 | 23.0 | 0/3 | nd | 250.3 |

As reported in Table 2, the compounds showed positive inotropic effects with higher safety ratios than those displayed by digitoxin as demonstrated by the lethal dose/$ED_{80}$ ratios that are higher. It is noteworthy that compound 22d necessitated a very high dose to elicit the inotropic effect, expressed either as $ED_{80}$ or $ED_{max}$, in comparison with the other three compounds. Furthermore, tremors and contractions appeared during the infusion, even though no animals died. However, no higher doses were tested because of the presence of toxic effects, such as tremors that did not justify the attempt to overcome the high dose of 250 µmol/kg.

The compounds of the present invention possess also antihypertensive activity, as taught by Ferrari P. et al., in *Cardiovascular Drug Reviews,* 1999, 17, 39-57, who demonstrated that compounds affecting $Na^+,K^+$-ATPase can lower blood pressure in models of hypertension.

The invention claimed is:
1. A compound of general formula I

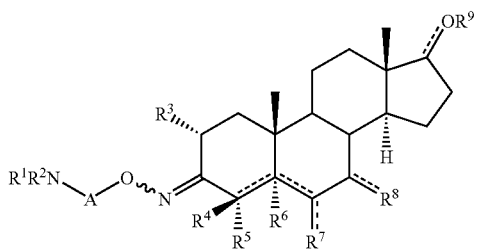

wherein:
A is a $C_1$-$C_6$ straight or branched alkylene;
$R^1$ is $C_1$-$C_6$ alkyl;
wherein $R^1$ and A are taken together with the nitrogen atom to form an unsubstituted or substituted saturated or unsaturated mono heterocyclic 4-, 5- or 6-membered ring;
$R^2$ is H;
$R^3$ is hydrogen, hydroxy, fluoro, chloro or bromo;
when the symbol === in position 4 represents a single bond $R^4$ is hydrogen, fluoro, chloro, bromo, $C_1$-$C_6$ alkyl or hydroxy and $R^5$ is hydrogen, fluoro, chloro, bromo, methyl, ethyl or hydroxy;
$R^4$ and $R^5$, when the symbol === in position 4 represents a single bond, are taken together with the carbon atom that they are linked to, to form a spirocyclopropane or spirocyclopentane ring; when the symbol === in position 4 represents a double bond $R^4$ is fluoro, chloro, bromo, $C_1$-$C_6$ alkyl or hydroxy and $R^5$ is not present;
$R^6$ is H, or $OR^{10}$ or is absent when the symbol === in positions 4 or 5 represents a double bond;
$R^5$ and $R^6$, when the symbols === in positions 4 and 5 represent single bonds, are taken together to form an oxirane or a cyclopropane ring;
when the bond === linking the carbon atom in position 6 of the androstane skeleton with $R^7$ is a double bond, $R^7$ is O, with the meaning of a keto group, or N〜$OR^{11}$ or $CR^{12}R^{13}$;
when the bond === linking the carbon atom in position 7 of the androstane skeleton with $R^8$ is a double bond, $R^8$ is O, with the meaning of a keto group, or N〜$OR^{11}$ or $CR^{12}R^{13}$;
when the bond === linking the carbon atom in position 6 of the androstane skeleton with $R^7$ is a single bond, $R^7$ is H, $C_1$-$C_6$ alkyl group, $OR^{14}$, vinyl, ethynyl, CHO, $COOR^{15}$, $ONO_2$, NHCHO, spirocyclopropane, spirooxirane, where the alkyl group is optionally substituted by one or more hydroxy, methoxy or ethoxy;
$R^6$ and $R^7$, when the symbols === in positions 4, 5 and 6 represent single bonds, are taken together to form an oxirane or cyclopropane ring;
when the bond === linking the carbon atom in position 7 of the androstane skeleton with $R^8$ is a single bond, $R^8$ is H, $C_1$-$C_6$ alkyl group, $OR^{14}$, vinyl, ethynyl, CHO, $COOR^{15}$, $ONO_2$, NHCHO, spirocyclopropane, spirooxirane, where the alkyl group is optionally substituted by one or more hydroxy, methoxy or ethoxy;
$R^9$ is H, $C_1$-$C_6$ alkyl group or $C_2$-$C_7$ alkylcarbonyl group, when the bond === in position 17 of the androstane skeleton is a single bond, and when the bond === in position 17 is a double bond $R^9$ is not present;
$R^{10}$ is H, $C_1$-$C_6$ alkyl or $C_2$-$C_7$ alkylcarbonyl group;
$R^{11}$ is H, $C_1$-$C_6$ alkyl or $C_2$-$C_7$ alkylcarbonyl group;
$R^{12}$ and $R^{13}$, which are the same or different, are H, $C_1$-$C_6$ alkyl or F;
$R^{14}$ is H, $C_1$-$C_6$ alkyl or $C_2$-$C_7$ alkylcarbonyl group;
$R^{15}$ is H or $C_1$-$C_6$ alkyl;
$R^{10}$, $R^{11}$, $R^{12}$, $R^{13}$, $R^{14}$, and $R^{15}$, when present in the same compound in different positions, are the same or different;
the symbol 〜 represents an E or Z diastereoisomer;
the symbol === in positions 4, 5, 6, 7, and 17 represents, independently, a single or double bond, and when it is a single exocyclic bond in positions 6, 7, or 17, it can assume an α or a β orientation;
with the following provisos:
when $R^4$ is H and $R^5$ is methyl, both $R^7$ and $OR^9$ do not have the meaning of keto groups;

when $R^4$ is hydroxy, $R^5$ is not hydroxy, fluoro, bromo, and chloro and viceversa; that $R^3$, $R^4$ and $R^5$ are not hydrogen at the same time.

2. The compound according to claim 1, which is selected from the group consisting of:
- (E)-3-[3(R)-pyrrolidinyl]oxyimino-4,4-dimethylandrost-5-ene-17β-ol
- (E)-3-[3(R)-pyrrolidinyl]oxyimino-4,4-dimethylandrostane17β-ol;
- (E)-3-[3(S)-pyrrolidinyl]oxyimino-4,4-dimethylandrostane17β-ol;
- (E)-3-[3(R)-pyrrolidinyl]oxyimino-4,4-dimethylandrostane-17-one;
- (E)-3-[3(R)-pyrrolidinyl]oxyimino-4,4-dimethylandrostane5α,6α,17β-triol;
- (E)-3-[3(R)-pyrrolidinyl]oxyimino-5α,6α-dihydroxy-4,4-dimethylandrostan-17-one;
- (E)-3-[3'(R)-pyrrolidinyl]oxyimino-5αhydroxy-4,4-dimethylandrostan-6,17-dione;
- (E)-3-[3'(R)-pyrrolidinyl]oxyimino-4,4-dimethyl-5α,6α-epoxyandrostan-17β-ol;
- (E)-3-[3'(R)-pyrrolidinyl]oxyimino)-4,4-dimethyl-6α-hydroxymethylandrostane-7α,17β-diol;
- (E)-3-[4-piperidylyloxyimino)-4,4-dimethyl-6α-hydroxmethylandrostane-7α,17β-diol;
- (E)-3-[3'-(R)-pyrrolidinyl]oxyimino-4-(spirocyclopropane)-5-androstene-17β-ol;
- (E)-3-[3'-(R)-pyrrolidinyl]oxyimino-4β-ethylandrostane-6,17-dione;
- (E)-3-[(3'-(R)-pyrrolidinyl)oxyimino]-2α-fluoroandrostane-17β-ol;
- (E)-3-[(3'-(R)-pyrrolidinyl)oxyimino]2α- fluoroandrostane-17-one;
- (E)-3-[(3'-(R)-pyrrolidinyl)oxyimino]2α-fluoro-17β-hydroxyandrostan-6-one;
- (E)-3-[(3-(R)-pyrrolidinyl)oxyimino]2α-fluoro-6-[E]hydroxyimino-androstane-17β-ol;
- (E)-3-[(3-(R)-pyrrolidinyl)oxyimino]2α-fluoro-6-(E) methoxyimino-androstane-17β-ol;
- (E)-3-[(3'-(R)-pyrrolidinyl)oxyimino]-4α-fluoroandrostane-17-one;
- 3-[3-(R)-pyrrolidinyl]oxyimino-4-hydroxandrostane-17-one;
- (E)-3-[(3'-(R)-pyrrolidiny)oxyimino]-4spirocyclopropan-5androsten-17-one;
- (E)-3-[(3'-(R)-pyrrolidiny)oxyimino]-4spirocyclopentan-5androsten-17β-ol;
- (E)-3-[(3'-(R)-pyrrolidiny)oxyimino]-4spirocyclopentanandrostan-17-β-ol;
- (E)-3-[(3'-(R)-pyrrolidiny)oxyimino]-4-spirocyclopentan-5-androsten-17-one;
- (E)-3-[(3-(R)-pyrrolidiny)oxyimino]-4-spirocyclopentaneandrostane-7α,17β-diol;
- (E)-3-[(3'-(R)-pyrrolidiny)oxyimino]-4α-ethylandrostane-17β-ol;
- (E)-3-[(3'-(R)-pyrrolidinyl]oxyimino-4β-ethyl-6-α-hydroxyandrostane-17-one; and
- (E)-3-[(3-(R)-pyrrolidiny]oxyimino-4,4-dimethylandrostane-5α,17β-diol.

3. A process for preparing the compound according to claim 1, which comprises reacting a compound of general formula II

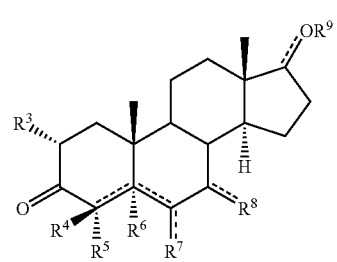

where the symbols $R^3$, $R^4$, $R^5$, $R^6$, $R^7$, $R^8$, $R^9$, and === have the meanings defined in claim 1, with
compounds of general formula (III),
$R^1R^2$N-A-ONH$_2$ (III)
where $R^1$, $R^2$, and A have the meanings defined in claim 1.

4. The process according to claim 3 wherein the reaction is conducted in a polar solvent at a temperature ranging from 0° C. to the reflux temperature.

5. A method of treating a cardiovascular disorder and organ complications thereof selected from the group consisting of heart failure and/or hypertension comprising administering an effective amount of the compound of general formula I of claim 1 to a subject in need thereof.

6. A pharmaceutical composition comprising one or more compounds according to claim 1 in combination with excipients and/or pharmacologically acceptable diluents.

7. A process for the preparation of the pharmaceutical composition of claim 6 further comprising mixing said pharmaceutical composition with suitable excipients.

* * * * *

UNITED STATES PATENT AND TRADEMARK OFFICE
CERTIFICATE OF CORRECTION

PATENT NO. : 8,664,210 B2
APPLICATION NO. : 12/680988
DATED : March 4, 2014
INVENTOR(S) : Cerri et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 482 days.

Signed and Sealed this
Twenty-ninth Day of September, 2015

Michelle K. Lee
*Director of the United States Patent and Trademark Office*